(12) United States Patent
Keler et al.

(10) Patent No.: US 8,586,720 B2
(45) Date of Patent: Nov. 19, 2013

(54) ANTIBODIES THAT BIND HUMAN DENDRITIC AND EPITHELIAL CELL 205 (DEC-205)

(75) Inventors: Tibor Keler, Ottsville, PA (US); Lizhen He, Allentown, PA (US); Venky Ramakrishna, Riegelsville, PA (US); Laura A. Vitale, Doyelstown, PA (US)

(73) Assignee: Celldex Therapeutics Inc., Needham, MA (US)

( * ) Notice: Subject to any disclaimer, the term of this patent is extended or adjusted under 35 U.S.C. 154(b) by 0 days.

(21) Appl. No.: 13/542,909

(22) Filed: Jul. 6, 2012

(65) Prior Publication Data
US 2012/0309031 A1     Dec. 6, 2012

Related U.S. Application Data

(62) Division of application No. 12/266,745, filed on Nov. 7, 2008, now Pat. No. 8,236,318.

(60) Provisional application No. 61/002,253, filed on Nov. 7, 2007, provisional application No. 61/191,551, filed on Sep. 10, 2008.

(51) Int. Cl.
*C07H 21/04*     (2006.01)

(52) U.S. Cl.
USPC .................................................. 536/23.53

(58) Field of Classification Search
None
See application file for complete search history.

(56) References Cited

U.S. PATENT DOCUMENTS

| | | | |
|---|---|---|---|
| 2,857,090 A | 10/1958 | Fallert | |
| 2,887,389 A | 5/1959 | Linville | |
| 3,164,316 A | 1/1965 | Wurster et al. | |
| 3,353,740 A | 11/1967 | Outwater | |
| 3,447,735 A | 6/1969 | Whitney | |
| 3,552,633 A | 1/1971 | Ketler | |
| 3,698,548 A | 10/1972 | Stenzel et al. | |
| 3,883,067 A | 5/1975 | McGlynn et al. | |
| 4,267,959 A | 5/1981 | Gilbert | |
| 4,474,893 A | 10/1984 | Reading | |
| 4,946,778 A | 8/1990 | Ladner et al. | |
| 4,954,617 A | 9/1990 | Fanger et al. | |
| 5,455,030 A | 10/1995 | Ladner et al. | |
| 5,476,786 A | 12/1995 | Huston | |
| 5,541,110 A | 7/1996 | Siegall | |
| 5,545,807 A | 8/1996 | Surani et al. | |
| 5,698,679 A | 12/1997 | Nemazee | |
| 5,869,057 A | 2/1999 | Rock | |
| 5,876,917 A | 3/1999 | Hart et al. | |
| 5,922,845 A | 7/1999 | Deo et al. | |
| 6,080,409 A | 6/2000 | Laus et al. | |
| 6,117,977 A | 9/2000 | Lasky et al. | |
| 6,277,959 B1 | 8/2001 | Valladeau et al. | |
| 6,340,569 B1 | 1/2002 | Ball et al. | |
| 6,432,666 B1 | 8/2002 | Hart | |
| 6,440,418 B1 | 8/2002 | Black et al. | |
| 6,479,247 B1 | 11/2002 | Hart | |
| 6,756,478 B2 | 6/2004 | Valladeau et al. | |
| 6,834,793 B2 | 12/2004 | Sutherland | |
| 7,201,714 B2 | 4/2007 | Zoeckler et al. | |
| 7,579,187 B2 * | 8/2009 | Kataoka et al. | 435/330 |
| 2002/0187131 A1 | 12/2002 | Hawiger et al. | |
| 2003/0194391 A1 | 10/2003 | Ashman et al. | |
| 2004/0001853 A1 | 1/2004 | George et al. | |
| 2004/0258688 A1 | 12/2004 | Hawiger et al. | |
| 2005/0037001 A1 | 2/2005 | Germeraad et al. | |
| 2005/0186612 A1 | 8/2005 | Hart | |
| 2007/0063005 A1 | 3/2007 | Gomes et al. | |

FOREIGN PATENT DOCUMENTS

| | | |
|---|---|---|
| WO | 86/01533 A1 | 3/1986 |
| WO | 88/00052 A1 | 1/1988 |
| WO | 92/03918 A1 | 3/1992 |
| WO | 92/07579 A1 | 5/1992 |
| WO | 93/04187 A1 | 3/1993 |
| WO | 93/12227 A1 | 6/1993 |
| WO | 94/10332 A1 | 5/1994 |
| WO | 95/15340 A1 | 6/1995 |
| WO | 96/23882 A1 | 8/1996 |
| WO | 97/45449 A1 | 12/1997 |
| WO | 98/15579 A1 | 4/1998 |
| WO | 98/24884 A1 | 6/1998 |
| WO | 99/02562 A1 | 1/1999 |
| WO | 99/16455 A1 | 4/1999 |
| WO | 99/24554 A2 | 5/1999 |
| WO | 99/47673 A2 | 9/1999 |
| WO | 99/55369 A1 | 11/1999 |
| WO | 99/58678 A2 | 11/1999 |
| WO | 00/00156 A2 | 1/2000 |
| WO | 00/00592 A1 | 1/2000 |
| WO | 00/18803 A2 | 4/2000 |
| WO | 00/63251 A1 | 10/2000 |
| WO | 01/25492 A1 | 4/2001 |
| WO | 01/85798 A2 | 11/2001 |
| WO | 03/040169 A2 | 5/2003 |
| WO | 2004/026326 A2 | 4/2004 |
| WO | 2004/035619 A1 | 4/2004 |
| WO | 2004/074432 A2 | 9/2004 |
| WO | 2005/018610 A1 | 3/2005 |
| WO | WO 2006028197 A1 * | 3/2006 |
| WO | 2007/067730 A2 | 6/2007 |
| WO | WO 2007067991 A2 * | 6/2007 |

OTHER PUBLICATIONS

Apostolopoulos, Vasso et al., "Ex vivo targeting of the macrophage mannose receptor generates anti-tumor CTL responses," Vaccine, vol. 18:3174-3184 (2000).

Austyn, Jonathan M. et al., "Isolation and Characterization of Dendritic Cells from Mouse Heart and Kidney," Journal of Immunology, vol. 152:2401-2410 (1994).

(Continued)

*Primary Examiner* — Amy Juedes
(74) *Attorney, Agent, or Firm* — Nelson Mullins Riley & Scarborough LLP; Jane R. Remillard, Esq.; Jill Gorny Sloper, Esq.

(57) ABSTRACT

Isolated monoclonal antibodies which bind to human DEC-205 and related antibody-based compositions and molecules are disclosed. Also disclosed are pharmaceutical compositions comprising the antibodies, as well as therapeutic and diagnostic methods for using the antibodies.

6 Claims, 10 Drawing Sheets

(56) References Cited

OTHER PUBLICATIONS

Badiee, Ali et al., "Enhanced delivery of immunoliposomes to human dendritic cell by targeting the multilectin receptor DEC-205," Vaccine, vol. 25:4757-4766 (2007).
Berard, Frederic et al., "Cross-Priming of Naive CD8 T Cells against Melanoma Antigens Using Dendritic Cells Loaded with Killed Allogeneic Malanoma Cells," J. Exp. Med., vol. 192(11):1535-1543 (2000).
Berlyn, Kathleen A. et al., "Generation of CD4+ and CD8+ T Lymphocyte Responses by Dendritic Cells Armed with PSA/Anti-PSA (Antigen/Antibody) Complexes," Clinical Immunology, vol. 101(3):276-283 (2001).
Bird, Robert E. et al., "Single-Chain Antigen-Binding Proteins," Science, vol. 242(4877):423-426 (1988).
Bonifaz, Laura et al., "Efficient Targeting of Protein Antigen to the Dendritic Cell Receptor DEC-205 in the Steady State Leads to Antigen Presentation on Major Histocompatibility Complex Case I Products and Peripheral CD8+T Cell Tolerance," J. Exp. Med., vol. 196(12):1627-1938 (2002).
Breel, M. et al., "Subpopulations of lymphoid and non-lymphoid cells in bronchus-associated lymphoid tissue (BALT) of the mouse," Immunology, vol. 63:657-662 (1988).
Brennan, Maureen et al., "Preparation of Bispecific Antibodies by Chemical Recombination of Monoclonal Immunoglobulin G1 Fragments," Science, vol. 229:81-83 (1985).
Butler, Matt et al., "Altered expression and endocytic function of CD205 in human dendritic cells, and detection of a CD205-DCL-1 fusion protein upon dendritic cell maturation," Immunology, vol. 120:362-371 (2006).
Casset, Florence et al., "A peptide mimetic of an anti-CD4 monoclonal antibody in rational design," Biochemical and Biophysical Research Communications, vol. 307:198-205 (2003).
Chen, Wen-Ji et al., "NPXY, a Sequence Often Found in Cytoplasmic Tails, is Required for Coated Pit-mediated Internalization of the Low Density Lipoprotein Receptor," The Journal of Biological Chemistry, vol. 265(6):3116-3123 (1990).
Chen, Yvonne et al., "Selection and Analysis of an Optimized Anti-VEGF Antibody: Crystal Strucutre of an Affinity-matured Fab in Complex with Antigen," J. Mol. Biol., vol. 293:865-881 (1999).
Cheong, Cheolho et al., "Improved cellular and humoral immune responses in vivo following targeting of HIV Gag to dendritic cells within human anti-human DEC205 monoclonal antibody," Blood, vol. 116(19):3828-3838 (2010).
Chien, Nadine C. et al., "Significant structural and functional change of an antigen-binding site by a distant amino acid substitution: Proposal of a structural mechanism," Proc. Natl. Acad. Sci. USA, vol. 86:5532-5536 (1989).
Collawn, James F. et al., "Transferrin Receptor Internalization Sequence YXRF Implicates a Tight Turn as the Structural Recognition Motif for Endocytosis," Cell, vol. 63:1061-1072 (1990).
Cox, John C. et al., "Adjuvants—a classification and review of their modes of action," Vaccine, vol. 15(3):248-256 (1997).
De Maagd, R.A. et al., "The human thymus microenvironment: heterogeneity detected by monoclonal anti-epithelial cell antibodies," Immunology, vol. 54:745-754 (1985).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
Drickamer, K. et al., "Biology of animal lectins," Annu. Rev. Cell Biol., vol. 9:237-264 (1993).
Ezekowitz, R. Alan B. et al., "Molecular Characterization of the Human Macrophage Mannose Receptor: Demonstration of Multiple Carbohydrate Recognition-like Domains and Phagocytosis of Yeasts in Cos-1 Cells," J. Exp. Med., vol. 172:1785-1794 (1990).
Frleta, Davor et al, "Class II-targeted antigen is superior to CD40-targeted antigen at stimulating humoral responses in vivo," International Immunopharmacology, vol. 1:265-275 (2001).
Galfre, G. et al., "Antibodies to major histocompatibility antigens produced by hybrid cell lines," Nature, vol. 266 (7):550-552 (1977).
Geissmann, Frédéric et al., "A Subset of Human Dendritic Cells Expresses IgA Fc Receptor (CD89), Which Mediates Internalization and Activation Upon Cross-Linking by IgA Complexes," The Journal of Immunology, vol. 166:346-352 (2001).
Glennie, Martin J. et al., "Preparation and Performance of Bispecific F(ab'g)2 Antibody Containing Thioether-Linked Fab'g Fragments," The Journal of Immunology, vol. 139(7):2367-2375 (1987).
Guo, Ming et al., "A Monoclonal Antibody to the DEC-205 Endocytosis Receptor on Human Dendritic Cells," Human Immunology, vol. 61:729-738 (2000).
Hawiger, Daniel et al., "Dendritic Cells Induce Peripheral T Cell Unresponsiveness Under Steady State Conditions in Vivo," J. Exp. Med., vol. 194(6):769-779 (2001).
He, Li-Zhen et al., "A Novel Human Cancer Vaccine Elicits Cellular Responses to the Tumor-Associated Antigen, Human Chorionic Gonadotropin b," Clinical Cancer Research, vol. 10:1920-1927 (2004).
He, Lizhen et al., "An Antigen Presenting Cell-Targeted Cancer Vaccine that Elicits CD4 and CD8 Effector Responses to the hCGb Tumor-Associated Antigen," Proceedings of the American Association for Cancer Research, vol. 44, 2nd ed., p. 167 (2003).
Inaba, Kayo et al., "Tissue Distribution of the DEC-205 Protein That is Detected by the Monoclonal Antibody NLDC-145, I. Expression on Dendritic Cells and Other Subsets of Mouse Leukocytes," Cellular Immunology, vol. 163:148-156 (1995).
Ishizaki, Jun et al., "Molecular Cloning of Pancreatic Group I Phospholipase A2 Receptor," The Journal of Biological Chemistry, vol. 269(8):5897-5904 (1994).
Janeway, Charles A. Jr. et al., "Localized regions of hypervariable sequence form the antigen-binding site," Immunobiology, 6th Edition, Garland Science, Chpt. 3, pp. 110-112 (2004).
Jiang, Wanping et al., "The receptor DEC-205 expressed by dendritic cells and thymic epithelial cells is involved in antigen processing," Nature, vol. 375:151-155 (1995).
Karpovsky, Boris et al., "Production of Target-Specific Effector Cells Using Hetero-Cross-Linked Aggregates Containing Anti-Target Cell and Anti-Fcg Receptor Antibodies," Journal of Experimental Medicine, vol. 160:1686-1701 (1984).
Kawakami, Yutaka et al., "The Use of Melanosomal Proteins in the Immunotherapy of Melanoma," Journal of Immunotherapy, vol. 21(4):237-246 (1998).
Klimka, A. et al., "Human anti-CD30 recombinant antibodies by guided phage antibldy selection using cell panning," British Journal of Cancer, vol. 83(2):252-260 (2000).
Kobayashi, Hiroyuki et al., "Tryptophan H33 plays an important role in pyrimidine (6-4) pyrimidone photoproduct binding by a high-affinity antibody," Protein Engineering, vol. 12(10):879-884 (1999).
Kraal, Georg et al., "Langerhans' Cells, Veiled Cells, and Interdigitating Cells in the Mouse Recognized by a Monoclonal Antibody," J. Exp. Med., vol. 163:981-997 (1986).
Lambeau, Gerard et al., "Cloning and Expression of a Membrane Receptor for Secretory Phospholipases A2," The Journal of Biological Chemistry, vol. 269(3):1575-1578 (1994).
Lamminmäki, Urpo et al., "Crystal Structure of a Recombinant Anti-estradiol Fab Fragment in Complex with 17?-Estradiol," The Journal of Biological Chemistry, vol. 276(39):36687-36694 (2001).
Liu, Margaret A. et al., "Heteroantibody duplexes target cells for lysis by cytotoxic T lymphocytes," Proc. Natl. Acad. Sci. USA, vol. 82:8648-8652 (1985).
Lonberg, Nils et al., "Antigen-specific human antibodies from mice comprising four distinct genetic modifications," Nature, vol. 368:856-859 (1994).
Lu, Lina et al., "Propagation of Dendritic Cell Progenitors from Normal Mouse Liver Using Granulocyte/Macrophage Colony-stimulating Factor and Their Maturational Development in the Presence of Type-1 Collagen," J. Exp. Med., vol. 179:1823-1834 (1994).
MacCallum, Robert M. et al., "Antibody-antigen Interactions: Contact Analysis and Binding Site Topography," J. Mol. Biol., vol. 262:732-745 (1996).

(56) References Cited

OTHER PUBLICATIONS

McKay, Paul F. et al., "The gp200-MR6 molecule which is functionally associated with the IL-4 receptor modulates B cell phenotype and is a novel member of the human macrophage mannose receptor family," Eur. J. Immunol., vol. 28:4071-4083 (1998).

McKown, Kevin M. et al., "Lack of Efficacy of Oral Bovine Type II Collagen Added to Existing Therapy in Rheumatoid Arthritis," Arthritis & Rheumatism, vol. 42 (6):1204-1208 (1999).

Mestas, Javier et al., "Of Mice and Not Men: Differences between Mouse and Human Immunology," The Journal of Immunology, vol. 172:2731-2738 (2004).

Monteiro, Renato C. et al., "Molecular Heterogeneity of Fca Receptors Detected by Receptor-Specific Monoclonal Antibodies," The Journal of Immunology, vol. 148(6):1764-1770 (1992).

Noorman, Femke et al., "Monoclonal antibodies against the human mannose receptor as a specific marker in flow cytometry and immunohistochemistry for macrophages," Journal of Leukocyte Biology, vol. 61:63-72 (1997).

Nossal, Gustav J.V., "Immunologic Tolerance," Fundamentals of Immunology, 2nd Edition, Paven Press Ltd., W.E. Paul (Ed.), Chpt. 19, pp. 571-586 (1989).

Nouri-Shirazi, Mahyar et al., "Dendritic Cells Capture Killed Tumor Cells and Present Their Antigens to Elicit Tumor-Specific Immune Response," The Journal of Immunology, vol. 165:3797-3803 (2000).

Paulus, H., "Preparation and Biomedical Applications of Bispecific Antibodies," Behring Inst. Mitt., vol. 78:118-132 (1985).

Potter, Kathleen N. et al, "Evidence for Involvement of a Hydrophobic Patch in Framework Region 1 of Human V4-34-Encoded Igs in Recognition of the Red Blood Cell I Antigen," The Journal of Immunology, vol. 169:3777-3782 (2002).

Puré, Ellen et al., "Antigen Processing by Epidermal Langerhans Cells Correlates with the Level of Biosynthesis of Major Histocompatibility Complex Class II Molecules and Expression of Invariant Chain," J. Exp. Med., vol. 172:1459-1469 (1990).

Ramakrishna, Vanky et al., "Mannose Receptor Targeting of Tumor Antigen pmel17 to Human Dendritic Cells Directs Anti-Melanoma T Cell Responses via Multiple HLA Molecules," The Journal of Immunology, vol. 172:2845-2852 (2004).

Ramakrishna, Venky et al., "Synergistic Role of TLR Agonists in T Cell-Mediated Immunity Induced by Mannose Receptor Antibody Targeting of Tumor Antigens to Human DCs," J. Immunother, vol. 28(6):658 (2005).

Ramakrishna, Venky et al., "Toll-like receptor activation enhances cell-mediated immunity induced by an antibody vaccine targeting human dendritic cells," Journal of Transitional Medicine, vol. 5:5 doi:10.1186/1479-5876-5-5 (2007).

Rocca-Serra, Jose et al., "Two monoclonal antibodies against different antigens using the same V germ-like gene," Nature, vol. 304:353-355 (1983).

Rudikoff, Stuart et al., "Single amino acid substitution altering antigen-binding specificity," Proc. Natl. Acad. Sci. USA, vol. 79:1979-1983 (1982).

Sallusto, Federica et al., "Dendritic Cells Use Macropinocytosis and the Mannose Receptor to Concentrate Macromolecules in the Major Histocompatibility Complex Class II Compartment: Downregulation by Cytokines and Bacterial Products," J. Exp. Med., vol. 182:389-400 (1995).

Schjetne, Karoline W. et al., "Delivery of Antigen to CD40 Induces Protective Immune Responses against Tumors," The Journal of Immunology, vol. 178:4169-4176 (2007).

Spack, E.G., "Antigen-specific therapies for the treatment of multiple sclerosis: a clinical trial update," Expert Opin. Investig. Drugs, vol. 6(11):1715-1727 (1997).

Steinman, Ralph M., "Dendritic cells and immune-based therapies," Experimental Hematology, vol. 24:859-862 (1996).

Steinman, Ralph M., "The Dendritic Cell System and its Role in Immunogenicity," Annu. Rev. Immunol., vol. 9:271-296 (1991).

Swiggard, William J. et al., "DEC-205, a 205-kDa Protein Abundant on Mouse Dendritic Cells and Thymic Epithelium That is Detected by the Monoclonal Antibody NLDC-145: Purification, Characterization, and N-Terminal Amino Acid Sequence," Cellular Immunology, vol. 165:302-311 (1995).

Tan, M.C. Agnes A. et al., "Mannose receptor-mediated uptake of antigens strongly enhances HLA class II-restricted antigen presentation by cultured dendritic cells," Eur. J. Immunol., vol. 27:2426-2435 (1997).

Taylor, Lisa D. et al., "A transgenic mouse that expresses a diversity of human sequence heavy and light chain immunoglobulins," Nucleic Acids Research, vol. 20(23):6287-6295 (1992).

Taylor, Maureen E. et al., "Contribution to Ligand Binding by Multiple Carbohydrate-recognition Domains in the Macrophage Mannose Receptor," The Journal of Biological Chemistry, vol. 267(3):1719-1726 (1992).

Taylor, Maureen E. et al., "Structural Requirements for High Affinity Binding of Complex Ligands by the Macrophage Mannose Receptor," The Journal of Biological Chemistry, vol. 268(1):399-404 (1993).

Tempest, Philip R. et al., "A Humanized Anti-Tumor Necrosis Factor-a Monoclonal Antibody That Acts as a Partial, Competitive Antagonist of the Template Antibody," Hybridoma, vol. 13(3):183-190 (1994).

Tjoa, Benjamin A. et al., "Development of dendritic-cell based prostate cancer vaccine," Immunology Letters, vol. 74:87-93 (2000).

Tufveson, G. et al., "New Immunosuppressants: Testing and Development in Animal Models and the Clinic: with Special Reference to DSG," Immunological Reviews, vol. 136(1):99-109 (1993).

Tüting, Thomas et al., "Autologous Human Monocyte-Derived Dendritic Cells Genetically Modified to Express Melanoma Antigens Elicit Primary Cytotoxic T Cell Responses in Vitro: Enhancement by Cotransfection of Genes Encoding the Th1-Biasing Cytokines IL-12 and IFN-a," The Journal of Immunotherapy, vol. 160:1139-1147 (1998).

Wallace, Paul K. et al., "Exogenous antigen targeted to FcgRI on Myeloid cells is presented in association with MHC class I," Journal of Immunological Methods, vol. 248:183-194 (2001).

Wang, Hui et al., "Rapid antibody responses by low-dose, single-step, dendritic cell-targeted immunization," PNAS, vol. 96(2):847-852 (2000).

Ward, E. Sally et al., "Binding activities of a repertoire of single immunoglobulin variable domains secreted from *Escherichia coli*," Nature, vol. 341:544-546 (1989).

You, Zhaoyang et al., "Targeting Dendritic Cells to Enhance DNA Vaccine Potency," Cancer Research, vol. 61:3704-3711 (2001).

Invitation to Pay Additional Fees for Application No. PCT/US2008/082745, dated Feb. 12, 2009.

International Search Report for Application No. PCT/US2008/082745, dated Jul. 8, 2009.

International Search Report and Written Opinion for Application No. PCT/US04/02725, dated Jan. 3, 2005.

International Search Report and Written Opinion for Application No. PCT/US02/36036, dated Oct. 14, 2003.

International Search Report and Written Opinion for Application No. PCT/US01/15114, dated May 23, 2002.

International Search Report and Written Opinion for Application No. PCT/US2005/027044, dated Aug. 29, 2006.

International Search Report for Application No. PCT/US96/01383, dated Jun. 12, 1996.

International Search Report and Written Opinion for Application No. PCT/US2008/082745, dated Jul. 8, 2009.

\* cited by examiner

Monocyte-derived human DCs were pulsed with FITC-3G9-2D2 or FITC-human IgG1 for 30 minutes on ice. Cells were then incubated at 37°C for the indicated periods to allow for internalization. Images were captured by confocal microscopy, and green staining revealed the presence of FITC-labeled molecules.

Human V$_H$ and V$_K$ Alignments and Germline Sequences

V$_K$ Alignments

|  | CDR1 | V | CDR2 | | CDR3 | J |
|---|---|---|---|---|---|---|
| L6 germ. | EIVLTQSPATLSLSPGERATLSC | RASQSVSSYLA | WYQQKPGQAPRLLIY | DASNRAT | GIPARFSGSGSGTDFTLTISSLEPEDFAVYYC | QQRSNWP |
| 3G9 2D2 | EIVLTQSPATLSLSPGERATLSC | RASQSVSSYLA | WYQQKPGQAPRLLIY | ASNRAT | IPARFSGSGSGTDFTLTISSLEPEDFAVYYC | QQRNWP LTFGGGTKVEIK Jк4 |
| 5A8 1F1 | EIVLTQSPATLSLSPGERATLSC | RASQSVSSYLA | WYQQKPGQAPRLLIY | ASNRAT | IPARFSGSGSGTDFTLTISSLEPEDFAVYYC | QQR THFGQGTKVEIK Jк1 |
| 3C7 3A3 | EIVLTQSPATLSLSPGERATLSC | RASQSVSSYLA | WYQQKPGQAPRLLIY | ASNRAT | IPARFSGSGSGTDFTLTISSLEPEDFAVYYC | QQR LTFGGGTKVEIK Jк4 |
| L4 germ. | AIQLTQSPSSLSASVGDRVTITC | RASQGISSALA | WYQQKPGKAPKLLIY | DASSLES | GVPSRFSGSGSGTDFTLTISSLQPEDFATYYC | QQFNSYP |
| 5C3-2-3F6 | AIQLTQSPSSLSASVGDRVTITC | RASQGISSALA | WYQQKPGKAPKLLIY | ASSLES | VPSRFSGSGSGTDFTLTISSLQPEDFATYYC | QQFNSYP HFGQGTRLFIK Jк5 |
| 3D6-4C8 | AIQLTQSPSSLSASVGDRVTITC | RASQGISSALA | WYQQKPGKAPKLLIY | ASSLES | VPSRFSGSGSGTDFTLTISSLQPEDFATYYC | QQFNSYP LTFGGGTKVEIK Jк4 |
| L15 germ. | DIQMTQSPSSLSASVGDRVTITC | RASQGISSWLA | WYQQKPEKAPKSLIY | AASSLQS | GVPSRFSGSGSGTDFTLTISSLQPEDFATYYC | QQYNSYP |
| 3D6-2F4 | DIQMTQSPSSLSASVGDRVTITC | QASQGISSWLA | WYQQKPEKAPKSLIY | ASSLQS | EVPSRFSGSGSGTDFTLTISSLQPEDFATYYC | QQYNSYP YTFGQGTKLEIK Jк2 |

V$_H$ Alignments

|  | CDR1 | V | CDR2 | | CDR3 | | J |
|---|---|---|---|---|---|---|---|
|  |  |  |  |  | D | J |  |
| 3_33 germ. | QVQLVESGGGVVQPGRSLRLSCAASGFTFS | SYGMH | WVRQAPGKGLEWVA | VIWYDGSNKYYADSVKG | RFTISRDNSKNTLYLQMNSLRAEDTAVYYCAR | | |
| 3D6 2F4 | QVQLVESGGGVVQPGRSLRLSCAASGFIFS | SYGMH | WVRQAPGKGLEWVA | VIWYDGSNKYYADSVKG | RFTISRDNSKNTLYLQMNSLRAEDTAVYYCAR | APH | FDYWGQGTLVTVSS Jн4 |
| 3D6 4C8 | QVQLVESGGGVVQPGRSLRLSCAASGFIFS | SYGMH | WVRQAPGKGLEWVA | VIWYDGSNKYYADSVKG | RFTISRDNSKNTLYLQMNSLRAEDTAVYYCAR | APH | FDYWGQGTLVTVSS Jн4 |
| 3G9 2D2 | QVQLVESGGGVVQPGRSLRLSCAASGFTFS | NYGMH | WVRQAPGKGLEWVA | VIWYDGSNKYYADSVKG | RFTISRDNSKNTLYLQMNSLRAEDTAVYYCAR | DLWGW | YFDYWGQGTLVTVSS Jн4 |
| 5A8 1F1 | QVQLVESGGGVVQPGRSLRLSCAASGFTFS | SYGMH | WVRQAPGKGLEWVA | IIWYDGSNKYYADSVKG | RFTISRDNSKNTLYLQMNSLRAEDTAVYYCAR | DF | YWYFDLWGRGTLVTVSS Jн2 |
| 3C7 3A3 | QVQLVESGGGVVQPGRSLRLSCAASGFTFS | SYNMH | WVRQAPGKGLEWVA | IIWYDGSNKYYGDSVKG | RFTISRDNSKNTLYLQMNSLRAEDTAVYYCAR | EELGIG | WYFDLWGRGTLVTVSS Jн2 |
| 5C3-2-3F6 | QVQLVESGGGVVQPGRSLRLSCAASGFTFS | SYNMH | WVRQAPGKGLEWVA | IIWYDGSNKYYGDSVKG | RFTISRDNSKNTLYLQMNSLRAEDTAVYYCAR | EELGIG | WYFDLWGRGTLVTVSS Jн2 |
| 5E12-5G1 | QVQLVESGGGVVQPGRSLRLSCAAPGKGLEWV | | | IIWYDGSNKYYADSVKG | RFTISRDNSKNTLYLQMNSLRAEDTAVYYCAR | GPFR | YFDIWGRGTLVTVSS Jн2 |
| 3rpt-HC16 germ. | EVQLVQSGGGLVHPGGSLRLSCAASGFTFS | SYAMH | WVRQAPGKGLEWV | SAIGIGGGIYYADS... | RFTISRDNAKNSLYLQMNSLRAEDMAVYYCAR | | |
| 2D3-1F3-2A9 | EVQLVQSGGGLVHPGGSLRLSCAGSGFTFS | SYAMH | WVRQAPGKGLEWV | STICTGGGTPYADSVKG | RFTISRDNAKNSLYLQMNSLRAEDMAVYYCAL | S | AFLYWGQGTMVTVSS Jн3 |
| 1F6-3C10 | EVQLVQSGGGLVHPGGSLRLSCAGSGFTFS | SYAMH | WVRQAPGKGLEWV | SAIGIGGYIYYDSVKG | RFTISRDNAKKSLYLQMNSLRAEDMAVYYCAR | EPFYILTGYSP (D3-9) | YFDYWGQGTLVTVSS Jн4 |

Fig. 5

Human V_H CDR Consensus Sequences

```
3D6-2F4  VH CDR1 (SEQ ID NO:5):    IYGMH
3D6-4C8  VH CDR1 (SEQ ID NO:17):   IYGMH
3G9-2D2  VH CDR1 (SEQ ID NO: 29):  NYGMY
5A8-1F1  VH CDR1 (SEQ ID NO: 41):  TYGMH
3C7-3A3, VH CDR1 (SEQ ID NO: 53):  SYNMH
2D3-1F5-2A9, VH CDR1 (SEQ ID NO: 65):  NYAMH
1E6-3D10 VH CDR1: (SEQ ID NO: 7-): SYAMH
5C3-2-3F6 VH CDR1 (SEQ ID NO: 77): SYNMH
5D12-5G1 VH CDR1 (SEQ ID NO: 89): SYGMH

VH CDR1 CONSENSUS (SEQ ID NO: 97):  (I,N,T,S) Y (G,N,A) M (H,Y)

3D6-2F4  VH CDR2 (SEQ ID NO: 6):   VIWYDGSNKYYADSVKG
3D6-4C8  VH CDR2 (SEQ ID NO: 18):  VIWYDGSNKYYADSVKG
3G9-2D2, VH CDR2 (SEQ ID NO: 30):  VIWYDGSNKYYADSVKG
5A8-1F1, VH CDR2 (SEQ ID NO: 42):  IIWDGGNKYYADSVKG
3C7-3A3, VH CDR2 (SEQ ID NO: 54):  FIWYDGSNKYYGDSVKG
2D3-1F5-2A9, VH CDR2 (SEQ ID NO: 66):  TIGTGGTPYA-DSVKG
1E6-3D10 VH CDR2 (SEQ ID NO: 72):  AIGTGGYYYV-DSVKG
5C3-2-3F6 VH CDR2 (SEQ ID NO: 78): VIWYGSNKYYGDSVKG
5D12-5G1 VH CDR2 (SEQ ID NO: 90):  VIWYDGSNKYYADSVKG

VH CDR2 CONSENSUS (SEQ ID NO: 98): (V,I,F,T,A) I (W,G) (Y,T) (D,G)
G (S,G,Y) (N,T) (K,P) Y (Y,A,V) (A,G,-) D S V K G

3D6-2F4  VH CDR3 (SEQ ID NO: 7):   APHFDY
3D6-4C8  VH CDR3 (SEQ ID NO: 19):  APHFDY
3G9-2D2, VH CDR3 (SEQ ID NO: 31):  DLWGWYFDY
5A8-1F1, VH CDR3 (SEQ ID NO: 43):  DFYWYFDL
3C7-3A3, VH CDR3 (SEQ ID NO: 55):  EELGIGWYFDL
2D3-1F5-2A9, VH CDR3 (SEQ ID NO: 67):  SAFDV
1E6-3D10 VH CDR3 (SEQ ID NO: 73):  EPFYDILIGYSPYFDY
5C3-2-3F6 VH CDR3 (SEQ ID NO: 79): EELGIGWYFDL
5D12-5G1 VH CDR3 (SEQ ID NO: 91):  GPPRYFDL

VH CDR3 (CORE) CONSENSUS (SEQ ID NO: 99): (A,G,Y,S,P,-) (P,W,S,R) (Y,A,H) F D (Y,L,V)
(Where "-" denotes option of no amino acid residue present at that position)
```

*Fig. 6*

Human V_L CDR Consensus Sequences

```
3D6-2F4  VL CDR1 (SEQ ID NO: 11):    RASQGISSWLA
3D6-4C8  VL CDR1 (SEQ ID NO: 23):    RASQGISSALA
3G9-2D2, VL CDR1 (SEQ ID NO: 35):    RASQSVSSYLA
5A8-1F1, VL CDR1 (SEQ ID NO: 47):    RASQSVSSYLA
3C7-3A3, VL CDR1 (SEQ ID NO: 59):    RASQSVSSYLA
5C3-2-3F6 VL CDR1 (SEQ ID NO: 83):   RASQGISSALA

VL CDR1 CONSENSUS (SEQ ID NO: 100):  R A S Q (S,G) (I,V) S S (Y,W,A) L A

3D6-2F4  VL CDR2 (SEQ ID NO: 12):    AASSLQS
3D6-4C8  VL CDR2 (SEQ ID NO: 24):    DASSLES
3G9-2D2, VL CDR2 (SEQ ID NO: 36):    DASNRAT
5A8-1F1, VL CDR2 (SEQ ID NO: 48):    DASNRAT
3C7-3A3, VL CDR2 (SEQ ID NO: 60):    DASNRAT
5C3-2-3F6 VL CDR2 (SEQ ID NO: 84):   DASSLES

VL CDR2 CONSENSUS (SEQ ID NO: 101):  (D,A) A S (N,S) (R,L) (A,Q,E) (T,S)

3D6-2F4  VL CDR3 (SEQ ID NO: 13):    QQYNSYPYT
3D6-4C8  VL CDR3 (SEQ ID NO: 25):    QQFNSYPLT
3G9-2D2, VL CDR3 (SEQ ID NO: 37):    QQRRNWPLT
5A8-1F1, VL CDR3 (SEQ ID NO: 49):    QQRRT----
3C7-3A3, VL CDR3 (SEQ ID NO: 61):    QQRRT----
5C3-2-3F6 VL CDR3 (SEQ ID NO: 85):   QQFNSYPH-

VL CDR3 CONSENSUS (SEQ ID NO: 102):  Q Q (R,Y,F) (R,N) (T,S,N) (Y,W,-) (P,-) (Y,L,H,-) (T,-)
```

(Where "-" denotes option of no amino acid residue present at that position)

Fig. 7

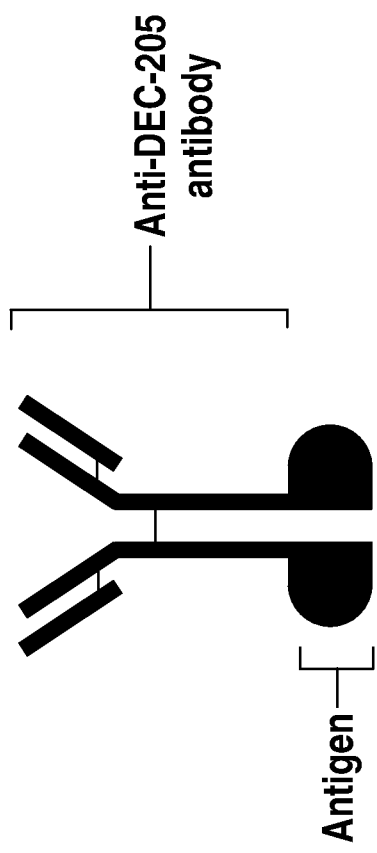

ANTIBODIES THAT BIND HUMAN DENDRITIC AND EPITHELIAL CELL 205 (DEC-205)

RELATED APPLICATIONS

The application is a divisional of U.S. patent application Ser. No. 12/266,745, filed on Nov. 7, 2008, now allowed, which claims priority to U.S. Provisional Application No. 61/002,253, filed on Nov. 7, 2007 and U.S. Provisional Application No. 61/191,551, filed on Sep. 10, 2008, the contents of which are incorporated herein by reference.

BACKGROUND OF THE INVENTION

Dendritic cells (DCs) are specialized cells of the immune system. DCs have the unique capacity for initiating primary and secondary T and B lymphocyte responses by presenting antigens in the form of peptides bound to cell-surface major histocompatibility complex (MHC) molecules. The antigen-presentation function of dendritic cells has been correlated with the high-level expression of human dendritic and epithelial cell 205 receptor (DEC-205) (Jiang et al. (1995) Nature 375(11)151).

DEC-205 is an endocytic receptor found primarily on dendritic cells, but is also found on B cells, brain capillaries, bone marrow stroma, epithelia of intestinal villi and pulmonary airways, as well as the cortical epithelium of the thymus and the dendritic cells in the T cell areas of peripheral lymphoid organs. DEC-205 is expressed at high levels on DCs in the T cell areas of lymphoid organs (Kraal et al. (1986) *J. Exp. Med.* 163:981; Witmer-Pack et al. (1995) *Cell. Immunol.* 163:157). DEC-205 has ten membrane-external, contiguous C-type lectin domains (Id.; Mahnke et al. (2000) *J. Cell Biol.* 151:673) which mediate the efficient processing and presentation of antigens on MHC class II products in vivo (Hawiger et al. (2001) *J. Exp. Med.* 194:769). It has been shown that small amounts of injected antigen, targeted to DCs by the DEC-205 adsorptive pathway, are able to induce solid peripheral CD8+ T cell tolerance (Bonifaz et al. (2002) *J. Exp. Med.* 196(12): 1627).

Despite recent advances in the characterization of dendritic cells, very little is known regarding dendritic cell-specific receptors, such as DEC-205, and few reagents are available which are specific to dendritic cells. Reagents, in particular antibodies, which react specifically or preferentially with dendritic cells, such as through DEC-205, have great potential as targeting agents to induce potent immune responses to tumor or infectious disease antigens. These cell-specific targeting agents could also be engineered to deliver toxins to eliminate potent antigen presenting cells (e.g., dendritic cells) in bone marrow and organ transplantations or other autoimmune disorders. Accordingly, such dendritic cell-specific binding agents possess great therapeutic and diagnostic value.

SUMMARY OF THE INVENTION

The present invention provides isolated antibodies, e.g., human antibodies, which bind to human DEC-205 and exhibit particular properties. The present invention also provides vaccine conjugates, bispecific molecules, and therapeutic compositions containing such antibodies. Accordingly, the antibodies and compositions of the invention can be used in a variety of dendritic cell-targeted therapies, for example, to enhance antigen presentation and/or induce T cell responses, such as cytotoxic T cell (CTL) responses, against a variety of target cells or pathogens, or to treat antigen presenting cell (APC)-mediated diseases.

In one embodiment, the antibodies of the present invention exhibit one or more of the following properties: (1) binding to human DEC-205 with an affinity constant of at least $10^8 M^{-1}$ as measured by surface plasmon resonance; (2) internalization after binding to human dendritic cells expressing DEC-205; (3) generation or enhancement of human T-cell responses, e.g., CD4+ and CD8+ (CTL) T-cell responses to an antigen (which may be linked to the antibody), suitably mediated by either MHC Class I and/or Class II pathways; and (4) inducement of peripheral $CD8^+$ T cell tolerance. Furthermore, the antibodies may cross-react with DEC-205 on non-human primate dendritic cells or those of other species. Still further, the antibodies may suitably exhibit one or more of additional properties including for example: (1) selectively bind to an epitope located on the extracellular domain of human DEC-205, for example, on one or a combination of the cysteine rich domain, the FnII domain, or one or more of the ten C-type lectin-like domains; and (2) localization to antigen processing compartments in the cell.

Particular examples of antibodies of the invention comprise heavy and light chain variable regions that utilize particular human germlines, i.e., are encoded by the germline genes, but include genetic rearrangements and mutations, e.g., somatic mutations, which occur during antibody maturation. In one embodiment, the heavy chain variable region of the antibodies of the present invention utilizes a human germline $V_H$ 3-33 gene and comprises at least one of the amino acid substitutions in any one of SEQ ID NOS: 4, 16, 28, 40, 52, 76 and 88 as compared to SEQ ID NO: 95. Alternatively, the heavy chain variable region utilizes a human germline Orph-C16 gene and comprises at least one of the amino acid substitutions in either of SEQ ID NOS: 64 and 70 as compared to SEQ ID NO: 96.

In another embodiment, the light chain variable region of the antibody is selected from the group consisting of a region that (a) utilizes a human germline VK1-L15 gene and comprises at least one of the amino acid substitutions in SEQ ID NO: 10 as compared to SEQ ID NO: 94; (b) utilizes a human germline VK1-L4 gene and comprises at least one of the amino acid substitutions in any one of SEQ ID NOs: 22 or 82 as compared to SEQ ID NO: 93; or (c) utilizes a human germline VK3-L6 gene and comprises at least one of the amino acid substitutions in any one of SEQ ID NOs: 34, 46, 58, as compared to SEQ ID NO: 92.

In another embodiment, the heavy chain variable region CDR3 sequence is selected from the group consisting of SEQ ID NOs: 7, 19, 31, 43, 55, 67, 73, 79, 91 and conservative sequence modifications thereof (e.g., conservative amino acid substitutions). The antibodies may further include a light chain variable region CDR3 sequence selected from the group consisting of SEQ ID NOs: 13, 25, 37, 49, 61, 85, and conservative sequence modifications thereof. In another embodiment, the heavy chain CDR2 and CDR1 sequences are selected from SEQ ID NOs: 6, 18, 30, 42, 54, 66, 72, 78, 90 and SEQ ID NOs: 5, 17, 29, 41, 53, 65, 71, 77, 89, respectively, and conservative sequence modifications thereof. The light chain CDR2 and CDR1 sequences are selected from SEQ ID NOs: 12, 24, 36, 48, 60, 84, and SEQ ID NOs: 11, 23, 35, 47, 59, 83, respectively, and conservative sequence modifications thereof.

In still another embodiment, the invention provides an isolated antibody that binds DEC-205 and includes heavy and light chain variable region CDR1, CDR2 and CDR3 sequences selected from the group consisting of:

(i) a heavy chain variable region CDR1 comprising SEQ ID NO: 5;
a heavy chain variable region CDR2 comprising SEQ ID NO: 6;
a heavy chain variable region CDR3 comprising SEQ ID NO: 7;
a light chain variable region CDR1 comprising SEQ ID NO: 11;
a light chain variable region CDR2 comprising SEQ ID NO: 12;
a light chain variable region CDR3 comprising SEQ ID NO: 13; or
conservative sequence modifications thereof;

(ii) a heavy chain variable region CDR1 comprising SEQ ID NO: 17;
a heavy chain variable region CDR2 comprising SEQ ID NO: 18;
a heavy chain variable region CDR3 comprising SEQ ID NO: 19;
a light chain variable region CDR1 comprising SEQ ID NO: 23;
a light chain variable region CDR2 comprising SEQ ID NO: 24;
a light chain variable region CDR3 comprising SEQ ID NO: 25; or
conservative sequence modifications thereof;

(iii) a heavy chain variable region CDR1 comprising SEQ ID NO: 29;
a heavy chain variable region CDR2 comprising SEQ ID NO: 30;
a heavy chain variable region CDR3 comprising SEQ ID NO: 31;
a light chain variable region CDR1 comprising SEQ ID NO: 35;
a light chain variable region CDR2 comprising SEQ ID NO: 36;
a light chain variable region CDR3 comprising SEQ ID NO: 37; or
conservative sequence modifications thereof;

(iv) a heavy chain variable region CDR1 comprising SEQ ID NO: 41;
a heavy chain variable region CDR2 comprising SEQ ID NO: 42;
a heavy chain variable region CDR3 comprising SEQ ID NO: 43;
a light chain variable region CDR1 comprising SEQ ID NO: 47;
a light chain variable region CDR2 comprising SEQ ID NO: 48;
a light chain variable region CDR3 comprising SEQ ID NO: 49; or
conservative sequence modifications thereof;

(v) a heavy chain variable region CDR1 comprising SEQ ID NO: 53;
a heavy chain variable region CDR2 comprising SEQ ID NO: 54;
a heavy chain variable region CDR3 comprising SEQ ID NO: 55;
a light chain variable region CDR1 comprising SEQ ID NO: 59;
a light chain variable region CDR2 comprising SEQ ID NO: 60;
a light chain variable region CDR3 comprising SEQ ID NO: 61; or
conservative sequence modifications thereof;

(vi) a heavy chain variable region CDR1 comprising SEQ ID NO: 77;
a heavy chain variable region CDR2 comprising SEQ ID NO: 78;
a heavy chain variable region CDR3 comprising SEQ ID NO: 79;
a light chain variable region CDR1 comprising SEQ ID NO: 83;
a light chain variable region CDR2 comprising SEQ ID NO: 84;
a light chain variable region CDR3 comprising SEQ ID NO: 85; or
conservative sequence modifications thereof.

For example, the isolated antibody binds to human DEC-205 and comprises:
a heavy chain variable region CDR1 comprising SEQ ID NO: 29
a heavy chain variable region CDR2 comprising SEQ ID NO: 30
a heavy chain variable region CDR3 comprising SEQ ID NO: 31
a light chain variable region CDR1 comprising SEQ ID NO: 35;
a light chain variable region CDR2 comprising SEQ ID NO: 36; and
a light chain variable region CDR3 comprising SEQ ID NO: 37.

In another embodiment, the heavy chain variable region CDR3 sequence comprises an amino acid sequence selected from the consensus sequence: (A,G,Y,S,P,-) (P,W,S,R) (Y,A,H) F D (Y,L,V) (SEQ ID NO: 99), wherein "-" denotes the option of no amino acid residue being present at that consensus position. The antibodies may further include a light chain variable region CDR3 sequence comprising an amino acid sequence selected from the consensus sequence: Q Q (R,Y,F) (R,N) (T,S,N) (Y,W,-) (P,-) (Y,L,H,-) (T,-) (SEQ ID NO: 102), wherein "-" denotes the option of no amino acid residue being present at that consensus position. In another embodiment, the heavy chain variable region CDR2 sequence comprises an amino acid sequence selected from the consensus sequence: (V,I,F,T,A) I (W,G) (Y,T) (D,G) G (S,G,Y) (N,T) (K,P) Y (Y,A,V) (A,G,-) D S V K G (SEQ ID NO: 98), wherein "-" denotes the option of no amino acid residue being present at that consensus position, and the light chain variable region CDR2 sequence comprises an amino acid sequence selected from the consensus sequence: (D,A) A S(N,S) (R,L) (A,Q,E) (T,S) (SEQ ID NO: 101). In another embodiment, the heavy chain variable region CDR1 sequence comprises an amino acid sequence selected from the consensus sequence: (I,N,T,S) Y (G,N,A) M (H,Y) (SEQ ID NO: 97); and the light chain variable region CDR1 sequence comprises an amino acid sequence selected from the consensus sequence: R A S Q (S,G) (I,V) S S (Y,W,A) L A (SEQ ID NO: 100).

In still another embodiment, the invention provides an isolated antibody that binds DEC-205 and includes heavy and light chain variable region CDR1, CDR2 and CDR3 sequences comprising:

(i) a heavy chain variable region CDR1 comprising an amino acid sequence selected from the consensus sequence: (I,N,T,S) Y (G,N,A) M (H,Y) (SEQ ID NO: 97);
(ii) a heavy chain variable region CDR2 comprising an amino acid sequence selected from the consensus sequence: (V,I,F,T,A) I (W,G) (Y,T) (D,G) G (S,G,Y) (N,T) (K,P) Y (Y,A,V) (A,G,-) D S V K G (SEQ ID NO: 98);

(iii) a heavy chain variable region CDR3 comprising an amino acid sequence selected from the consensus sequence: (A,G,Y,S,P,-) (P,W,S,R) (Y,A,H) F D (Y,L,V) (SEQ ID NO: 99);

(iv) a light chain variable region CDR1 comprising an amino acid sequence selected from the consensus sequence: RAS Q (S,G) (I,V) S S (Y,W,A) L A (SEQ ID NO: 100);

(v) a light chain variable region CDR2 comprising an amino acid sequence selected from the consensus sequence: (D,A) A S(N,S) (R,L) (A,Q,E) (T,S) (SEQ ID NO: 101); and (vi) a light chain variable region CDR3 comprising an amino acid sequence selected from the consensus sequence: Q Q (R,Y,F) (R,N) (T,S,N) (Y,W,-) (P,-) (Y,L,H,-) (T,-) (SEQ ID NO: 102), wherein "-" denotes the option of no amino acid residue being present at that consensus position.

In another embodiment, isolated antibodies of the invention bind to human DEC-205 and include a heavy chain variable region including an amino acid sequence selected from the group consisting of SEQ ID NOs: 4, 16, 28, 40, 52, 64, 70, 76, 88 and conservative sequence modifications thereof. The antibody may further include a light chain variable region including an amino acid sequence selected from the group consisting of SEQ ID NOs: 10, 22, 34, 46, 58, 82, and conservative sequence modifications thereof.

In a still further embodiment, isolated antibodies of the invention bind to human DEC-205 and include a heavy chain variable region and a light chain variable region including the amino acid sequences selected from the group consisting of:

(a) SEQ ID NOs:4 and 10, respectively, and conservative sequence modifications thereof;

(b) SEQ ID NOs: 16 and 22, respectively, and conservative sequence modifications thereof;

(c) SEQ ID NOs: 28 and 34, respectively, and conservative sequence modifications thereof;

(d) SEQ ID NOs: 40 and 46, respectively, and conservative sequence modifications thereof;

(e) SEQ ID NOs: 52 and 58, respectively, and conservative sequence modifications thereof; and (f) SEQ ID NOs: 76 and 82, respectively, and conservative sequence modifications thereof.

Isolated antibodies which include heavy and light chain variable regions having at least 80%, or at least 85%, or at least 90%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention.

In another embodiment, the isolated antibody binds to human DEC-205 and includes a heavy chain variable region comprising an amino acid sequence selected from the group consisting of SEQ ID NOs: 4, 16, 28, 40, 52, 64, 70, 76, 88 or sequences where at least one amino acid residue in the framework region of the heavy chain variable region is substituted with the corresponding germline residue. The antibody may further include a light chain variable region comprising an amino acid sequence selected from the group consisting of SEQ ID NOs: 10, 22, 34, 46, 58, 82, or sequences where at least one amino acid residue in framework region of the light chain variable region is substituted with the corresponding germline residue. The substituted amino acid residue can include: a residue that non-covalently binds antigen directly; a residue adjacent to a CDR; a CDR-interacting residue; a residue participating in the VL-VH interface, a canonical residue, a vernier zone residue, or an interchain packing residue.

Also encompassed by the present invention are isolated antibodies which compete for binding to DEC-205 with the antibodies of the invention.

The antibodies of the invention can either be full-length, for example, any of the following isotypes: IgG1, IgG2, IgG3, IgG4, IgM, IgA1, IgA2, IgAsec, IgD, and IgE. Alternatively, the antibodies can be fragments such as an antigen-binding portion or a single chain antibody (e.g., a Fab, F(ab')$_2$, Fv, a single chain Fv fragment, an isolated complementarity determining region (CDR) or a combination of two or more isolated CDRs).

The invention also provides a molecular conjugate comprising an antibody of the invention linked to an antigen (including fragments, epitopes and antigenic determinants), such as component of a pathogen, a tumor antigen or an autoantigen. For example, the antigen may include a tumor antigen, such as βhCG, gp100 or Pmel17, CEA, gp100, TRP-2, NY-BR-1, NY-CO-58, MN (gp250), idiotype, Tyrosinase, Telomerase, SSX2, MUC-1, MAGE-A3, and high molecular weight-melanoma associated antigen (HMW-MAA) MART1, melan-A, NY-ESO-1, MAGE-1, MAGE-3, WT1, Her2, mesothelin or high molecular weight-melanoma associated antigen (HMW-MAA).

The term "tumor antigen" as used herein preferably means any antigen or antigenic determinant which is present on (or associated with) a tumor cell and not typically on normal cells, or an antigen or antigenic determinant which is present on or associated with tumor cells in greater amounts than on normal (non-tumor) cells, or an antigen or antigenic determinant which is present on tumor cells in a different form than that found on normal (non-tumor) cells. The term thus includes tumor-specific antigens including tumor-specific membrane antigens, tumor-associated antigens, including tumor-associated membrane antigens, embryonic antigens on tumors, growth factor receptors, growth factor ligands, and any other type of antigen that is associated with cancer. A tumor antigen may be, for example, an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen.

The term "fragment" refers to an amino acid sequence that is a portion of a full-length protein or polypeptide, for example between about 8 and about 1500 amino acids in length, suitably between about 8 and about 745 amino acids in length, suitably about 8 to about 300, for example about 8 to about 200 amino acids, or about 10 to about 50 or 100 amino acids in length.

In another embodiment, the molecular complex further includes a therapeutic agent, such as a cytotoxic agent, an immunosuppressive agent, or a chemotherapeutic agent.

The invention also provides a bispecific molecule comprising an antibody of the invention linked to a second functional moiety having a different binding specificity than said antibody.

Compositions including an antibody, a molecular conjugate or a bispecific molecule described herein, and a pharmaceutically effective carrier, are also provided. The compositions may further include a therapeutic agent (e.g., an immunosuppressive agent or an antibody different from an antibody of the invention).

Nucleic acid molecules encoding the antibodies of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

In another embodiment, the present invention provides methods for targeting an antigen to a cell, e.g., a cell capable of antigen presentation (such as peripheral blood mononuclear cells (PBMC), monocytes (such as THP-1), B lymphoblastoid cells (such as C1R.A2, 1518 B-LCL) and monocyte-derived DCs in a subject by administering a molecule which binds a receptor on the cell (e.g., the previously described DEC-205 antibodies) linked to an antigen. In one embodiment the targeted cell (which may be a B-cell) stimulates MHC Class I restricted T-cells.

The antibodies and other compositions of the present invention can also be used to induce or enhance an immune response (e.g., a T cell-mediated immune response) against an antigen in a subject. Accordingly, in one embodiment, the present invention provides a method for inducing or enhancing a CTL response against an antigen by forming a conjugate of the antigen and a antibody which binds to a receptor on an antigen presenting cell, e.g., human DEC-205. The conjugate is then contacted, either in vivo or ex vivo, with cells expressing human DEC-205 such that the antigen is internalized, processed and presented to T cells in a manner which induces or enhances a CTL response (e.g., a response mediated by $CD8^+$ cytotoxic T cells) against the antigen. In another embodiment, this serves also to induce a helper T cell response (e.g., a response mediated by $CD4^+$ helper T cells) against the antigen. Thus, the immune response may be induced through both MHC class I and MHC class II pathways. The cells expressing DEC-205 can also be contacted with an adjuvant, a cytokine which stimulates proliferation of dendritic cells, and/or an immunostimulatory agent to further enhance the immune response.

In another embodiment, methods of detecting the presence of DEC-205, or a cell expressing DEC-205, in a sample are provided by: (a) contacting the sample with the antibody of the invention under conditions that allow for formation of a complex between the antibody and DEC-205; and (b) detecting the formation of a complex between the antibody and DEC-205 in the sample.

Also within the scope of the invention are kits comprising the compositions (e.g., antibodies, molecular conjugates, multispecific and bispecific molecules) of the invention and, optionally, instructions for use. The kit can further contain a least one additional reagent, such as a cytokine or complement, or one or more additional human antibodies of the invention (e.g., a human antibody having a complementary activity which binds to an epitope on dendritic cells distinct from the first human antibody).

Other features and advantages of the instant invention will be apparent from the following detailed description and claims.

BRIEF DESCRIPTION OF THE DRAWINGS

FIG. 5 is an alignment of human VH and VK Germline Sequences with VH and VK sequences of anti-DEC-205 antibodies (3D6-2F4, 3D6-4C8, 3G9-2D2, 5A8-1F1, 2D3-1F5-2A9, 3C7-3A3, 5C3-2-3F6, 1E6-3D10). Figure discloses SEQ ID NOS 92, 34, 46, 58, 93, 82, 22, 94, 10, 95, 4, 16, 103-105, 76, 88, 96, 106 and 70, respectively, in order of appearance.

FIG. 6 shows alignments of VH CDR1, CDR2 and CDR3 sequences of human anti-DEC-205 antibodies (3D6-2F4, 3D6-4C8, 3G9-2D2, 5A8-1F1, 3C7-3A3, 2D3-1F5-2A9, 1E6-3D10, 5C3-2-3F6, 5D12-5G1).

FIG. 7 shows alignments of human anti-DEC-205 HuMab VK CDR1, CDR2 and CDR3 sequences of human anti-DEC-205 antibodies (3D6-2F4, 3D6-4C8, 3G9-2D2, 5A8-1F1, 3C7-3A3, 5C3-2-3F6).

FIG. 8 shows a schematic representation of an example of an anti-DEC-205/antigen fusion APC targeted vaccine construct.

DETAILED DESCRIPTION OF THE INVENTION

Figure 1:
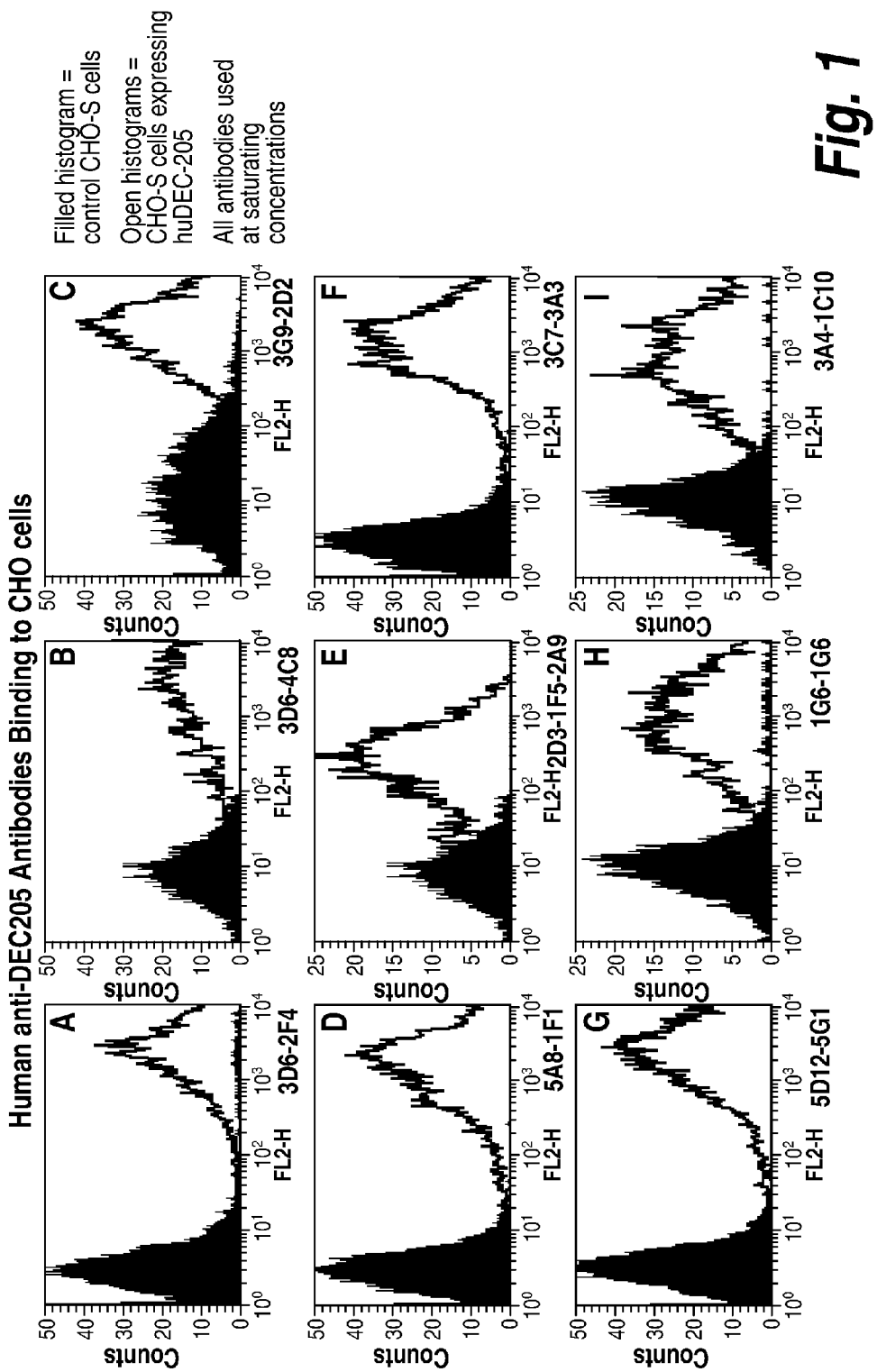
FIGS. 1A-1I include graphs showing the binding of human anti-DEC-205 antibodies (3D6-2F4, 3D6-4C8, 3G9-2D2, 5A8-1F1, 2D3-1F5-2A9, 3C7-3A3, 5D12-5G1, 1G6-1G6 and 3A4-1C10) to CHO-S cells expressing human DEC-205 by fluorescence analysis using a LSR™ instrument (BD Biosciences, NJ, USA).

The present invention provides antibodies (e.g., human antibodies) which bind to human DEC-205. In certain embodiments, the antibodies exhibit a variety of functional properties, e.g., binding to human DEC-205 with an affinity constant of at least $10^8$ $M^{-1}$ as measured by surface plasmon resonance, internalization after binding to human dendritic cells expressing DEC-205, generating or enhancing human T-cell responses, for example CD4+ or CD8+ (CTL) or NKT cell responses, to an antigen which may be linked to the antibody, e.g., CTL responses mediated by both MHC Class I and Class II pathways; localization to antigen processing compartments in dendritic cells; inducement of peripheral $CD8^+$ T cell tolerance; or cross-reaction with DEC-205 on non-human primate dendritic cells or those of other species. In other embodiments, the antibodies include heavy and light chain variable regions which utilize particular human germline genes and include particular structural features such as, particular CDR sequences. The invention further provides methods of making such antibodies, molecular conjugates and bispecific molecules including such antibodies, as well as compositions containing the antibodies. The invention also provides methods of targeting antigens to antigen presenting cells (e.g., peripheral blood mononuclear cells (PBMC), monocytes (such as THP-1), B lymphoblastoid cells (such as C1R.A2, 1518 B-LCL) and monocyte-derived DCs either in vitro or in vivo, for example, by using the anti-DEC-205 antibodies of the present invention. Methods of the present invention also include methods of inducing and enhancing an immune response (e.g., a T cell-mediated immune response) against an antigen in a subject. Such methods include the presentation of the antigen via a receptor on an antigen presenting cell (e.g., DEC-205) as a component of an MHC-I and/or MHC-II conjugate (e.g., the T cell response is mediated by both CD4+ and CD8+ T cells or by cytotoxic T cells or helper T cells). In one embodiment the targeted cell (which may be a B-cell) stimulates MHC Class I restricted T-cells.

In order that the present invention may be more readily understood, certain terms are first defined. Additional definitions are set forth throughout the detailed description.

The term "human Dendritic and Epithelial Cell 205 receptor" (DEC-205) includes any variants or isoforms of DEC-205 which are naturally expressed by cells (e.g., human DEC-205 deposited with GENBANK® having accession no. AAC17636, and mouse DEC-205 deposited with GEN-BANK® having accession no. AAL81722). Accordingly, human antibodies of the invention may cross-react with DEC-205 from species other than human. Alternatively, the antibodies may be specific for human DEC-205 and may not exhibit any cross-reactivity with other species. DEC-205 or any variants and isoforms thereof, may either be isolated from cells or tissues which naturally express them (e.g. human, mouse and cynomologous monkey cells) or be recombinantly produced using well-known techniques in the art and/or those described herein.

Genbank® (Accession No. AAC17636A) reports the amino acid sequence of human DEC-205 as follows (SEQ ID NO:1):

```
   1 mrtgwatprr pagllmllfw ffdlaepsgr aandpftivh gntgkcikpv ygwivaddcd
  61 etedklwkwv sqhrlfhlhs qkclglditk svnelrmfsc dssamlwwkc ehhslygaar
 121 yrlalkdghg taisnasdvw kkggseeslc dqpyheiytr dgnsygrpce fpflidgtwh
 181 hdcildedhs gpwcattlny eydrkwgicl kpengcednw ekneqfgscy qfntqtalsw
 241 keayvscqnq gadllsinsa aeltylkeke giakifwigl nqlysargwe wsdhkplnfl
 301 nwdpdrpsap tiggsscarm daesglwqsf sceaqlpyvc rkplnntvel tdvwtysdtr
 361 cdagwlpnng fcyllvnesn swdkahakck afssdlisih sladvevvvt klhnedikee
 421 vwiglknini ptlfqwsdgt evtltywden epnvpynktp ncvsylgelg qwkvqsceek
 481 lkyvckrkge klndassdkm cppdegwkrh getcykiyed evpfgtncnl titsrfeqey
 541 lndlmkkydk slrkyfwtgl rdvdscgeyn watvggrrra vtfsnwnfle paspggcvam
 601 stgksvgkwe vkdcrsfkal sickkmsgpl gpeeaspkpd dpcpegwqsf paslscykvf
 661 haerivrkrn weeaerfcqa lgahlssfsh vdeikeflhf ltdqfsgqhw lwiglnkrsp
 721 dlqgswqwsd rtpvstiimp nefqqdydir dcaavkvfhr pwrrgwhfyd drefiylrpf
 781 acdtklewvc qipkgrtpkt pdwynpdrag ihgppliieg seywfvadlh lnyeeavlyc
 841 asnhsflati tsfvglkaik nkianisgdg qkwwirisew piddhftysr ypwhrfpvtf
 901 geeclymsak twlidlgkpt dcstklpfic ekynvsslek yspdsaakvq cseqwipfqn
 961 kcflkikpvs ltfsqasdtc hsyggtlpsv lsqieqdfit sllpdmeatl wiglrwtaye
1021 kinkwtdnre ltysnfhpll vsgrlripen ffeeesryhc alilnlqksp ftgtwnftsc
1081 serhfvslcq kysevksrqt lqnasetvky lnnlykiipk tltwhsakre clksnmqlvs
1141 itdpyqqafl svqallhnss lwiglfsqdd elnfgwsdgk rlhfsrwaet ngqledcvvl
1201 dtdgfwktvd cndnqpgaic yysgneteke vkpvdsvkcp spvlntpwip fqnccynfii
1261 tknrhmattq devhtkcqkl npkshilsir dekennfvle qllyfnymas wvmlgityrn
1321 nslmwfdktp lsythwragr ptiknekfla glstdgfwdi qtfkvieeav yfhqhsilac
1381 kiemvdykee hnttlpqfmp yedgiysviq kkvtwyealn mcsqsgghla svhnqngqlf
1441 ledivkrdgf plwvglsshd gsessfewsd gstfdyipwk gqtspgncvl ldpkgtwkhe
1501 kcnsvkdgai cykptkskkl srltyssrcp aakengsrwi qykghcyksd qalhsfseak
1561 klcskhdhsa tivsikdede nkfvsrlmre nnnitmrvwl glsqhsvdqs wswldgsevt
1621 fvkwensksk gvgrcsmlia snetwkkvec ehgfgrvvck vplgpdytai aiivatlsil
1681 vlmggliwfl fqrhrlhlag fssvryaqgv nedeimlpsf hd
```

The major domains of human DEC-205 can be represented as follows:
N-CR-FNII-CTLD1-CTLD2-CTLD3-CTLD4-CTLD5-CTLD6-CTLD7-CTLD8-CTLD9-CTLD10-TMC
Where N is the N-terminus, CR represents the "Cys Rich" domain, FNII represents the "Fibronectin Type II" domain, CTLD1 to CTLD10 represent the ten "C-Type Lectin-Like" domains and TMC represents the transmembrane and cytoplasmic domains.

The term "dendritic cell" as used herein, includes immature and mature dendritic cells and related myeloid progenitor cells that are capable of differentiating into dendritic cells, or related antigen presenting cells (e.g., monocytes and macrophages) in that they express antigens in common with dendritic cells. As used herein, the term "related" includes a cell that is derived from a common progenitor cell or cell lineage. In one embodiment, binding of an antibody of the invention to dendritic cells mediates an effect on dendritic cell growth and/or function by targeting molecules or cells with defined functions (e.g., tumor cells, effector cells, microbial pathogens) to dendritic cells. In a further embodiment, binding of an antibody of the invention to a dendritic cell results in internalization of the antibody by the dendritic cell.

"MHC molecules" include two types of molecules, MHC class I and MHC class II. MHC class I molecules present antigen to specific $CD8^+$ T cells and MHC class II molecules present antigen to specific $CD4^+$ T cells. Antigens delivered exogenously to APCs are processed primarily for association with MHC class II. In contrast, antigens delivered endogenously to APCs are processed primarily for association with MHC class I. However, under specific conditions, DCs have the unique capacity to allow exogenous antigens access to internal compartments for binding to MHC class I molecules, in addition to MHC class II molecules. This process is called "cross-priming" or "cross-presentation."

As used herein, the term "immunostimulatory agent" refers to compounds capable of stimulating APCs, such as DCs and macrophages. For example, suitable immunostimulatory agents for use in the present invention are capable of stimulating APCs so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-1β, IL-6, IL-12, IL-15, and IFN-γ) is upregulated. Suitable immunostimulatory agents are also capable of increasing T cell proliferation. Such immunostimulatory agents include, but are not be limited to, CD40 ligand; cytokines, such as IFN-α, IFN-β, IFN-γ and IL-2; colony-stimulating factors, such as G-CSF (granulocyte colony-stimulating factor) and GM-CSF (granulocyte-macrophage colony-stimulating factor); an anti-CTLA-4 antibody; LPS (endotoxin); ssRNA; dsRNA; Bacille Calmette-Guerin (BCG); Levamisole hydrochloride; and intravenous immune globulins. In one embodiment an immunostimulatory agent may be a Toll-like Receptor (TLR) agonist. For example the immunostimulatory agent may be a TLR3 agonist such as double-stranded inosine:cytosine polynucleotide (Poly I:C, for example available as Ampligen™ from Hemispherx Bipharma, PA, US) or Poly A:U; a TLR4 agonist such as monophosphoryl lipid A (MPL) or RC-529 (for example as available from GSK, UK); a TLR5 agonist such as flagellin; a TLR7 or TLR8 agonist such as an imidazoquinoline TLR7 or TLR 8 agonist, for example imiquimod (eg Aldara™) or resiquimod and related imidazoquinoline agents (for example as available from 3M Corporation); or a TLR9 agonist such as a deoxynucleotide with unmethylated CpG motifs (so-called "CpGs", for example as available from Coley Pharmaceutical). Such immunostimulatory agents may be administered simultaneously, separately or sequentially with the antibodies and constructs of the present invention and may also be physically linked to the antibodies and constructs.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term antigen "cross-presentation" refers to presentation of exogenous protein antigens to T cells via MHC class I and class II molecules on APCs.

As used herein, the term "T cell-mediated response" refers to any response mediated by T cells, including effector T cells (e.g., $CD8^+$ cells) and helper T cells (e.g., $CD4^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by $CD8^+$ T cells.

The term "antibody" as referred to herein includes whole antibodies and any antigen binding fragment (i.e., "antigen-binding portion") or single chain thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., human DEC-205). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e., humanized antibodies).

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, is intended to refer to an antibody which is substantially free of other antibodies having different antigenic specificities (e.g., an isolated antibody that specifically binds to human DEC-205 is substantially free of antibodies that specifically bind antigens other than human DEC-205). An isolated antibody that specifically binds to an epitope of may, however, have cross-reactivity to other DEC-205 proteins from different species. However, the antibody preferably always binds to human DEC-205. In addition, an isolated antibody is typically substantially free of other cellular material and/or chemicals. In one embodiment of the invention, a combination of "isolated" antibodies having different DEC-205 specificities is combined in a well defined composition.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)). In the present case an epitope is preferably located in the extracellular domain of human DEC-205, for example in one or a combination of the cysteine rich domain, the FnII domain or one or more of the ten C-type lectin-like domains of human DEC-205.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 2000 instrument using recombinant human DEC-205 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

Also encompassed by the present invention are antibodies that bind the same epitope and/or antibodies that compete for binding to human DEC-205 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as DEC-205. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

The term "$K_D$," as used herein, is intended to refer to the dissociation equilibrium constant of a particular antibody-antigen interaction. Typically, the human antibodies of the invention bind to DEC-205 with a dissociation equilibrium constant ($K_D$) of approximately $10^{-8}$ M or less, such as less than $10^{-9}$ M or $10^{-10}$ M or even lower when determined by surface plasmon resonance (SPR) technology in a BIACORE 2000 instrument using recombinant human DEC-205 as the analyte and the antibody as the ligand.

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "isotype" refers to the antibody class (e.g., IgM or IgG1) that is encoded by heavy chain constant region genes. In one embodiment, a human monoclonal antibody of the invention is of the IgG1 isotype. In another embodiment, a human monoclonal antibody of the invention is of the IgG2 isotype.

The term "binds to immobilized DEC-205," refers to the ability of a human antibody of the invention to bind to DEC-205, for example, expressed on the surface of a cell or which is attached to a solid support.

The term "cross-reacts," as used herein, refers to the ability of an antibody of the invention to bind to DEC-205 from a different species. For example, an antibody of the present invention which binds human DEC-205 may also bind cynomologous DEC-205. As used herein, cross-reactivity is measured by detecting a specific reactivity with purified antigen in binding assays (e.g., SPR, ELISA) or binding to, or otherwise functionally interacting with, cells physiologically expressing DEC-205. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or binding to DEC-205 expressing cells from the species concerned (e.g., dendritic cells) by, for example, flow cytometric techniques.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to DEC-205, is intended to refer to a nucleic acid molecule in which the nucleotide sequences encoding the antibody or antibody portion are free of other nucleotide sequences encoding antibodies or antibody portions that bind antigens other than DEC-205, which other sequences may naturally flank the nucleic acid in human genomic DNA. For example, SEQ ID NOs: 2, 3 (with signal peptide)/4 (without signal peptide), and SEQ ID NOs: 8, 9 (with signal peptide)/10 (without signal peptide) correspond, respectively, to the nucleotide and amino acid sequences comprising the heavy chain ($V_H$) and light chain ($V_L$) variable regions of the human anti-DEC-205 antibody 3D6-2F4 of the invention. In particular, SEQ ID NO: 2 and 3/4 correspond to the nucleotide and amino acid sequence, respectively, of $V_H$ of the 3D6-2F4 antibody, SEQ ID NO: 8 and 9/10 correspond to the nucleotide and amino acid sequence, respectively, of $V_L$ of the 3D6-2F4 antibody.

The present invention also encompasses "conservative sequence modifications" of the sequences set forth in SEQ ID NOs: 2-91, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs: 2-91 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-DEC-205 antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997))

Alternatively, in another embodiment, mutations can be introduced randomly along all or part of an anti-DEC-205 antibody coding sequence, such as by saturation mutagenesis, and the resulting modified anti-DEC-205 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg-.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "antigen presenting cell" or "APC" is a cell that displays foreign antigen complexed with MHC on its surface. T-cells recognize this complex using T-cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis. Examples of APC receptors include, but are not limited to C-type lectins, such as, the human Dendritic and Epithelial Cell 205 receptor (DEC-205), and the human macrophage mannose receptor.

The term "antigen presentation" refers to the process by which APCs capture antigens and enables their recognition by T-cells, e.g., as a component of an MHC-I and/or MHC-II conjugate.

The terms "inducing an immune response" and "enhancing an immune response" are used interchangeably and refer the stimulation of an immune response (i.e., either passive or adaptive) to a particular antigen.

The terms "treat," "treating," and "treatment," as used herein, refer to therapeutic or preventative measures described herein. The methods of "treatment" employ administration to a subject, in need of such treatment, a human antibody of the present invention, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

I. Production of Antibodies to DEC-205

The present invention encompasses antibodies, e.g., fully human antibodies, that bind DEC-205, e.g., human DEC-205. Exemplary monoclonal antibodies that bind DEC-205 include 3D6-2F4, 3D6-4C8, 3G9-2D2, 5A8-1F1, 2D3-1F5-2A9, 3C7-3A3, 5D12-5G1, 1G6-1G6, 5C3-2-3F6, 1E6-3D10 and 3A4-1C10. Monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

Accordingly, in one embodiment, a hybridoma method is used for producing an antibody that binds human DEC-205. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies:Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies and antibody portions that bind human DEC-205 can be isolated from antibody phage libraries generated using the techniques described in, for example, McCafferty et al., Nature, 348:552-554 (1990). Clackson et al., Nature, 352:624-628 (1991), Marks et al., J. Mol. Biol., 222:581-597 (1991) and Hoet et al (2005) Nature Biotechnology 23, 344-348; U.S. Pat. Nos. 5,223,409; 5,403, 484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)) may also be used.

In a particular embodiment, the antibody that binds human DEC-205 is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to human DEC-205.

The preferred animal system for generating hybridomas which produce antibodies of the invention is the murine system. Hybridoma production in the mouse is well known in the art, including immunization protocols and techniques for isolating and fusing immunized splenocytes.

In one embodiment, antibodies directed against DEC-205 are generated using transgenic or transchromosomal mice carrying parts of the human immune system rather than the mouse system. In one embodiment, the invention employs transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). The preparation of HuMAb mice is described in detail in Section II below and in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Lonberg et al., (1994) Nature 368(6474): 856-859; Lonberg, N. (1994) Handbook of Experimental Pharmacology 113:49-101; Taylor, L. et al. (1994) International Immunology 6: 579-591; Lonberg, N. and Huszar, D. (1995) Intern. Rev. Immunol. Vol. 13: 65-93; Harding, F. and Lonberg, N. (1995) Ann. N.Y. Acad. Sci. 764:536-546; Fishwild, D. et al. (1996) Nature Biotechnology 14: 845-851. See further, U.S. Pat. Nos. 5,545,806; 5,569, 825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

Immunizations

To generate fully human antibodies to DEC-205, transgenic or transchromosomal mice containing human immunoglobulin genes (e.g., HCo12, HCo7 or KM mice) can be immunized with a purified or enriched preparation of the DEC-205 antigen and/or cells expressing DEC-205, as described, for example, by Lonberg et al. (1994) Nature 368 (6474): 856-859; Fishwild et al. (1996) Nature Biotechnology 14: 845-851 and WO 98/24884. As described herein, HuMAb mice are immunized either with recombinant DEC-205 proteins or cell lines expressing DEC-205 as immunogens. Alternatively, mice can be immunized with DNA encoding human DEC-205. Preferably, the mice will be 6-16 weeks of age upon the first infusion. For example, a purified or enriched preparation (5-50 μg) of the recombinant DEC-205 antigen can be used to immunize the HuMAb mice intraperitoneally. In the event that immunizations using a purified or enriched preparation of the DEC-205 antigen do not result in antibodies, mice can also be immunized with cells expressing DEC-205, e.g., a cell line, to promote immune responses. Exemplary cell lines include DEC-205-overexpressing stable CHO and Raji cell lines.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital bleeds. The plasma can be screened by ELISA (as described below), and mice with sufficient titers of anti-DEC-205 human immunoglobulin can be used for fusions. Mice can be boosted intravenously with antigen 3 days before sacrifice and removal of the spleen.

Generation of Hybridomas Producing Monoclonal Antibodies to DEC-205

To generate hybridomas producing monoclonal antibodies to DEC-205, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human anti-DEC-205 monoclonal IgM and IgG antibodies, or for binding to the surface of cells expressing DEC-205, e.g., a CHO cell line expressing DEC-205, by FLISA (fluorescence-linked immunosorbent assay). Once extensive hybridoma growth occurs, medium can be observed usually after 10-14 days. The antibody secreting hybridomas can be replated, screened again, and if still positive for IgG, anti-DEC-205 monoclonal antibodies can be subcloned at least twice by limiting dilution. The stable subclones can then be cultured in vitro to generate antibody in tissue culture medium for characterization.

Generation of Transfectomas Producing Monoclonal Antibodies to DEC-205

Antibodies of the invention also can be produced in a host cell transfectoma using, for example, a combination of recombinant DNA techniques and gene transfection methods as is well known in the art (Morrison, S. (1985) Science 229:1202).

For example, in one embodiment, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively these cloned antibody genes can be expressed in other expression systems such as E. coli or in complete organisms or can be synthetically expressed.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors were constructed so that PCR amplified V heavy and V kappa light chain cDNA sequences could be used to reconstruct complete heavy and light chain minigenes. These plasmids can be used to express completely human IgG$_1$κ or IgG$_4$κ antibodies. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, structural features of anti-DEC-205 antibodies of the invention are used to create structurally related anti-DEC-205 antibodies that retain at least one functional property of the antibodies of the invention, such as, for example, binding to human DEC-205 with an affinity constant of at least $10^8$ M$^{-1}$ as measured by surface plasmon resonance;
internalizing after binding to human dendritic cells expressing DEC-205;
localizing to antigen processing compartments in human dendritic cells;
activating human dendritic cells expressing DEC-205; cross-reacting with DEC-205 on non-human primate dendritic cells or those of other species; and generating or enhancing human T cell, such as CTL, responses to an antigen, preferably CTL responses mediated by both MHC Class I and Class II pathways.

In one embodiment, one or more CDR regions of antibodies of the invention can be combined recombinantly with known framework regions and CDRs to create additional, recombinantly-engineered, anti-DEC-205 antibodies of the invention. The heavy and light chain variable framework regions can be derived from the same or different antibody sequences. The antibody sequences can be the sequences of naturally occurring antibodies or can be consensus sequences of several antibodies. See Kettleborough et al., *Protein Engineering* 4:773 (1991); Kolbinger et al., *Protein Engineering* 6:971 (1993) and Carter et al., WO 92/22653.

Accordingly, in another embodiment, the invention provides a method for preparing an anti-DEC-205 antibody including:

preparing an antibody including (1) heavy chain framework regions and heavy chain CDRs, where at least one of the heavy chain CDRs includes an amino acid sequence selected from the amino acid sequences of CDRs shown in SEQ ID NOs: 5, 6, 7, 17, 18, 19, 29, 30, 31, 41, 42, 43, 53, 54, 55, 65, 66, 67, 71, 72, 73, 77, 78, 79, 89, 90 or 91; and (2) light chain framework regions and light chain CDRs, where at least one of the light chain CDRs includes an amino acid sequence selected from the amino acid sequences of CDRs shown in SEQ ID NOs: 11, 12, 13, 23, 24, 25, 35, 36, 37, 47, 48, 49, 59, 60, 61, 83, 84, or 85, where the antibody retains the ability to bind to DEC-205. The ability of the antibody to bind DEC-205 can be determined using standard binding assays, such as those set forth in the Examples (e.g., an ELISA or a FLISA).

It is well known in the art that antibody heavy and light chain CDR3 domains play a particularly important role in the binding specificity/affinity of an antibody for an antigen (see, Hall et al., *J. Immunol.*, 149:1605-1612 (1992); Polymenis et al., *J. Immunol.*, 152:5318-5329 (1994); Jahn et al., *Immunobiol.*, 193:400-419 (1995); Klimka et al., *Brit. J. Cancer*, 83:252-260 (2000); Beiboer et al., *J. Mol. Biol*, 296:833-849 (2000); Rader et al., *Proc. Natl. Acad. Sci. USA*, 95:8910-8915 (1998); Barbas et al., *J. Am. Chem. Soc.*, 116:2161-2162 (1994); Ditzel et al., *J. Immunol.*, 157:739-749 (1996)). Accordingly, the recombinant antibodies of the invention prepared as set forth above preferably comprise the heavy and/or light chain CDR3s of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10. The antibodies further can comprise the CDR2s of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10. The antibodies further can comprise the CDR1s of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10. The antibodies can further comprise any combinations of the CDRs.

Accordingly, in another embodiment, the invention further provides anti-DEC-205 antibodies comprising: (1) heavy chain framework regions, a heavy chain CDR1 region, a heavy chain CDR2 region, and a heavy chain CDR3 region, wherein the heavy chain CDR3 region is selected from the CDR3s of 3D6-2F4, 3D6-4C8, 3G9-2D2, 5A8-1F1, 2D3-1F5-2A9, 3C7-3A3, 5D12-5G1, 1G6-1G6 and 3A4-1C10, for example, a heavy chain CDR3 region of 3D6-2F4 as shown in SEQ ID NO: 7; and (2) light chain framework regions, a light chain CDR1 region, a light chain CDR2 region, and a light chain CDR3 region, wherein the light chain CDR3 region is selected from the CDR3s of 3D6-2F4, 3D6-4C8, 3G9-2D2, 5A8-1F1, 2D3-1F5-2A9, 3C7-3A3, 5D12-5G1, 1G6-1G6 and 3A4-1C10, for example, a light chain CDR3 region of 3D6-2F4 as shown in SEQ ID NO: 13 wherein the antibody binds DEC-205. The antibody may further include the heavy chain CDR2 and/or the light chain CDR2 of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10. The antibody may further comprise the heavy chain CDR1 and/or the light chain CDR1 of 3D6-2F4, 3D6-4C8, 3G9-2D2, 5A8-1F1, 2D3-1F5-2A9, 3C7-3A3, 5D12-5G1, 1G6-1G6 and 3A4-1C10.

Generation of Antibodies Having Modified Sequences

In another embodiment, the variable region sequences, or portions thereof, of the anti-DEC-205 antibodies of the invention are modified to create structurally related anti-DEC-205 antibodies that retain binding (i.e., to the same epitope as the unmodified antibody) and, thus, are functionally equivalent. Methods for identifying residues that can be altered without removing antigen binding are well-known in the art (see, e.g., Marks et al. (*Biotechnology* (1992) 10(7):779-83 (monoclonal antibodies diversification by shuffling light chain variable regions, then heavy chain variable regions with fixed CDR3 sequence changes), Jespers et al., (1994) Biotechnology 12(9):899-903 (selection of human antibodies from phage display repertoires to a single epitope of an antigen), Sharon et al. (1986) *PNAS USA* 83(8):2628-31 (site-directed mutagenesis of an invariant amino acid residue at the variable-diversity segments junction of an antibody); Casson et al. (1995) *J. Immunol.* 155(12):5647-54 (evolution of loss and change of specificity resulting from random mutagenesis of an antibody heavy chain variable region).

Accordingly, in one aspect of the invention, the CDR1, 2, and/or 3 regions of the engineered antibodies described above can comprise the exact amino acid sequence(s) as those of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10 disclosed herein. However, in other aspects of the invention, the antibodies comprise derivatives from the exact CDR sequences of 3D6-2F4, 3D6-4C8, 3G9-2D2, 5A8-1F1, 2D3-1F5-2A9, 3C7-3A3, 5D12-5G1, 1G6-1G6 and 3A4-1C10 yet still retain the ability of to bind DEC-205 effectively. Such sequence modifications may include one or more amino acid additions, deletions, or substitutions, e.g., conservative sequence modifications as described above. Sequence modifications may also be based on the consensus sequences described above for the particular CDR1, CDR2, and CDR3 sequences of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10.

Accordingly, in another embodiment, the engineered antibody may be composed of one or more CDRs that are, for example, 90%, 95%, 98% or 99.5% identical to one or more CDRs of antibodies 3D6-2F4, 3D6-4C8, 3G9-2D2, 5A8-1F1, 2D3-1F5-2A9, 3C7-3A3, 5D12-5G1, 1G6-1G6 and 3A4-1C10. Ranges intermediate to the above-recited values, e.g., CDRs that are 90-95%, 95-98%, or 98-100% identical identity to one or more of the above sequences are also intended to be encompassed by the present invention.

In another embodiment, one or more residues of a CDR may be altered to modify binding to achieve a more favored on-rate of binding, a more favored off-rate of binding, or both, such that an idealized binding constant is achieved. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to or instead of modifications within the CDRs, modifications can also be made within one or more of the framework regions, FR1, FR2, FR3 and FR4, of the heavy and/or the light chain variable regions of a antibody, so long as these modifications do not eliminate the binding affinity of the antibody. For example, one or more non-germline amino acid residues in the framework regions of the heavy and/or the light chain variable region of a antibody of the invention, is substituted with a germline amino acid residue, i.e., the corresponding amino acid residue in the human germline sequence for the heavy or the light chain variable region, which the antibody has significant sequence identity with. For example, a antibody chain can be aligned to a germline antibody chain which it shares significant sequence identity with, and the amino acid residues which do not match between antibody framework sequence and the germline chain framework can be substituted with corresponding residues from the germline sequence. When an amino acid differs between a antibody variable framework region and an equivalent human germline sequence variable framework region, the antibody framework amino acid should usually be substituted by the equivalent human germline sequence amino acid if it is reasonably expected that the amino acid falls within one of the following categories:

(1) an amino acid residue which noncovalently binds antigen directly, (2) an amino acid residue which is adjacent to a CDR region, (3) an amino acid residue which otherwise interacts with a CDR region (e.g., is within about 3-6 Å of a CDR region as determined by computer modeling), or (4) an amino acid reside which participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like. Accordingly, in one embodiment, an amino acid residue in the framework region of a antibody of the invention is substituted with the corresponding germline amino acid residue which noncovalently binds antigen directly.

Residues which are "adjacent to a CDR region" include amino acid residues in positions immediately adjacent to one or more of the CDRs in the primary sequence of the antibody, for example, in positions immediately adjacent to a CDR as defined by Kabat, or a CDR as defined by Chothia (see e.g., Chothia and Lesk *J. Mol. Biol.* 196:901 (1987)). Accordingly, in one embodiment, an amino acid residue within the framework region of an antibody of the invention is substituted with a corresponding germline amino acid residue which is adjacent to a CDR region.

Residues that "otherwise interact with a CDR region" include those that are determined by secondary structural analysis to be in a spatial orientation sufficient to affect a CDR region. Such amino acids will generally have a side chain atom within about 3 angstrom units (Å) of some atom in the CDRs and must contain an atom that could interact with the CDR atoms according to established chemical forces, such as those listed above. Accordingly, in one embodiment, an amino acid residue within the framework region of an antibody of the invention is substituted with the corresponding germline amino acid residue which otherwise interacts with a CDR region.

The amino acids at several positions in the framework are known to be important for determining CDR confirmation (e.g., capable of interacting with the CDRs) in many antibodies (Chothia and Lesk, supra, Chothia et al., supra and Tramontano et al., J. Mol. Biol. 215:175 (1990), all of which are incorporated herein by reference). These authors identified conserved framework residues important for CDR conformation by analysis of the structures of several known antibodies. The antibodies analyzed fell into a limited number of structural or "canonical" classes based on the conformation of the CDRs. Conserved framework residues within members of a canonical class are referred to as "canonical" residues. Canonical residues include residues 2, 25, 29, 30, 33, 48, 64, 71, 90, 94 and 95 of the light chain and residues 24, 26, 29, 34, 54, 55, 71 and 94 of the heavy chain. Additional residues (e.g., CDR structure-determining residues) can be identified according to the methodology of Martin and Thorton (1996) *J. Mol. Biol.* 263:800. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs.

Additional residues which may effect conformation of the CDRs can be identified according to the methodology of Foote and Winter (1992) *J. Mol. Biol.* 224:487. Such residues are termed "vernier" residues and are those residues in the framework region closely underlying (i.e., forming a "platform" under) the CDRs.

Residues which "participate in the VL-VH interface" or "packing residues" include those residues at the interface between VL and VH as defined, for example, by Novotny and Haber, *Proc. Natl. Acad. Sci. USA*, 82:4592-66 (1985) or Chothia et al, supra.

Occasionally, there is some ambiguity about whether a particular amino acid falls within one or more of the above-mentioned categories. In such instances, alternative variant antibodies are produced, one of which has that particular substitution, the other of which does not. Alternative variant antibodies so produced can be tested in any of the assays described herein for the desired activity, and the preferred antibody selected.

Additional candidates for substitution within the framework region are amino acids that are unusual or "rare" for an antibody at that position. These amino acids can be substituted with amino acids from the equivalent position of the human germline sequence or from the equivalent positions of more typical antibodies. For example, substitution may be desirable when the amino acid in a framework region of the antibody is rare for that position and the corresponding amino acid in the germline sequence is common for that position in immunoglobulin sequences; or when the amino acid in the antibody is rare for that position and the corresponding amino acid in the germline sequence is also rare, relative to other sequences. It is contemplated that by replacing an unusual amino acid with an amino acid from the germline sequence that happens to be typical for antibodies, the antibody may be made less immunogenic.

The term "rare", as used herein, indicates an amino acid occurring at that position in less than about 20%, preferably less than about 10%, more preferably less than about 5%, even more preferably less than about 3%, even more preferably less than about 2% and even more preferably less than about 1% of sequences in a representative sample of sequences, and the term "common", as used herein, indicates an amino acid occurring in more than about 25% but usually more than about 50% of sequences in a representative sample. For example, all light and heavy chain variable region sequences are respectively grouped into "subgroups" of sequences that are especially homologous to each other and have the same amino acids at certain critical positions (Kabat et al., supra). When deciding whether an amino acid in an antibody sequence is "rare" or "common" among sequences, it will often be preferable to consider only those sequences in the same subgroup as the antibody sequence.

In general, the framework regions of antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting immunoglobulin. Thus, in one embodiment the variable framework region of the antibody shares at least 85% sequence identity to a human germline variable framework region sequence or consensus of such sequences. In another embodiment, the variable framework region of the antibody shares at least 90%, 95%, 96%, 97%, 98% or 99% sequence identity to a human germline variable framework region sequence or consensus of such sequences.

In addition to simply binding DEC-205, an antibody may be selected for its retention of other functional properties of antibodies of the invention, such as, for example:

(a) binding to human DEC-205 with an affinity constant of at least $10^8 M^{-1}$ as measured by surface plasmon resonance;

(b) internalizing after binding to human dendritic cells expressing DEC-205;

(c) localizing to antigen processing compartments in the dendritic cells;

(d) activating human dendritic cells expressing DEC-205;

(e) cross-reacting with DEC-205 on non-human primate dendritic cells or those of other species;

(f) generating or enhancing human T-cell responses, preferably T-cell responses mediated by both MHC Class I and Class II pathways;

(g) generating or enhancing human CD4+, CD8+ or NKT cell responses; and (h) induces peripheral $CD8^+$ T cell tolerance.

Characterization of Monoclonal Antibodies to DEC-205

Monoclonal antibodies of the invention can be characterized for binding to DEC-205 using a variety of known techniques. Generally, the antibodies are initially characterized by ELISA. Briefly, microtiter plates can be coated with purified DEC-205 in PBS, and then blocked with irrelevant proteins such as bovine serum albumin (BSA) diluted in PBS. Dilutions of plasma from DEC-205-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the DEC-205 immunogen. Hybridomas that bind, preferably with high affinity, to DEC-205 can than be subcloned and further characterized. One clone from each hybridoma, which retains the reactivity of the parent cells (by ELISA), can then be chosen for making a cell bank, and for antibody purification.

To purify anti-DEC-205 antibodies, selected hybridomas can be grown in roller bottles, two-liter spinner-flasks or other culture systems. Supernatants can be filtered and concentrated before affinity chromatography with protein A-sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-DEC-205 monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-Ig overnight at 4° C. After blocking with 5% BSA, the plates are reacted with 10 µg/ml of monoclonal antibodies or purified isotype controls, at ambient temperature for two hours. The wells can then be reacted with either IgG1 or other isotype specific conjugated probes. Plates are developed and analyzed as described above.

To test the binding of monoclonal antibodies to live cells expressing DEC-205, flow cytometry can be used. Briefly, cell lines and/or human PBMCs expressing membrane-bound DEC-205 (grown under standard growth conditions) are mixed with various concentrations of monoclonal antibodies in PBS containing 0.1% BSA and 0.01% NaN3 at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-DEC-205 IgGs can be further tested for reactivity with the DEC-205 antigen by Western blotting. Briefly, cell extracts from cells expressing DEC-205 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-DEC-205 antibodies include standard assays known in the art, for example, Biacore™ surface plasmon resonance (SPR) analysis using a Biacore™ 2000 SPR instrument (Biacore AB, Uppsala, Sweden), as described in Example 2 herein.

II. Molecular Conjugates/Immunotoxins

The present invention provides a variety of therapeutic molecular conjugates (e.g., vaccine conjugates) which include an antigen, such as a tumor or viral antigen, linked to an antibody that binds to a receptor on an APC, for example, an antibody which binds to DEC-205. This allows for targeting of the antigen to APCs, such as cells expressing DEC-205 (e.g., dendritic cells and B cells) to enhance processing, presentation and, ultimately, an immune response against the antigen(s), e.g., a CTL response. A schematic representation of such a conjugate is shown in FIG. 8. In the example shown, an antigen is genetically fused to the CH3 domain of each of the heavy chains of a substantially complete anti-DEC-205 antibody. However, it will be appreciated that the antigen may alternatively be joined to other parts of such an antibody or fragment thereof, and that other forms of conjugation, such as chemical conjugation, may also be employed, as discussed further below.

Suitable antigens for use in the present invention include, for example, infectious disease antigens and tumor antigens, against which protective or therapeutic immune responses are desired, e.g., antigens expressed by a tumor cell or a pathogenic organism or infectious disease antigens. For example, suitable antigens include tumor-associated antigens for the prevention or treatment of cancers. Examples of tumor-associated antigens include, but are not limited to, sequences comprising all or part of the sequences of βhCG, gp100 or Pmel17, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 and MUC-1 antigens, and germ cell derived tumor antigens. Tumor associated antigens also include the blood group antigens, for example, Le$^a$, Le$^b$, LeX, LeY, H-2, B-1, B-2 antigens. Alternatively, more than one antigen can be included within the antigen-antibody constructs of the invention. For example, a MAGE antigen can be combined with other antigens such as melanin A, tyrosinase, and gp100 along with adjuvants such as GM-CSF or IL-12, and linked to an anti-APC antibody.

Other suitable antigens include viral antigens for the prevention or treatment of viral diseases. Examples of viral antigens include, but are not limited to, HIV-1 gag, HIV-1 env, HIV-1 nef, HBV (surface or core antigens), HPV, FAS, HSV-1, HSV-2, p17, ORF2 and ORF3 antigens. Examples of bacterial antigens include, but are not limited to, *Toxoplasma gondii* or *Treponema pallidum*. The antibody-bacterial antigen conjugates of the invention can be in the treatment or prevention of various bacterial diseases such as Anthrax, Botulism, Tetanus, Chlamydia, Cholera, Diphtheria, Lyme Disease, Syphilis and Tuberculosis.

Sequences of the foregoing antigens are well known in the art. For example, an example of a MAGE-3 cDNA sequence is provided in U.S. Pat. No. 6,235,525 (Ludwig Institute for Cancer Research); examples of NY-ESO-1 nucleic acid and protein sequences are provided in U.S. Pat. No. 5,804,381 and U.S. Pat. No. 6,069,233 (Ludwig Institute for Cancer Research); examples of Melan-A nucleic acid and protein sequences are provided in U.S. Pat. No. 5,620,886 and U.S. Pat. No. 5,854,203 (Ludwig Institute for Cancer Research); examples of NY-BR-1 nucleic acid and protein sequences are provided in U.S. Pat. No. 6,774,226 and U.S. Pat. No. 6,911,529 (Ludwig Institute for Cancer Research) and examples of NY-CO-58 nucleic acid and protein sequences are provided in WO 02090986 (Ludwig Institute for Cancer Research); an example of an amino acid sequence for the HER-2/neu protein is available at GENBANK® Accession No. AAA58637; and a nucleotide sequence (mRNA) for human carcinoembryonic antigen-like 1 (CEA-1) is available at GENBANK® Accession No. NM_020219.

An HPV antigen that may be used in the pharmaceutical compositions and the methods of the invention may include, for example an HPV-16 antigen, an HPV-18 antigen, an HPV-31 antigen, an HPV-33 antigen and/or an HPV-35 antigen; and is suitably an HPV-16 antigen and/or HPV-18 antigen. A genome of HPV-16 is described in Virology, 145:181-185 (1985) and DNA sequences encoding HPV-18 are described in U.S. Pat. No. 5,840,306, the disclosures of which are incorporated by reference herein in their entirety. HPV-16 antigens (e.g., seroreactive regions of the E1 and/or E2 proteins of HPV-16) are described in U.S. Pat. No. 6,531,127, and HPV-18 antigens (e.g., seroreactive regions of the L1 and/or L2 proteins of HPV-18) are described in U.S. Pat. No. 5,840,306, the disclosures of which are incorporated by reference herein. Similarly, a complete genome for HBV is available at GENBANK® Accession No. NC_003977, the disclosure of which is incorporated herein. The genome of HCV is described in European Patent Application No. 318 216, the disclosure of which is incorporated herein. PCT/US90/01348, incorporated by reference herein, discloses sequence information of clones of the HCV genome, amino acid sequences of HCV viral proteins and methods of making and using such compositions for HCV vaccines comprising HCV proteins and peptides derived there from.

Antigenic peptides of proteins (i.e., those containing T cell epitopes) can be identified in a variety of manners well known in the art. For example, T cell epitopes can be predicted by analyzing the sequence of the protein using web-based predictive algorithms (BIMAS & SYFPEITHI) to generate potential MHC class I and II-binding peptides that match an internal database of 10,000 well characterized MHC binding peptides previously defined by CTLs. High scoring peptides can be ranked and selected as "interesting" on the basis of high affinity to a given MHC molecule.

Another method for identifying antigenic peptides containing T cell epitopes is by dividing the protein into non-overlapping peptides of desired length or overlapping peptides of desired lengths which can be produced recombinantly, synthetically, or in certain limited situations, by chemical cleavage of the protein and tested for immunogenic properties, e.g., eliciting a T cell response (i.e., proliferation or lymphokine secretion).

In order to determine precise T cell epitopes of the protein by, for example, fine mapping techniques, a peptide having T cell stimulating activity and thus comprising at least one T cell epitope, as determined by T cell biology techniques, can be modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. Peptides are selected based on various factors, including the strength of the T cell response to the peptide (e.g., stimulation index). The physical and chemical properties of these selected peptides (e.g., solubility, stability) can then be examined to determine whether the peptides are suitable for use in therapeutic compositions or whether the peptides require modification.

In addition, the vaccine conjugate can include one or more immunostimulatory agents that also enhance the immune response against the antigen. Antibody-antigen vaccine conjugates of the invention can be made genetically or chemically. In either case, the antibody portion of the conjugate may consist of the whole antibody or a portion of the antibody, such as the Fab fragment or single-chain Fv. In addition, more than one antigen and/or immunostimulatory agent can be included in the conjugate.

Chemically constructed antibody-antigen conjugates can be made using a variety of well known and readily available cross-linking reagents. These cross-linking reagents can be homofunctional or heterofunctional compounds, such as N-succinimidyl-3-(2-pyridyldithio)propionate (SPDP), N-succinimidyl-5-acetyl-thioacetate (SATA), sulfosuccinimidyl 4-(N-maleimidomethyl)cyclohaxane-1-carboxylate (sulfo-SMCC), 5,5'-dithiobis(2-nitrobenzoic acid) (DTNB), that form covalent linkages with different reactive amino acid or carbohydrate side chains on the anti-dendritic antibody and selected antigen. Other coupling and cross-linking agents also can be used to generate covalent linkages, such as protein A, carbodiimide, and o-phenylenedimaleimide (oPDM); (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.). Immunostimulatory agents can also be chemically linked to the molecular conjugates of the present invention using the same linking methods described above.

In another embodiment, the antibodies of the present invention are linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a dendritic-related disorder, such as an autoimmune or inflammatory disease, or graft versus host disease.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

In another embodiment, the antibodies of the present invention can be used to directly target whole cells, e.g., a tumor cell, an effector cell or a microbial pathogen, to dendritic cells. For example, anti-DEC-205 antibodies can be directly expressed on the surface of a cell, for example, by transfection or transduction of a cell with a vector containing nucleic acid sequences encoding an antibody of the invention. This can be done, for example, by transfecting the target cell with a nucleic acid encoding a fusion protein containing a transmembrane domain and a anti-dendritic cell antibody, or antigen binding fragment thereof. Methods for generating such nucleic acids, fusion proteins, and cells expressing such fusion proteins are described, for example, in U.S. patent application Ser. No. 09/203,958, incorporated herein in its entirety by this reference. Alternatively, anti-dendritic cell antibodies, or antigen binding fragments thereof, can be bound to a cell or a pathogen by the use of chemical linkers, lipid tags, or other related methods (deKruif, J. et al. (2000) *Nat. Med.* 6:223-227; Nizard, P. et al. (1998) *FEBS Lett.* 433:83-88). Cells with surface-anchored anti-DEC-205 antibodies may be used to induce specific immune responses against the cell, e.g., a tumor cell or microbial pathogen.

III. Pharmaceutical Compositions

In another embodiment, the present invention provides a composition, e.g., a pharmaceutical composition, containing one or a combination of monoclonal antibodies of the present invention, formulated together with a pharmaceutically acceptable carrier. Compositions containing bispecific molecules or molecular conjugates which comprise an antibody of the present invention are also provided. In one embodiment, the compositions include a combination of multiple (e.g., two or more) isolated antibodies of the invention. Preferably, each of the antibodies of the composition binds to a distinct, pre-selected epitope of DEC-205.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, and chemotherapeutics. The pharmaceutical compositions of the invention can also be administered in conjunction with radiation therapy. Co-administration with other antibodies, such as CD4 specific antibodies, or IL-2 specific antibodies, are also encompassed by the invention. Such combinations with CD4 specific antibodies or IL-2 specific antibodies are considered particularly useful for treating autoimmune diseases and transplant rejections. Combinations with antibodies to CTLA4, CD40 etc particularly useful in cancer and infectious disease treatments.

In another embodiment, a vaccine conjugate that is rapidly internalized by APCs can be combined with a monoclonal antibody that enhances antigen presenting cell activities of dendritic cells, e.g., release of immunostimulatory cytokines.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Examples of adjuvants which may be used with the antibodies and constructs of the present invention include: Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatised polysaccharides; polyphosphazenes; biodegradable microspheres; cytokines, such as GM-CSF, interleukin-2, -7, -12, and other like factors; 3D-MPL; CpG oligonucleotide; and monophosphoryl lipid A, for example 3-de-O-acylated monophosphoryl lipid A.

MPL adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996.

Further alternative adjuvants include, for example, saponins, such as Quil A, or derivatives thereof, including QS21 and QS7 (Aquila Biopharmaceuticals Inc., Framingham, Mass.); Escin; Digitonin; or Gypsophila or *Chenopodium* quinoa saponins; Montanide ISA 720 (Seppic, France); SAF (Chiron, Calif., United States); ISCOMS (CSL), MF-59 (Chiron); the SBAS series of adjuvants (e.g., SBAS-2 or SBAS-4, available from SmithKline Beecham, Rixensart, Belgium); Detox (Enhanzyn™) (Corixa, Hamilton, Mont.); RC-529 (Corixa, Hamilton, Mont.) and other aminoalkyl glucosaminide 4-phosphates (AGPs); polyoxyethylene ether adjuvants such as those described in WO 99/52549A1; synthetic imidazoquinolines such as imiquimod [S-26308, R-837], (Harrison, et al., Vaccine 19: 1820-1826, 2001; and resiquimod [S-28463, R-848] (Vasilakos, et al., Cellular immunology 204: 64-74, 2000; Schiff bases of carbonyls and amines that are constitutively expressed on antigen presenting cell and T-cell surfaces, such as tucaresol (Rhodes, J. et al., Nature 377: 71-75, 1995); cytokine, chemokine and co-stimulatory molecules as either protein or peptide, including for example pro-inflammatory cytokines such as Interferon, GM-CSF, IL-1 alpha, IL-1 beta, TGF-alpha and TGF-beta, Th1 inducers such as interferon gamma, IL-2, IL-12, IL-15, IL-18 and IL-21, Th2 inducers such as IL-4, IL-5, IL-6, IL-10 and IL-13 and other chemokine and co-stimulatory genes such as MCP-1, MIP-1 alpha, MIP-1 beta, RANTES, TCA-3, CD80, CD86 and CD40L; immunostimulatory agents targeting ligands such as CTLA-4 and L-selectin, apoptosis stimulating proteins and peptides such as Fas; synthetic lipid based adjuvants, such as vaxfectin, (Reyes et al., Vaccine 19: 3778-3786, 2001) squalene, alpha-tocopherol, polysorbate 80, DOPC and cholesterol; endotoxin, [LPS], (Beutler, B., Current Opinion in Microbiology 3: 23-30, 2000); ligands that trigger Toll receptors to produce Th1-inducing cytokines, such as synthetic Mycobacterial lipoproteins, Mycobacterial protein p19, peptidoglycan, teichoic acid and lipid A; and CT (cholera toxin, subunits A and B) and LT (heat labile enterotoxin from *E. coli*, subunits A and B), heat shock protein family (HSPs), and LLO (listeriolysin 0; WO 01/72329). These and various further Toll-like Receptor (TLR) agonists are described for example in Kanzler et al, *Nature Medicine*, May 2007, Vol 13, No 5.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The ability of the antibodies to enhance antigen presentation or induce cytotoxic T cell (CTL) responses against a variety of target cells or pathogens can also be evaluated according to methods well known in the art.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

In one embodiment, the antibodies, bispecific molecules, and molecular conjugates of the present invention can be used to treat and/or prevent (e.g., immunize against) a variety of diseases and conditions.

One of the primary disease indications that can be treated using antibodies of the invention is cancer. This includes, but is not limited to, colon cancer, melanoma, lymphoma, prostate carcinoma, pancreatic carcinoma, bladder carcinoma, fibrosarcoma, rhabdomyosarcoma, mastocytoma, mammary adenocarcinoma, leukemia, or rheumatoid fibroblastsoma. Another primary disease indication is infectious diseases including, but not limited to, HIV, Hepatitis (e.g., A, B, & C), Influenza, Herpes, Giardia, Malaria, Leishmania, Staphylococcus Aureus, Pseudomonas aeruginosa. Another primary disease indication includes autoimmune diseases.

For use in therapy, vaccine conjugates of the invention can be administered to a subject directly (i.e., in vivo), either alone or with an immunostimulatory agent. In one aspect, the immunostimulatory agent is linked to the conjugate. Alternatively, the conjugates can be administered to a subject indirectly by first contacting the conjugates (e.g., by culturing or incubating) with APCs, such as dendritic cells, and then administering the cells to the subject (i.e., ex vivo). The contacting and delivering of the conjugates to APCs, such that they are processed and presented by the APCs prior to administration, is also referred to as antigen or cell "loading." Techniques for loading antigens to APCs are well known in the art and include, for example, Gunzer and Grabbe, Crit Rev Immunol 21 (1-3):133-45 (2001) and Steinman, Exp Hematol 24(8): 859-62 (1996).

In all cases, the vaccine conjugates and the immunostimulatory agents are administered in an effective amount to exert their desired therapeutic effect. The term "effective amount" refers to that amount necessary or sufficient to realize a desired biologic effect. For example, an effective amount could be that amount necessary to eliminate a tumor, cancer, or bacterial, viral or fungal infection. The effective amount for any particular application can vary depending on such factors as the disease or condition being treated, the particular conjugate being administered, the size of the subject, or the severity of the disease or condition. One of ordinary skill in the art can empirically determine the effective amount of a particular multispecific molecule without necessitating undue experimentation.

Preferred routes of administration for the vaccine conjugates include, for example, injection (e.g., subcutaneous, intravenous, parenteral, intraperitoneal, intrathecal). The injection can be in a bolus or a continuous infusion. Other routes of administration include oral administration.

Vaccine conjugates of the invention also can be coadministered with adjuvants and other therapeutic agents. It will be appreciated that the term "coadministered" as used herein includes any or all of simultaneous, separate, or sequential administration of the antibodies and conjugates of the present invention with adjuvants and other agents, including administration as part of a dosing regimen. The conjugates are typically formulated in a pharmaceutically acceptable carrier alone or in combination with such agents. Examples of such carriers include solutions, solvents, dispersion media, delay agents, emulsions and the like. The use of such media for pharmaceutically active substances is well known in the art. Any other conventional carrier suitable for use with the molecules falls within the scope of the instant invention.

Suitable agents for coadministration with the vaccine conjugates include other antibodies, cytotoxins and/or drugs. In one embodiment, the agent is an anti-CTLA-4 antibody which is known to aid or induce immune responses. In another embodiment, the agent is a chemotherapeutic agent. The vaccine conjugates also can be administered in combination with radiation.

Chemotherapeutic agents suitable for coadministration with the antibodies and conjugates of the present invention in the treatment of tumors include, for example: taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine) and temozolomide.

Agents that delete or inhibit immunosuppressive activities, for example, by immune cells (for example regulatory T-cells, NKT cells, macrophages, myeloid-derived suppressor cells, immature or suppressive dendritic cells) or suppressive factors produced by the tumor or host cells in the local microenvironment of the tumor (for example, TGFbeta, indoleamine 2,3 dioxygenase—IDO), may also be administered with the antibodies and conjugates of the present invention. Such agents include antibodies and small molecule drugs such as IDO inhibitors such as 1 methyl tryptophan or derivatives.

In another embodiment, the antibodies of the present invention can be used to treat a subject with an autoimmune, immune system, or inflammatory disorder, e.g., a disorder characterized by aberrant or unwanted immune activity associated with immunomodulation by dendritic cells. Autoimmune, immune system, and inflammatory disorders that may benefit from treatment with the anti-dendritic cells of the invention include rheumatoid arthritis, multiple sclerosis, immune-mediated or Type 1 diabetes mellitus, myasthenia gravis, pernicious anemia, Addison's disease, Sjogren's syndrome, psoriasis, lupus erythematosus, inflammatory bowel diseases such as Crohn's disease and ulcerative colitis, scleroderma/Raynaud's syndrome, Reiter's syndrome, and autoimmune thyroid diseases such as Hashimoto's thyroiditis and Graves's disease. For example, a subject suffering from an autoimmune disorder may benefit from inhibition of dendritic cell mediated presentation of an autoantigen.

The antibodies of the present invention may also be used for preventing and treating all forms of allergy and allergic disorder, including without limitation: ophthalmic allergic disorders, including allergic conjunctivitis, vernal conjunctivitis, vernal keratoconjunctivitis, and giant papillary conjunctivitis; nasal allergic disorders, including allergic rhinitis and sinusitis; otic allergic disorders, including eustachian tube itching; allergic disorders of the upper and lower airways, including intrinsic and extrinsic asthma; allergic disorders of the skin, including dermatitis, eczema and urticaria; and allergic disorders of the gastrointestinal tract.

Suitable agents for coadministration with the antibodies of the present invention for treatment of such immune disorders include for example, immunosuppressive agents such as rapamycin, cyclosporin and FK506; anti-TNFa agents such as etanercept, adalimumab and infliximab; and steroids. Examples of specific natural and synthetic steroids include, for example: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, paramethasone, prednisolone, prednisone, tixocortol and triamcinolone.

Other examples of diseases that can be treated using the anti-DEC-205 antibodies of the invention include transplant rejection and graft versus host disease.

Transplant Rejection

Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immune-tolerance in the recipient to the transplanted allograft or organ. When allogeneic cells or organs are transplanted into a host (i.e., the donor and donee are different individual from the same species), the host immune system is likely to mount an immune response to foreign antigens in the transplant (host-versus-graft disease) leading to destruction of the transplanted tissue. CD8+ cells, CD4+ cells and monocytes are all involved in the rejection of transplant tissues. The antibodies of the present invention are useful to inhibit dendritic cell mediated alloantigen-induced immune responses in the donee thereby preventing such cells from participating in the destruction of the transplanted tissue or organ.

Graft Versus Host Disease

A related use for the antibodies of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used to inhibit the activity of host antigen presenting cells, e.g., dendritic cells.

The present invention is further illustrated by the following examples which should not be construed as further limiting. The contents of Sequence Listing, figures and all references, patents and published patent applications cited throughout this application are expressly incorporated herein by reference.

EXAMPLES

Example 1

Generation of DEC-205-Specific Human Monoclonal Antibodies (HuMabs)

Human anti-DEC-205 monoclonal antibodies were generated by immunizing the HC2/KCo7 strain of HuMAb® transgenic mice ("HuMab" is a Trade Mark of Medarex, Inc., Princeton, N.J.) with a soluble human DEC-205 antigen. HC2/KCo7 HuMAb mice were generated as described in U.S. Pat. Nos. 5,770,429 and 5,545,806, the entire disclosures of which are hereby incorporated by reference.

Antigen and Immunization: The antigen was a soluble fusion protein comprising a DEC-205 extracellular domain (comprising all ten lectin-binding domains) fused with an antibody Fc domain. A nucleic acid and amino acid sequence of human DEC-205 is provided in PCT Patent Publication No WO 96023882 (Steinman). The antigen was mixed with Complete Freund's (Sigma) adjuvant for the first immunization. Thereafter, the antigen was mixed with Incomplete Freund's (Sigma). Additional mice were immunized with the soluble DEC-205 protein in RIBI MPL plus TDM adjuvant system (Sigma). 5-25 micrograms soluble recombinant DEC-205 antigen in PBS or $5 \times 10^6$ CHO cells transfected for surface expression of human DEC-205 in PBS were mixed 1:1 with the adjuvant. Mice were injected with 100 microliters of the prepared antigen into the peritoneal cavity every 14 days. Animals that developed anti-DEC-205 titers were given an iv injection of 10 micrograms soluble recombinant DEC-205 antigen three to four days prior to fusion. Mouse spleens were harvested, and the isolated splenocytes used for hybridoma preparation.

Hybridoma Preparation: The P3x63Ag8.653 murine myeloma cell line (ATCC CRL 1580) was used for the fusions. RPMI 1640 (Invitrogen) containing 10% FBS, and was used to culture the myeloma cells. Additional media supplements were added to the Hybridoma growth media, which included: 3% Origen-Hybridoma Cloning Factor (Igen), 10% FBS (Sigma), L-glutamine (Gibco) 0.1% gentamycin (Gibco), 2-mercaptoethanol (Gibco), HAT (Sigma; $1.0 \times 10^4$ M hypoxanthine, $4.0 \times 10^{-7}$ M aminopterin, $1.6 \times 10^{-5}$ M thymidine), or HT (Sigma; $1.0 \times 10^{-4}$ M hypoxanthine, $1.6 \times 10^{-5}$ M thymidine) media.

Spleen cells were mixed with the 653 myeloma cells in a 6:1 ratio and pelleted by centrifugation. Polyethylene glycol was added dropwise with careful mixing to facilitate fusion. Hybridomas were allowed to grow out for one to two weeks until visible colonies become established. Supernatant was harvested and used for initial screening for human IgG via ELISA using a human kappa chain specific capture and a human Fc specific detection. IgG positive supernatants were then assayed for DEC-205 specificity via flow cytometry or using a DEC-205 ELISA.

Hybridomas producing specific HuMab IgG were subcloned and expanded. The HuMabs produced were then purified by protein A column chromatography according to standard conditions which led to the isolation of a number of antibodies of particular interest.

Example 2

Determination of Affinity and Rate Constants of HuMabs by Surface Plasmon Resonance (SPR)

Binding affinity and binding kinetics of various human anti-DEC-205 antibodies from Example 1 were examined by Biacore™ surface plasmon resonance (SPR) analysis using a Biacore™ 2000 SPR instrument (Biacore AB, Uppsala, Sweden) according to the manufacturer's guidelines.

Purified recombinant human DEC-205 fusion (or control) protein was covalently linked to a Biacore™ CM5 sensor chip (carboxymethylated dextran covalently attached to a gold surface; Biacore Product No. BR-1000-14) using standard amine coupling chemistry with an Amine Coupling Kit provided by Biacore according to the manufacturer's guidelines (BIAcore Product No. BR-1000-50, comprising coupling reagents N-hydroxysuccinimide (NHS) and 1-Ethyl-3-(3-dimethylaminopropyl) carbodiimide hydrochloride (EDC)). Low levels of ligand were immobilised to limit any effects of mass transport of analyte on kinetic parameters, such that the $R_{MAX}$ observed was in the order of 200 RU.

Binding was measured by flowing the antibodies over the sensor chip in HBS-NP buffer (HBS-N buffer, Biacore Product No. BR-1003-69: 4-(2-hydroxyethyl)-1-piperazineethanesulfonic acid (HEPES) 0.24%, sodium chloride 0.88%, qs water, filtered/de-gassed and pre-equilibrated to room temperature with a 1:2000 dilution of Surfactant P20) at concentrations ranging from 1.25 to 200 nM and at a flow rate of 35 µl/minute. The antigen-antibody association and dissociation kinetics were followed for approximately 300 to 600 seconds in each case.

Corresponding controls were conducted in each case using an unrelated protein for "background" subtraction. A single injection of 18 mM NaOH for 17 seconds at 35 µl/min was used as the regeneration conditions throughout the study.

Biacore's kinetics wizard was used in each case to derive kinetic parameters from the concentration series of analyte diluted in HBS-NP running buffer. The association and dissociation curves were fitted to a 1:1 Langmuir binding model using Biacore™ kinetics wizard software (Biacore AB) according to the manufacturer's guidelines. The affinity and kinetic parameters (with background subtracted) as determined are shown in Table 1 below. For each antibody, the figures shown are the mean of two separate series of experiments, using separately prepared sensor chips in each case, (where ka=rate constant of association, kd=rate constant of dissociation, $K_D$=dissociation equilibrium constant (measure of affinity), $K_A$=association equilibrium constant, Rmax=maximum SPR response signal).

TABLE 1

| mAb # | mAb ID | ka (1/Ms) | kd (1/s) | $K_A$ (1/M) | $K_D$ (M) | RMax (RU) |
|---|---|---|---|---|---|---|
| #1 | 3A4-1C10 | $1.5 \times 10^6$ | $9.6 \times 10^{-5}$ | $1.6 \times 10^{10}$ | $6.6 \times 10^{-11}$ | 278 |
| #2 | 5A8-1F1 | $3.6 \times 10^5$ | $2.0 \times 10^{-4}$ | $2.1 \times 10^9$ | $1.5 \times 10^{-9}$ | 172 |
| #3 | 3C7-3A3 | $1.7 \times 10^5$ | $7.6 \times 10^{-4}$ | $5.2 \times 10^8$ | $5.6 \times 10^{-9}$ | 133 |
| #4 | 2D3-1F5 | $3.3 \times 10^5$ | $2.2 \times 10^{-5}$ | $1.5 \times 10^{10}$ | $6.8 \times 10^{-11}$ | 275 |
| #5 | 3D6-2F4 | $1.8 \times 10^6$ | $1.2 \times 10^{-4}$ | $1.5 \times 10^{10}$ | $8.0 \times 10^{-11}$ | 294 |
| #6 | 5D12-5G1 | $5.4 \times 10^5$ | $3.2 \times 10^{-4}$ | $2.0 \times 10^9$ | $7.0 \times 10^{-10}$ | 272 |
| #7 | 1G6-1G6 | $1.4 \times 10^6$ | $3.0 \times 10^{-4}$ | $4.7 \times 10^9$ | $2.3 \times 10^{-10}$ | 249 |
| #8 | 3G9-2D2 | $9.0 \times 10^5$ | $1.9 \times 10^{-4}$ | $4.7 \times 10^9$ | $2.4 \times 10^{-10}$ | 268 |

Example 3

Binding of HuMabs to Cells Expressing Human DEC-205

The ability of anti-DEC-205 HuMabs to bind to DEC-205 on CHO-S cells expressing human DEC-205 on their surface was investigated by flow cytometry as follows.

Antibodies were tested for binding to CHO-S cells expressing human DEC-205 on their surface. Protein A purified HuMabs 3D6-2F4, 3D6-4C8, 3G9-2D2, 5A8-1F1, 2D3-1F5-2A9, 3C7-3A3, 5D12-5G1, 1G6-1G6 and 3A4-1C10 were incubated with the CHO-S cells expressing human DEC-205, as well as CHO-S control cells at 4° C. All antibodies were used at saturating concentrations. After 1 hour, the cells were washed with PBS containing 0.1% BSA and 0.05% $NaN_3$ (PBA) and the bound antibodies were detected by incubating the cells with a PE labeled goat anti-human IgG Fc-specific probe, at 4° C. The excess probe was washed from the cells with PBA and the cell associated fluorescence was determined by analysis using a LSR™ instrument (BD Biosciences, NJ, USA) according to the manufacturer's directions. Results are shown in FIG. 1.

As shown in FIG. 1, the HuMabs demonstrated high level binding to CHO-S cells expressing human DEC-205. These data demonstrate that these antibodies bind efficiently and specifically to human DEC-205 expressed on live CHO-S cells compared to the control cells.

Example 4

Binding of HuMabs to Human Dendritic Cells

Human peripheral blood mononuclear cells (PBMCs) were obtained by density gradient centrifugation of Leukopak platelet apheresis preparations Monocytes were isolated by adherance to tissue culture flasks for two hours, and then differentiated into dendritic cells by incubation with 2 ng/ml GM-CSF and 10 ng/ml IL-4 in macrophage serum free media (Gibco) for 5 to 7 days.

The ability of anti-DEC-205 HuMabs to bind to DEC-205 on human dendritic cells prepared as above was investigated by flow cytometry as follows.

Figure 2:
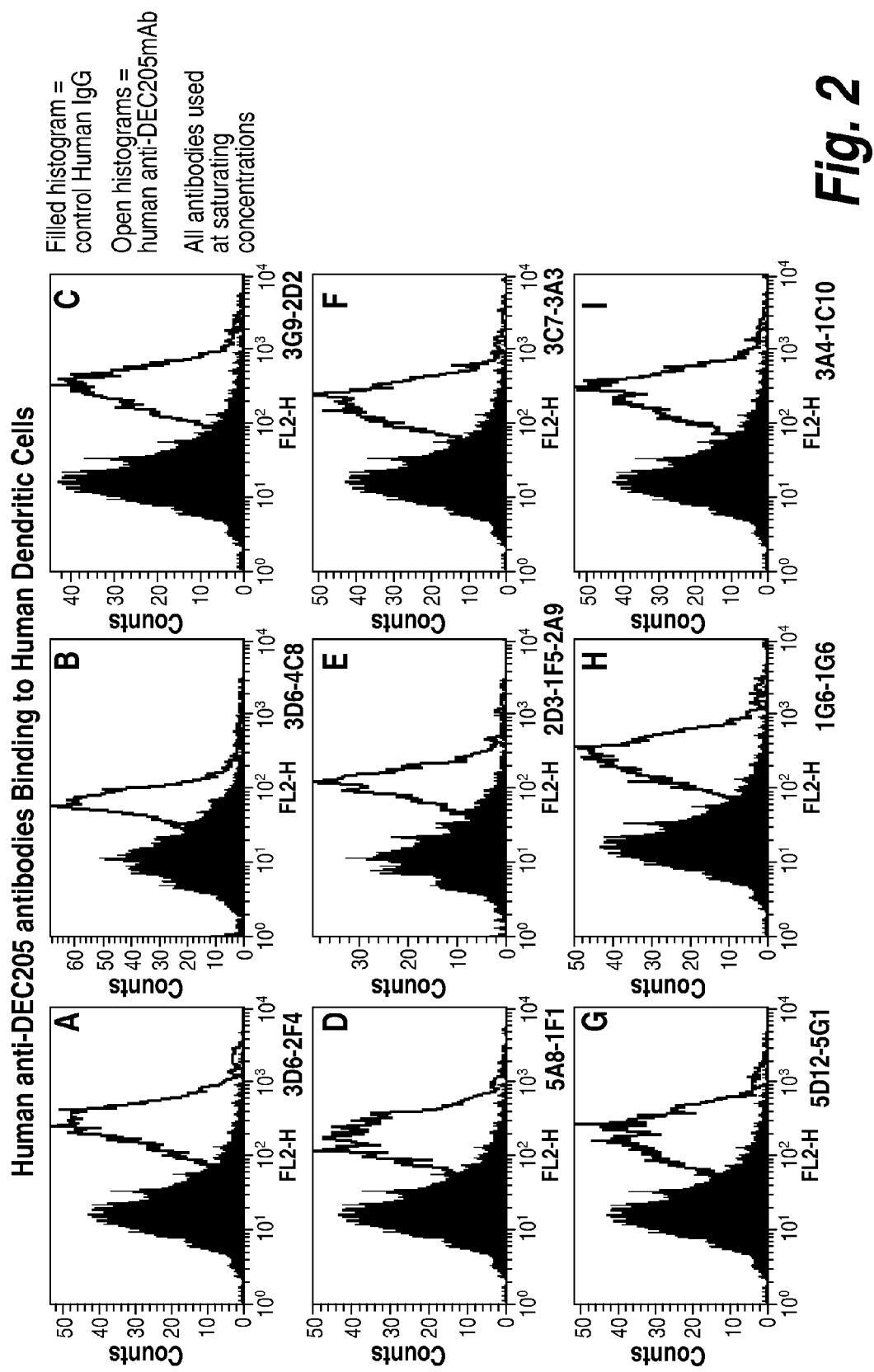
FIGS. 2A-2I include graphs showing the binding of human anti-DEC-205 antibodies (3D6-2F4, 3D6-4C8, 3G9-2D2, 5A8-1F1, 2D3-1F5-2A9, 3C7-3A3, 5D12-5G1, 1G6-1G6 and 3A4-1C10) to DEC-205 on human dendritic cells by flow cytometry.

Protein A purified HuMabs 3D6-2F2, 3D6-4C8, 3G9-2D2, 5A8-1F1, 2D3-1F5-2A9, 3C7-3A3, 5D12-5G1, 1G6-1G6 and 3A4-1C10, and an isotype control (human IgG) were incubated with the human dendritic cells at 4° C. All antibodies were used at saturating concentrations. After 1 hour, the cells were washed with PBS containing 0.1% BSA and 0.05% NaN$_3$ (PBA) and the bound antibodies were detected by incubating the cells with a PE labeled goat anti-human IgG Fc-specific probe, at 4° C. The excess probe was washed from the cells with PBA and the cell associated fluorescence was determined by analysis using a LSR instrument (BD Biosciences, NJ, USA) according to the manufacturer's directions. Results are shown in FIG. 2, which shows that the HuMabs demonstrated high level binding to human dendritic cells compared to the isotype control.

Example 5

ELISA Assay to Determine HuMAb Binding Characteristics on DEC-205

Figure 3:
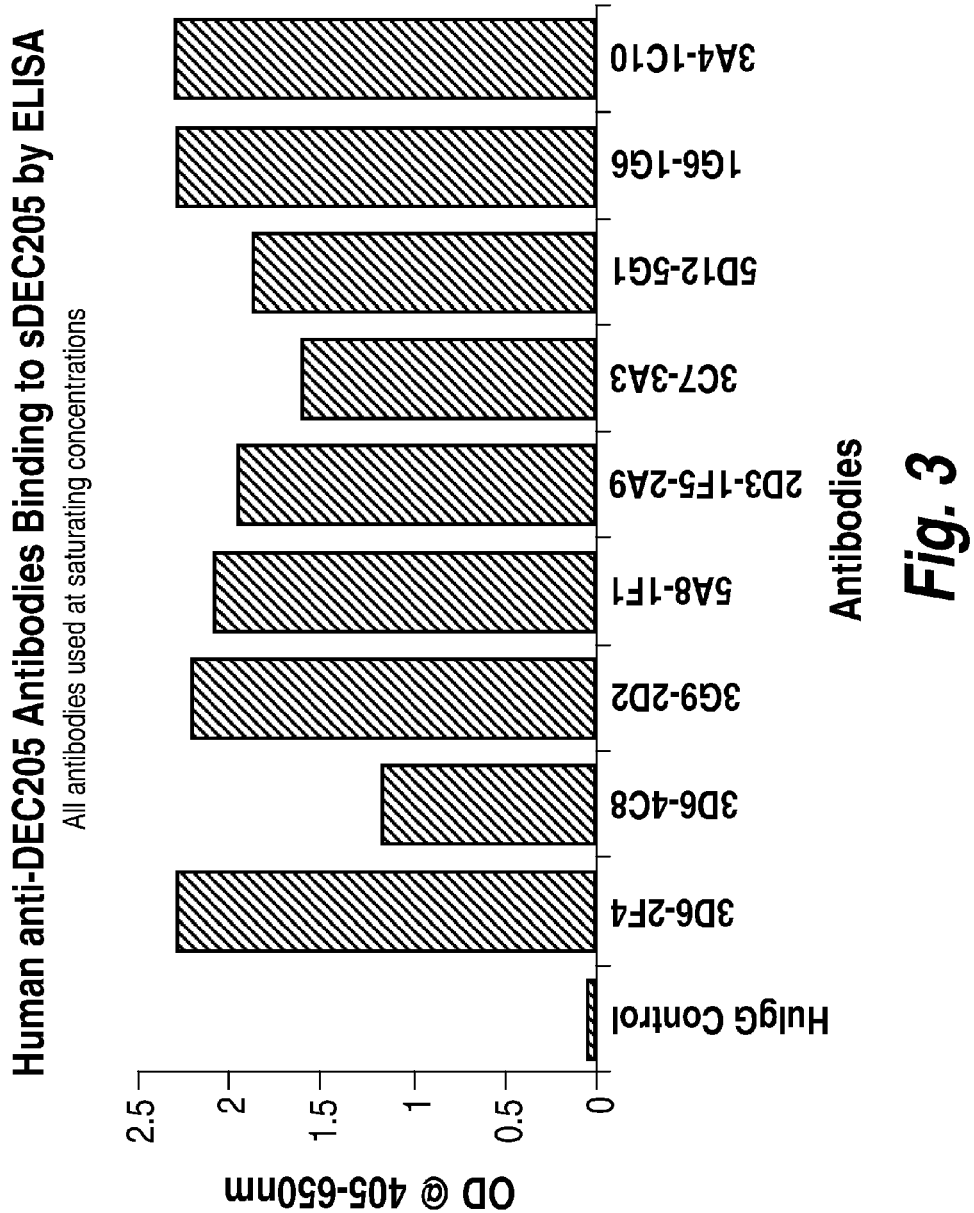
FIG. 3 is a graph showing the binding of human anti-DEC-205 antibodies (3D6-2F4, 3D6-4C8, 3G9-2D2, 5A8-1F1, 2D3-1F5-2A9, 3C7-3A3, 5D12-5G1, 1G6-1G6 and 3A4-1C10) to DEC-205 using ELISA.

Microtiter plates were coated with soluble DEC-205/Fc fusion protein in PBS, and then blocked with 5% bovine serum albumin in PBS. Protein A purified HuMabs and an isotype control were added at saturating concentrations and incubated at 37° C. The plates were washed with PBS/Tween and then incubated with a goat-anti-human IgG Fc-specific polyclonal reagent conjugated to alkaline phosphatase at 37° C. After washing, the plates were developed with pNPP substrate (1 mg/ml), and analyzed at OD 405-650 using a microtiter plate reader. Results are shown in FIG. 3, which shows that the HuMabs demonstrated high level binding compared to the isotype control.

Example 6

Antibody Internalization Assay

Figure 4:
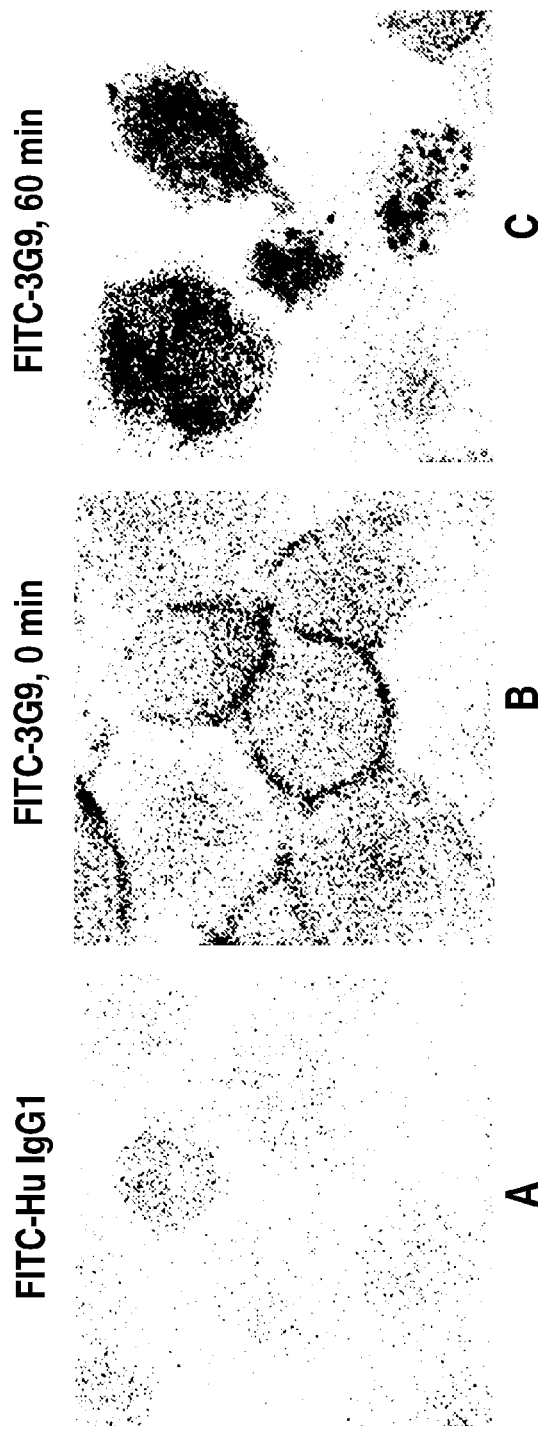
FIGS. 4A-4C show internalization into the dendritic cells of FITC-labelled HuMab (FITC-3G9-2D2) compared to the control (FITC-human IgG1) using confocal microscopy.

Human monocyte-derived dendritic cells $5 \times 10^5$ per aliquot were incubated with human IgG (1 mg/ml) to block non-specific binding. Cells were then incubated for 30 minutes on ice with 100 µg/ml of FITC-conjugated anti-Dec-205 HuMab 3G9-2D2 in blocking buffer for binding, and subsequently transferred to 37° C. for 0, 10, 30, 60 and 120 minutes for internalization. FITC-conjugated human IgG1 at same concentration was used as control. Cells were then washed and fixed with 1% paraformaldehyde. Fixed cells were washed, resuspended in water, and cytospun onto microscope slides. Images were taken with a Zeiss LSM 510 Meta confocal microscope. Results are shown in FIG. 4, which shows that the FITC-labelled HuMabs demonstrated efficient internalization into the dendritic cells compared to the control.

Example 7

Antibody Sequencing

As described above in Example 1, HuMabs from hybridomas producing specific HuMab IgG were purified by protein A column chromatography which led to the isolation of eight antibodies ("HuMabs") of particular interest. The $V_H$ and $V_L$ coding regions of HuMabs 3D6-2F4, 3D6-4C8, 3G9-2D2, 5A8-1F1, 2D3-1F5-2A9 ($V_H$ region), 3C7-3A3, 1E6-3D10 ($V_H$ region) and 5C3-2-3F6 were identified using RNA from the corresponding hybridomas. RNA was reverse transcribed to cDNA, the V coding regions were amplified by PCR and the PCR product was sequenced. The following are the nucleic and amino acid sequences of the $V_H$ and $V_L$ regions of the HuMabs (in the case of the amino acid sequences, the Complementarity Determining Regions (CDRs) are underlined).

```
3D6-2F4 V_H nucleic acid sequence (VH3, locus 3-33; JH4) (SEQ ID NO: 2):
atggagtttgggctgagctggttttcctcgttgctcttttaagaggtgtccagtgtcaggtgcagctggtggagtctgggggaggcgtg gtccagcctgggaggtccctgagactctcctgtgcagcgtctggattcatcttcagtatctatggcatgcactgggtccgccaggctcca ggcaaggggctggagtgggtggcagttatatggtatgatggaagtaataaatactatgcagactccgtgaagggccgattcaccatct ccagagacaattccaagaacacgctgtatctgcaaatgaacagcctgagagccgaggacacggctgtgtattactgtgcgagagctc ctcactttgactactggggccagggaaccctggtcaccgtctcctcagctagc 3D6-2F4 V_H amino acid sequence (SEQ ID NO: 3) including signal peptide:
MEFGLSWVFLVALLRGVQCQVQLVESGGGVVQPGRSLRLSCAASGFIFS<u>IYGMH</u>WV RQAPGKGLEWVA<u>VIWYDGSNKYYADSVKG</u>RFTISRDNSKNTLYLQMNSLRAEDTA VYYCAR<u>APHFDY</u>WGQGTLVTVSS 3D6-2F4 V_H "mature" amino acid sequence (SEQ ID NO: 4) excluding signal peptide:
QVQLVESGGGVVQPGRSLRLSCAASGFIFS<u>IYGMH</u>WVRQAPGKGLEWVA<u>VIWYDGS NKYYADSVKG</u>RFTISRDNSKNTLYLQMNSLRAEDTAVYYCAR<u>APHFDY</u>WGQGTLV

TVSS

3D6-2F4 V_HCDR1 (SEQ ID NO: 5): <u>IYGMH</u>

3D6-2F4 V_HCDR2 (SEQ ID NO: 6): <u>VIWYDGSNKYYADSVKG</u>

3D6-2F4 V_HCDR3 (SEQ ID NO: 7): <u>APHFDY</u>
```

3D6-2F4 V_L nucleic acid sequence (VK1, locus L15; JK2) (SEQ ID NO: 8):
atgggatggagctgtatcatcctgttcctcgtggccacagcaaccggtgtccactccgacatccagatgacccagtctccatcctcactg tctgcatctgttggagacagagtcaccatcacttgtcgggcgagtcagggtattagcagctggttagcctggtatcagcagaaaccaga gaaagcccctaagtccctgatctatgctgcatccagtttgcaaagtggggtcccatcaaggttcagcggcagtggatctgggacagatt tcactctcaccatcagcagcctgcagcctgaagattttgcaacttattactgccaacagtataatagttacccgtacacttttggccaggg gaccaagctggagatcaaacgtacg 3D6-2F4 V_L amino acid sequence (SEQ ID NO: 9) including signal peptide:
MDMRVLAQLLGLLLLCFPGARCDIQMTQSPSSLSASVGDRVTITC<u>RASQGISSWLA</u>W YQQKPEKAPKSLIY<u>AASSLQS</u>GVPSRFSGSGSGTDFTLTISSLQPEDFATYYC<u>QQYNSY PYTF</u>GQGTKLEIK 3D6-2F4 V_L "mature" amino acid sequence (SEQ ID NO: 10) excluding signal peptide:
DIQMTQSPSSLSASVGDRVTITC<u>RASQGISSWLA</u>WYQQKPEKAPKSLIY<u>AASSLQS</u>GV PSRFSGSGSGTDFTLTISSLQPEDFATYYC<u>QQYNSYPYT</u>FGQGTKLEIK 3D6-2F4 V_LCDR1 (SEQ ID NO: 11): <u>RASQGISSWLA</u>

3D6-2F4 V_LCDR2 (SEQ ID NO: 12): <u>AASSLQS</u>

3D6-2F4 V_LCDR3 (SEQ ID NO: 13): <u>QQYNSYPYT</u>

3D6-4C8 V_H nucleic acid sequence (VH3, locus 3-33; JH4) (SEQ ID NO: 14):
atggagtttgggctgagctgggttttcctcgttgctcttttaagaggtgtccagtgtcaggtgcagctggtggagtctgggggaggcgtg gtccagcctggggaggtccctgagactctcctgtgcagcgtctggattcatcttcagtatctatggcatgcactgggtccgccaggctcca ggcaaggggctggagtgggtggcagttatatggtatgatggaagtaataaatactatgcagactccgtgaagggccgattcaccatct ccagagacaattccaagaacacgctgtatctgcaaatgaacagcctgagagccgaggacacggctgtgtattactgtgcgagagctc ctcactttgactactggggccagggaaccctggtcaccgtctcctcagcctccaccaagggcccatcggtcttccccctggcac 3D6-4C8 V_H amino acid sequence (SEQ ID NO: 15) including signal peptide:
MEFGLSWVFLVALLRGVQCQVQLVESGGGVVQPGRSLRLSCAASGFIFS<u>IYGMH</u>WV RQAPGKGLEWVA<u>VIWYDGSNKYYADSVKG</u>RFTISRDNSKNTLYLQMNSLRAEDTA VYYCAR<u>APHFDY</u>WGQGTLVTVSS 3D6-4C8 V_H "mature" amino acid sequence (SEQ ID NO: 16) excluding signal peptide:
QVQLVESGGGVVQPGRSLRLSCAASGFIFS<u>IYGMH</u>WVRQAPGKGLEWVA<u>VIWYDGS NKYYADSVKG</u>RFTISRDNSKNTLYLQMNSLRAEDTAVYYCAR<u>APHFDY</u>WGQGTLV

TVSS

3D6-4C8 V_HCDR1 (SEQ ID NO: 17): <u>IYGMH</u>

3D6-4C8 V_HCDR2 (SEQ ID NO: 18): <u>VIWYDGSNKYYADSVKG</u>

3D6-4C8 V_HCDR3 (SEQ ID NO: 19): <u>APHFDY</u>

3D6-4C8 V_L nucleic acid sequence (VK1, locus L4; JK4) (SEQ ID NO: 20):
atggacatgagggtccccgctcagctcctggggcttctgctgctctggctcccaggtgccagatgtgccatccagttgacccagtctcc atcctccctgtctgcatctgtaggagacagagtcaccatcacttgccgggcaagtcagggcattagcagtgctttagcctggtatcagca gaaaccagggaaagctcctaagctcctgatctatgatgcctccagtttggaaagtggggtcccatcaaggttcagcggcagtggatct gggacagatttcactctcaccatcagcagcctgcagcctgaagattttgcaacttattactgtcaacagtttaatagttaccctctcactttc ggcggagggaccaaggtggagatcaaa 3D6-4C8 V_L amino acid sequence (SEQ ID NO: 21) including signal peptide:
MDMRVPAQLLGLLLLWLPGARCAIQLTQSPSSLSASVGDRVTITC<u>RASQGISSALA</u>W YQQKPGKAPKLLIY<u>DASSLES</u>GVPSRFSGSGSGTDFTLTISSLQPEDFATYYC<u>QQFNSY PLTF</u>GGGTKVEIK -continued 3D6-4C8 V_L "mature" amino acid sequence (SEQ ID NO: 22) excluding signal peptide:
AIQLTQSPSSLSASVGDRVTITC<u>RASQGISSALA</u>WYQQKPGKAPKLLIY<u>DASSLES</u>GVP SRFSGSGSGTDFTLTISSLQPEDFATYYC<u>QQFNSYPLT</u>FGGGTKVEIK 3D6-4C8 V_LCDR1 (SEQ ID NO: 23): <u>RASQGISSALA</u>

3D6-4C8 V_LCDR2 (SEQ ID NO: 24): <u>DASSLES</u>

3D6-4C8 V_LCDR3 (SEQ ID NO: 25): <u>QQFNSYPLT</u>

3G9-2D2, V_H nucleic acid sequence (VH3, locus 3-33; D undetermined; JH4) (SEQ ID NO: 26):
atggagtttgggctgagctgggttttcctcgttgctcttttaagaggtgtccagtgtcaggtgcagctggtggagtctgggggaggcgtg gtccagcctggggggtccctgagactctcctgtgcagcgtctggattcaccttcagtaattatggcatgtactgggtccgccaggctcca ggcaaggggctggagtgggtggcagttatatggtatgatggaagtaataaatactatgcagactccgtgaagggccgattcaccatctc ccagagacaattccaagaacacgctgtatctgcaaatgaacagcctgagagccgaggacacggctgtgtattactgtgcgagagatct ctggggatggtactttgactattggggccagggaaccctggtcaccgtctcctcagctagc 3G9-2D2, V_H amino acid sequence (SEQ ID NO: 27) including signal peptide:
MEFGLSWVFLVALLRGVQCQVQLVESGGGVVQPGRSLRLSCAASGFTFS<u>NYGMY</u>W VRQAPGKGLEWVA<u>VIWYDGSNKYYADSVKG</u>RFTISRDNSKNTLYLQMNSLRAEDT AVYYCAR<u>DLWGWYFDY</u>WGQGTLVTVSSASTKGPSVFPLA 3G9-2D2, V_H "mature" amino acid sequence (SEQ ID NO: 28) excluding signal peptide:
QVQLVESGGGVVQPGRSLRLSCAASGFTFS<u>NYGMY</u>WVRQAPGKGLEWVA<u>VIWYD</u>

<u>GSNKYYADSVKG</u>RFTISRDNSKNTLYLQMNSLRAEDTAVYYCAR<u>DLWGWYFDY</u>W

GQGTLVTVSSASTKGPSVFPLA

3G9-2D2, V_HCDR1 (SEQ ID NO: 29): <u>NYGMY</u>

3G9-2D2, V_HCDR2 (SEQ ID NO: 30): <u>VIWYDGSNKYYADSVKG</u>

3G9-2D2, V_HCDR3 (SEQ ID NO: 31): <u>DLWGWYFDY</u>

3G9-2D2, V_L nucleic acid sequence (VK3, locus L6; JK4) (SEQ ID NO: 32):
atgggatggagctgtatcatcctgttcctcgtggccacagcaaccggtgtccactccgaaattgtgttgacacagtctccagccaccctg tctttgtctccaggggaaagagccaccctctcctgcagggccagtcagagtgttagcagctacttagcctggtaccaacagaaacctg gccaggctcccaggctcctcatctatgatgcatccaacagggccactggcatcccagccaggttcagtggcagtgggtctgggacag acttcactctcaccatcagcagcctagagcctgaagattttgcagtttattactgtcagcagcgtcgcaactggccgctcactttcggcgg agggaccaaggtggagatcaaacgtacg 3G9-2D2, V_L amino acid sequence (SEQ ID NO: 33) including signal peptide:
MEAPAQLLFLLLLWLPDTTGEIVLTQSPATLSLSPGERATLSC<u>RASQSVSSYLA</u>WYQQ KPGQAPRLLIY<u>DASNRAT</u>GIPARFSGSGSGTDFTLTISSLEPEDFAVYYC<u>QQRRNWPL</u>

<u>T</u>FGGGTKVEIK

3G9-2D2, V_L "mature" amino acid sequence (SEQ ID NO: 34) excluding signal peptide:
EIVLTQSPATLSLSPGERATLSC<u>RASQSVSSYLA</u>WYQQKPGQAPRLLIY<u>DASNRAT</u>GIP ARFSGSGSGTDFTLTISSLEPEDFAVYYC<u>QQRRNWPLT</u>FGGGTKVEIK 3G9-2D2, V_LCDR1 (SEQ ID NO: 35): <u>RASQSVSSYLA</u>

3G9-2D2, V_LCDR2 (SEQ ID NO: 36): <u>DASNRAT</u>

3G9-2D2, V_LCDR3 (SEQ ID NO: 37): <u>QQRRNWPLT</u>

-continued

5A8-1F1, V<sub>H</sub> nucleic acid sequence (VH3, locus 3-33; JH2) (SEQ ID NO: 38):
atggagtttgggctgacctgggttttcctcgttgctcttttaagaggtgtccagtgtcaggtgcagctggtggagtctgggggaggcgtg gtccagcctggggaggtccctgagactctcctgtgcagcgtctggattcaccttcagtacctatggcatgcactgggtccgccaggctcc aggcaaggggctggagtgggtggcaattatatggtatgatggaggtaataaatactatgcagactccgtgaagggccgattcaccatc tccagagacaattccaagaacacgctgtatctgcaaatgaacagcctgagagccgaggacacggctgtgtattactgtgcgagagact tctactggtacttcgatctctggggccgtggcaccctggtcactgtctcctcagcctccaccaagggcccatcggtcttccccctggcaa gg 5A8-1F1, V<sub>H</sub> amino acid sequence (SEQ ID NO: 39) including signal peptide:
MEFGLTWVFLVALLRGVQCQVQLVESGGGVVQPGRSLRLSCAASGFTFS<u>TYGMH</u>W VRQAPGKGLEWVA<u>IIWYDGGNKYYADSVKG</u>RFTISRDNSKNTLYLQMNSLRAEDT AVYYCAR<u>DFYWYFDL</u>WGRGTLVTVSSASTKGPSVFPLA 5A8-1F1, V<sub>H</sub> "mature" amino acid sequence (SEQ ID NO: 40) excluding signal peptide:
QVQLVESGGGVVQPGRSLRLSCAASGFTFS<u>TYGMH</u>WVRQAPGKGLEWVA<u>IIWYDG</u>

<u>GNKYYADSVKG</u>RFTISRDNSKNTLYLQMNSLRAEDTAVYYCAR<u>DFYWYFDL</u>WGRG

TLVTVSSASTKGPSVFPLA

5A8-1F1, V<sub>H</sub>CDR1 (SEQ ID NO: 41): <u>TYGMH</u>

5A8-1F1, V<sub>H</sub>CDR2 (SEQ ID NO: 42): <u>IIWYDGGNKYYADSVKG</u>

5A8-1F1, V<sub>H</sub>CDR3 (SEQ ID NO: 43): <u>DFYWYFDL</u>

5A8-1F1, V<sub>L</sub> nucleic acid sequence (VK3, locus L6; JK1) (SEQ ID NO: 44):
atggaagcccccagctcagcttctcttcctcctgctactctggctcccagataccaccggagaaattgtgttgacacagtctccagccacc ctgtctttgtctccaggggaaagagccaccctctcctgcagggccagtcagagtgttagcagctacttagcctggtaccaacagaaacc tggccaggctcccaggctcctcatctatgatgcatccaacagggccactggcatcccagccaggttcagtggcagtgggtctgggac agacttcactctcaccatcagcagcctagagcctgaagattttgcagtttattactgtcagcagcgtaggacgttcggccaagggacca aggtggaaatcaaacga 5A8-1F1, V<sub>L</sub> amino acid sequence (SEQ ID NO: 45) including signal peptide:
MEAPAQLLFLLLLWLPDTTGEIVLTQSPATLSLSPGERATLSC<u>RASQSVSSYLA</u>WYQQ KPGQAPRLLIY<u>DASNRAT</u>GIPARFSGSGSGTDFTLTISSLEPEDFAVYYC<u>QQRRT</u>FGQG

TKVEIK

5A8-1F1, V<sub>L</sub> "mature" amino acid sequence (SEQ ID NO: 46) excluding signal peptide:
EIVLTQSPATLSLSPGERATLSC<u>RASQSVSSYLA</u>WYQQKPGQAPRLLIY<u>DASNRAT</u>GIP ARFSGSGSGTDFTLTISSLEPEDFAVYYC<u>QQRRT</u>FGQGTKVEIK 5A8-1F1, V<sub>L</sub>CDR1 (SEQ ID NO: 47): <u>RASQSVSSYLA</u>

5A8-1F1, V<sub>L</sub>CDR2 (SEQ ID NO: 48): <u>DASNRAT</u>

5A8-1F1, V<sub>L</sub>CDR3 (SEQ ID NO: 49): <u>QQRRT</u>

3C7-3A3, V<sub>H</sub> nucleic acid sequence (VH3, locus 3-33; JH2) (SEQ ID NO: 50):
atggagtttgggctgagctgggttttcctcgttgctcttttaagaggtgtccagtgtcaggtgcagctggtggagtctgggggaggcgtg gtccagcctggggaggtccctgagactctcctgtgcagcgtctggattcaccttcagtagctataacatgcactgggtccgccaggctcc aggcaaggggctggagtgggtggcatttatatggtatgatggaagtaataaatactatggagactccgtgaagggccgattcaccatct ccagagacaattccaaaaacacgctgtatctgcaaatgaacagcctgagagccgaggacacggctgtgtattactgtgcgagagaag agctggggatcggtggtacttcgatctctggggccgtggcaccctggtcactgtctcctcagcctccaccaagggcccatcggtcttc cccctggcac 3C7-3A3, V_H amino acid sequence (SEQ ID NO: 51) including signal peptide:
MEFGLSWVFLVALLRGVQCQVQLVESGGGVVQPGRSLRLSCAASGFTFS<u>SYNMH</u>W VRQAPGKGLEWVA<u>FIWYDGSNKYYGDSVKG</u>RFTISRDNSKNTLYLQMNSLRAEDT AVYYCAR<u>EELGIGWYFDL</u>WGRGTLVTVSSASTKGPSVFPLA 3C7-3A3, V_H "mature" amino acid sequence (SEQ ID NO: 52) excluding signal peptide:
QVQLVESGGGVVQPGRSLRLSCAASGFTFS<u>SYNMH</u>WVRQAPGKGLEWVA<u>FIWYDG</u>

<u>SNKYYGDSVKG</u>RFTISRDNSKNTLYLQMNSLRAEDTAVYYCAR<u>EELGIGWYFDL</u>WG

RGTLVTVSSASTKGPSVFPLA

3C7-3A3, V_HCDR1 (SEQ ID NO: 53): <u>SYNMH</u>

3C7-3A3, V_HCDR2 (SEQ ID NO: 54): <u>FIWYDGSNKYYGDSVKG</u>

3C7-3A3, V_HCDR3 (SEQ ID NO: 55): <u>EELGIGWYFDL</u>

3C7-3A3, V_L nucleic acid sequence (VK3, locus L6; JK1) (SEQ ID NO: 56):
atggaagccccagctcagcttctcttcctcctgctactctggctcccagataccaccggagaaattgtgttgacacagtctccagccacc ctgtctttgtctccaggggaaagagccaccctctcctgcagggccagtcagagtgttagcagctacttagcctggtaccaacagaaacc tggccaggctcccaggctcctcatctatgatgcatccaacagggccactggcatcccagccaggttcagtggcagtgggtctgggac agacttcactctcaccatcagcagcctagagcctgaagattttgcagtttattactgtcagcagcgtaggacgttcggccaagggacca aggtggaaatcaaacgaactgtggctgcaccatctgtcttcatcttcccgccatctgatgagcagttgaaatctggaactgcctctgttgt gtgcctgc 3C7-3A3, V_L amino acid sequence (SEQ ID NO: 57) including signal peptide:
MEAPAQLLFLLLLWLPDTTGEIVLTQSPATLSLSPGERATLSC<u>RASQSVSSYLA</u>WYQQ KPGQAPRLLIY<u>DASNRAT</u>GIPARFSGSGSGTDFTLTISSLEPEDFAVYYC<u>QQRRT</u>FGQG

TKVEIK

3C7-3A3, V_L "mature" amino acid sequence (SEQ ID NO: 58) excluding signal peptide:
EIVLTQSPATLSLSPGERATLSC<u>RASQSVSSYLA</u>WYQQKPGQAPRLLIY<u>DASNRAT</u>GIP ARFSGSGSGTDFTLTISSLEPEDFAVYYC<u>QQRRT</u>FGQGTKVEIK 3C7-3A3, V_LCDR1 (SEQ ID NO: 59): <u>RASQSVSSYLA</u>

3C7-3A3, V_LCDR2 (SEQ ID NO: 60): <u>DASNRAT</u>

3C7-3A3, V_LCDR3 (SEQ ID NO: 61): <u>QQRRT</u>

2D3-1F5-2A9, V_H nucleic acid sequence (VH3, locus Orph-C16; JH3) (SEQ ID NO: 62):
atggagtttgtgctgagctgggttctccttgttgctatattaaaaggtgtccagtgtgaggttcagctggtgcagtctgggggaggcttggt acatcctggggggtccctgagactctcctgtgcaggctctggattcaccttcagtaactatgctatgcactgggttcgccaggctccagg aaaaggtctggagtgggtatcaactattggtactggtggtggcacacctatgcagactccgtgaagggccgcttcaccatctccaga gacaatgccaagaactccttgtatcttcaaatgaacagcctgagagccgaggacatggctgtgtattactgtgcattaagtgcttttgatgt ctggggccaagggacaatggtcaccgtctcttcagcctccaccaagggcccatcggtcttccccctggcac 2D3-1F5-2A9, V_H amino acid sequence (SEQ ID NO: 63) including signal peptide:
MEFVLSWVLLVAILKGVQCEVQLVQSGGGLVHPGGSLRLSCAGSGFTFS<u>NYAMH</u>W VRQAPGKGLEWVS<u>TIGTGGGTPYADSVKG</u>RFTISRDNAKNSLYLQMNSLRAEDMAV YYCAL<u>SAFDV</u>WGQGTMVTVSSASTKGPSVFPLA 2D3-1F5-2A9, V_H "mature" amino acid sequence (SEQ ID NO: 64) excluding signal peptide:
EVQLVQSGGGLVHPGGSLRLSCAGSGFTFS<u>NYAMH</u>WVRQAPGKGLEWVS<u>TIGTGG</u>

<u>GTPYADSVKG</u>RFTISRDNAKNSLYLQMNSLRAEDMAVYYCAL<u>SAFDV</u>WGQGTMVT

VSSASTKGPSVFPLA

2D3-1F5-2A9, V_HCDR1 (SEQ ID NO: 65): <u>NYAMH</u>

2D3-1F5-2A9, V_HCDR2 (SEQ ID NO: 66): <u>TIGTGGGTPYADSVKG</u>

2D3-1F5-2A9, V_HCDR3 (SEQ ID NO: 67): <u>SAFDV</u>

-continued

1E6-3D10 V$_H$ nucleic acid sequence (VH3, locus Orph-HC16; JH4)
(SEQ ID NO: 68):
Atggagtttgtgctgagctgggttttccttgttgctatattaaaaggtgtccagtgtgaggttcagctggtgcagtctgggggaggcttgg tacatcctggggggtccctgagactctcctgtgcaggctctggattcaccttcagtagctatgctatgcactgggttcgccaggctccag gaaaaggtctggagtgggtatcagctattggtactggtggttacacatactatgtagactccgtgaagggccgattcaccatctccagag acaatgccaagaagtccttgtatcttcaaatgaacagcctgagagccgaggacatggctgtgtattactgtgcaagagagccgttttacg atattttgactggttattccccatactttgactactggggccagggaaccctggtcaccgtctcctcagcctccaccaagggcccatcggt cttccccctggcac 1E6-3D10 V$_H$ amino acid sequence (SEQ ID NO: 69) including signal peptide:
MEFVLSWVFLVAILKGVQCEVQLVQSGGGLVHPGGSLRLSCAGSGFTFS<u>SYAMH</u>WV RQAPGKGLEWVS<u>AIGTGGYTYYVDSVKG</u>RFTISRDNAKKSLYLQMNSLRAEDMAV YYCAR<u>EPFYDILTGYSPYFDY</u>WGQGTLVTVSS 1E6-3D10 V$_H$ "mature" amino acid sequence (SEQ ID NO: 70) excluding signal peptide:
EVQLVQSGGGLVHPGGSLRLSCAGSGFTFS<u>SYAMH</u>WVRQAPGKGLEWVS<u>AIGTGG</u>

<u>YTYYVDSVKG</u>RFTISRDNAKKSLYLQMNSLRAEDMAVYYCAR<u>EPFYDILTGYSPYF</u>

<u>DY</u>WGQGTLVTVSS

1E6-3D10 V$_H$CDR1: (SEQ ID NO: 71):<u>SYAMH</u>

1E6-3D10 V$_H$CDR2 (SEQ ID NO: 72): <u>AIGTGGYTYYVDSVKG</u>

1E6-3D10 V$_H$CDR3 (SEQ ID NO: 73): <u>EPFYDILTGYSPYFDY</u>

5C3-2-3F6 V$_H$ nucleic acid sequence (VH3, locus 3-33; JH2) (SEQ ID NO: 74):
Atggagtttgggctgagctgggttttcctcgttgctcttttaagaggtgtccagtgtcaggtgcagctggtggagtctgggggaggcgt ggtccagcctggggaggtccctgagactctcctgtgcagcgtctggattcaccttcagtagctataacatgcactgggtccgccaggctc caggcaaggggctggagtgggtggcagttatatggtatgatggaagtaataaatactatggagactccgtgaagggccgattcaccat ctccagagacaattccaagaacacgctgtatctgcaaatgaacagcctgagagccgaggacacggctgtgtattactgtgcgagaga agagctggggatcgggtggtacttcgatctctggggccgtggcaccctggtcactgtctcctcagcctccaccaagggcccatcggtc ttccccctggcac 5C3-2-3F6 V$_H$ amino acid sequence (SEQ ID NO: 75) including signal peptide:
MEFGLSWVFLVALLRGVQCQVQLVESGGGVVQPGRSLRLSCAASGFTFS<u>SYNMH</u>W VRQAPGKGLEWVA<u>VIWYDGSNKYYGDSVKG</u>RFTISRDNSKNTLYLQMNSLRAEDT AVYYCAR<u>EELGIGWYFDL</u>WGRGTLVTVSS 5C3-2-3F6 V$_H$ "mature" amino acid sequence (SEQ ID NO: 76) excluding signal peptide:
QVQLVESGGGVVQPGRSLRLSCAASGFTFS<u>SYNMH</u>WVRQAPGKGLEWVA<u>VIWYDG</u>

<u>SNKYYGDSVKG</u>RFTISRDNSKNTLYLQMNSLRAEDTAVYYCAR<u>EELGIGWYFDL</u>WG

RGTLVTVSS

5C3-2-3F6 V$_H$CDR1 (SEQ ID NO: 77): <u>SYNMH</u>

5C3-2-3F6 V$_H$CDR2 (SEQ ID NO: 78): <u>VIWYDGSNKYYGDSVKG</u>

5C3-2-3F6 V$_H$CDR3 (SEQ ID NO: 79): <u>EELGIGWYFDL</u>

5C3-2-3F6 VK V$_L$ nucleic acid sequence (VK1, locus L18; JK5) (SEQ ID NO: 80):
Atggacatgagggtccccgctcagctcctggggcttctgctgctctggctcccaggtgccagatgtgccatccagttgacccagtctc catcctccctgtctgcatctgtaggagacagagtcaccatcacttgccgggcaagtcagggcattagcagtgctttagcctggtatcagc agaaaccagggaaagctcctaagctcctgatctatgatgcctccagtttggaaagtggggtcccatcaaggttcagcggcagtggatct gggacagatttcactctcaccatcagcagcctgcagcctgaagattttgcaacttattactgtcaacagtttaatagtaccctcacttcgg ccaagggacacgactggagattaaacgaactgtggctgcaccatctgtcttcatcttcccgccatctgatgagcagttgaaatctggaa ctgcctctgttgtgtgcctgcaagggc 5C3-2-3F6 VK V<sub>L</sub> amino acid sequence (SEQ ID NO: 81) including signal peptide:
MDMRVPAQLLGLLLLWLPGARCAIQLTQSPSSLSASVGDRVTITC<u>RASQGISSALA</u>W YQQKPGKAPKLLIY<u>DASSLES</u>GVPSRFSGSGSGTDFTLTISSLQPEDFATYYC<u>QQFNSY</u>

<u>PH</u>FGQGTRLEIK

5C3-2-3F6 VK V<sub>L</sub> "mature" amino acid sequence (SEQ ID NO: 82) excluding signal peptide:
AIQLTQSPSSLSASVGDRVTITC<u>RASQGISSALA</u>WYQQKPGKAPKLLIY<u>DASSLES</u>GVP SRFSGSGSGTDFTLTISSLQPEDFATYYC<u>QQFNSYPH</u>FGQGTRLEIK 5C3-2-3F6 V<sub>L</sub>CDR1 (SEQ ID NO: 83): <u>RASQGISSALA</u>

5C3-2-3F6 V<sub>L</sub>CDR2 (SEQ ID NO: 84): <u>DASSLES</u>

5C3-2-3F6 V<sub>L</sub>CDR3 (SEQ ID NO: 85): <u>QQFNSYPH</u>

5D12-5G1 V<sub>H</sub> nucleic acid sequence (VH3, locus 3-33; JH2) (SEQ ID NO: 86):
Atggagtttgggctgagctgggttttcctcgttgctcttttaagaggtgtccagtgtcaggtgcagctggtggagtctgggggaggcgt ggtccagcctgggaggtccctgagactctcctgtgcagcgtctggattcaccttcagtagctatggcatgcactgggtccgccaggctc caggcaaggggctggagtgggtggcagttatatggtatgatggaagtaataaatactatgcagactccgtgaagggccgattcaccat ctccagagacaattccaagaacacgctgtatctgcaaatgaacagcctgagagccgaggacacggctgtgtattactgtgcgagagg ccccctcggtacttcgatctctggggccgtggcaccctggtcactgtctcctcagcctccaccaagggcccatcggtcttccccctgg cac 5D12-5G1 VH amino acid sequence (SEQ ID NO: 87) including signal peptide:
MEFGLSWVFLVALLRGVQCQVQLVESGGGVVQPGRSLRLSCAASGFTFS<u>SYGMHW</u>

VRQAPGKGLEWVA<u>VIWYDGSNKYYADSVKG</u>RFTISRDNSKNTLYLQMNSLRAEDT

AVYYCAR<u>GPPRYFDL</u>WGRGTLVTVSS

5D12-5G1 VH "mature" amino acid sequence (SEQ ID NO: 88) excluding signal peptide:
QVQLVESGGGVVQPGRSLRLSCAASGFTFS<u>SYGMH</u>WVRQAPGKGLEWVA<u>VIWYDG</u>

<u>SNKYYADSVKG</u>RFTISRDNSKNTLYLQMNSLRAEDTAVYYCAR<u>GPPRYFDL</u>WGRGT

LVTVSS

5D12-5G1 VH CDR1 (SEQ ID NO: 89): <u>SYGMH</u>

5D12-5G1 VH CDR2 (SEQ ID NO: 90): <u>VIWYDGSNKYYADSVKG</u>

5D12-5G1 VH CDR3 (SEQ ID NO: 91): <u>GPPRYFDL</u>

For reference, the amino acid sequences of the proposed corresponding germline sequences (assigned without prejudice) are as follows:

Germline L6 (SEQ ID NO: 92):
EIVLTQSPATLSLSPGERATLSCRASQSVSSYLAWYQQKPGQAPRLLIYD

ASNRATGIPARFSGSGSGTDFTLTISSLEPEDFAVYYCQQRSNWP

Germline L4 (SEQ ID NO: 93):
AIQLTQSPSSLSASVGDRVTITCRASQGISSALAWYQQKPGKAPKLLIYD

ASSLESGVPSRFSGSGSGTDFTLTISSLQPEDFATYYCQQFNSYP

Germline L15 (SEQ ID NO: 94):
DIQMTQSPSSLSASVGDRVTITCRARQGISSWLAWYQQKPEKAPKSLIYA

ASSLQSGVPSRFSGSGSGTDFTLTISSLQPEDFATYYCQQYNSYP

Germline V<sub>H</sub>3-33 (SEQ ID NO: 95):
QVQLVESGGGVVQPGRSLRLSCAASGFTFSSYGMHWVRQAPGKGLEWVAV

IVVYDGSNKYYADSVKGRFTISRDNSKNTLYLQMNSLRAEDTAVYYCAR

Germline Orph-C16 (SEQ ID NO: 96):
EVQLVQSGGGLVHPGGSLRLSCAGSGFTFSSYAMHWVRQAPGKGLEWV

SAIGTGGGTYYADSVKGRFTISRDNAKNSLYLQMNSLRAEDMAVYYCAR

Sequence alignments of the V<sub>L</sub> and V<sub>H</sub> sequences against the proposed corresponding germline sequences are shown in FIG. 5, for illustration purposes only.

Example 8

3G9-βhCG APC-Targeted Vaccine Conjugate

A DEC-205 targeted vaccine conjugate was generated by linking the βhCG antigen to HuMab 3G9-2D2 (also determined to be cross-reactive with cynomologous DEC-205) from Example 7 above. Linkage was accomplished by covalently attaching the antigen to the heavy chain of the antibody by genetic fusion.

A plasmid containing neomycin and dihydrofolate reductase genes was generated containing the βhCG coding sequence fused to antibody 3G9-2D2 heavy chain at the CH3 domain and the 3G9-2D2 light chain. The resulting plasmid construct was transfected into CHO cells using a standardized protocol (Qiagen Inc, Valencia, Calif.). Transfected cells were selected in media containing the antibiotic G418. After selection, the cells were cloned by limiting dilution, and stable clonal lines were used to generate cell banks for further studies. To confirm expression of the 3G9-βhCG constructs, Western Blot analysis of proteins run on SDS-PAGE under reducing and non-reducing conditions was performed. This fusion protein was observed to be of the expected molecular weight and to be properly assembled (i.e., to contain both the heavy chain fusion and the light chain). Specifically, the vaccine conjugate and the antibody alone were analyzed by SDS-PAGE using denaturing conditions and detected by Western blot analysis. The blot was then probed separately using goat anti-human IgG, and with a mAb (US Biologicals) specific to the βhCG C-terminal peptide. The results confirmed that the transformed CHO cells specifically expressed the 3G9-βhCG vaccine conjugate as evidenced by the appropriate size and composition of the fusion product.

Example 9

Antigen-Specific Activity Using 3G9-βhCG APC-Targeted Vaccine Conjugate

Cells capable of antigen presentation were human in origin and varied from peripheral blood mononuclear cells (PBMC), monocytes (THP-1), B lymphoblastoid cells (C1R.A2, 1518 B-LCL) and monocyte-derived DCs. All cells were positive for cell surface expression of DEC-205 as assessed by flow cytometry.

The vector pk: 3G9-hCGβ was transfected into CHO cells. Stable clones were selected with G418 and subsequently subcloned. The fusion protein produced by the cells (3G9-βhCG vaccine conjugate; Example 8) was collected in the supernatant and purified over Protein A column.

Figure 9A:
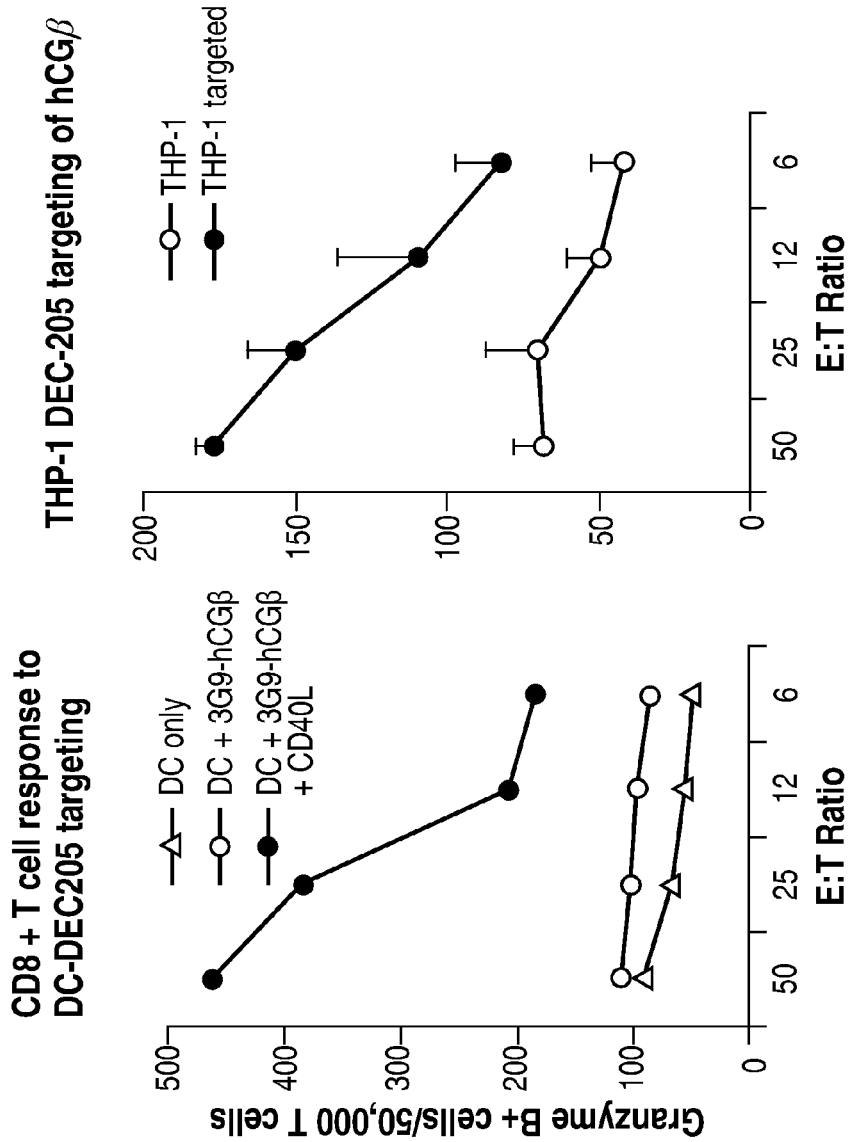
FIGS. 9A and B include graphs showing antigen-specific activity using 3G9-βhCG APC-targeted vaccine conjugate in peripheral blood mononuclear cells (PBMC), monocytes (THP-1), B lymphoblastoid cells (C1R.A2, 1518 B-LCL) and monocyte-derived DCs.
Figure 9B:
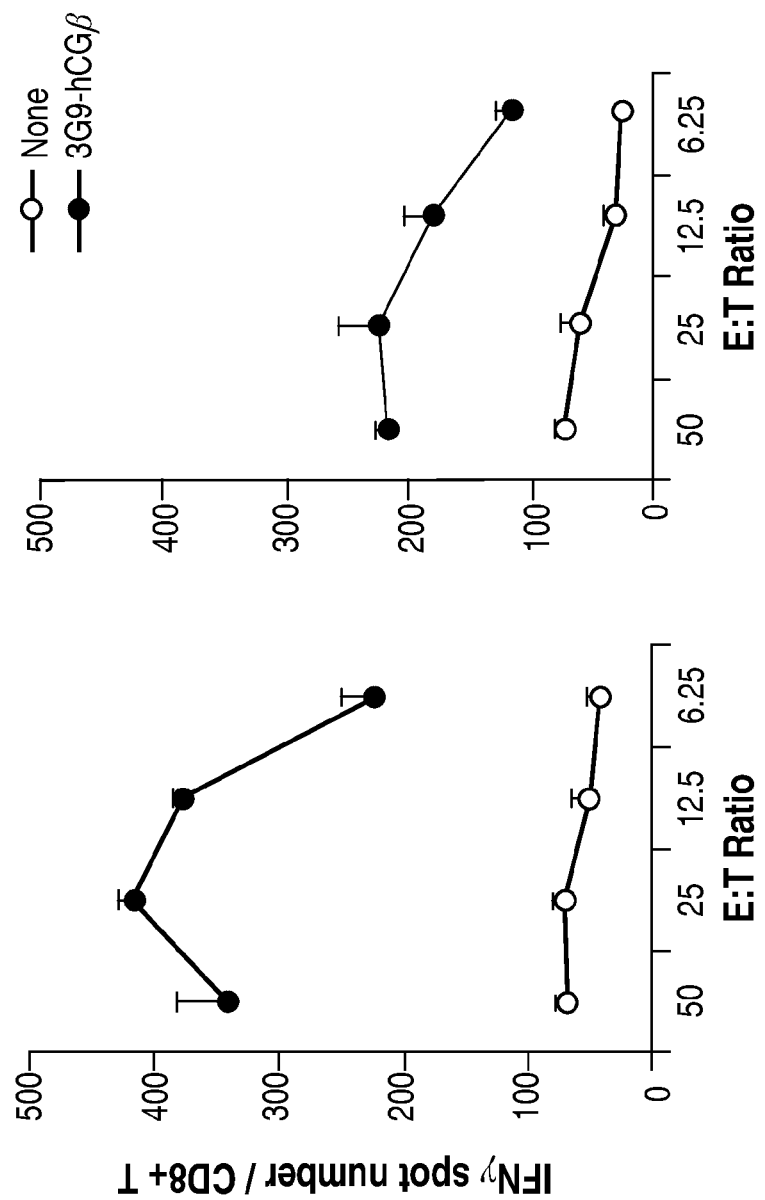

T cells were obtained from leukopacks of normal healthy donors. Antigen-specific T cells were generated in vitro by 2-3 weekly Stimulations with autologous DCs targeted with 3G9-hCGβ and enriched for CD8+ and CD4+ T cells before testing for antigen-specific activity with a variety of APCs (as described above) by GrB or IFNγ ELISpot assays (MabTech). Cytokines IL-7 and IL-2 were added to maintain effector propagation and activity every 3-4 days. Antigen-specific T cells were expanded on Miltenyi-MACS T cell expansion kit for 10-12 days in the presence of low dose of IL-2. CD40L (Alexis Biochemicals) was used to induce maturation of DCs. As shown in FIG. 9A, CD8+ T cell responses were achieved in DCs and monocytes (THP-1), as well as B lymphoblastoid cells (FIG. 9B). Accordingly, antigen targeting via the DEC-205 receptor to B cells resulted in the stimulation of MHC-class I restricted T cells.

EQUIVALENTS

Those skilled in the art will recognize, or be able to ascertain using no more than routine experimentation, many equivalents of the specific embodiments of the invention described herein. Such equivalents are intended to be encompassed by the following claims.

---

We claim:

1. An isolated nucleic acid encoding antibody heavy and light chain variable regions which bind human DEC-205 (SEQ ID NO:1) comprising CDR1, CDR2, and CDR3 amino acid sequences as follows:

(a) a heavy chain variable region CDR1 comprising SEQ ID NO: 29;
   a heavy chain variable region CDR2 comprising SEQ ID NO: 30;
   a heavy chain variable region CDR3 comprising SEQ ID NO: 31;
   a light chain variable region CDR1 comprising SEQ ID NO: 35;
   a light chain variable region CDR2 comprising SEQ ID NO: 36; and
   a light chain variable region CDR3 comprising SEQ ID NO: 37;

(b) a heavy chain variable region CDR1 comprising SEQ ID NO: 17;
   a heavy chain variable region CDR2 comprising SEQ ID NO: 18;
   a heavy chain variable region CDR3 comprising SEQ ID NO: 19;
   a light chain variable region CDR1 comprising SEQ ID NO: 23;
   a light chain variable region CDR2 comprising SEQ ID NO: 24; and
   a light chain variable region CDR3 comprising SEQ ID NO: 25;

(c) a heavy chain variable region CDR1 comprising SEQ ID NO: 5;
   a heavy chain variable region CDR2 comprising SEQ ID NO: 6;
   a heavy chain variable region CDR3 comprising SEQ ID NO: 7;
   a light chain variable region CDR1 comprising SEQ ID NO: 11;
   a light chain variable region CDR2 comprising SEQ ID NO: 12; and
   a light chain variable region CDR3 comprising SEQ ID NO: 13;

(d) a heavy chain variable region CDR1 comprising SEQ ID NO: 41;
   a heavy chain variable region CDR2 comprising SEQ ID NO: 42;
   a heavy chain variable region CDR3 comprising SEQ ID NO: 43;
   a light chain variable region CDR1 comprising SEQ ID NO: 47;
   a light chain variable region CDR2 comprising SEQ ID NO: 48; and
   a light chain variable region CDR3 comprising SEQ ID NO: 49;

(e) a heavy chain variable region CDR1 comprising SEQ ID NO: 53;
   a heavy chain variable region CDR2 comprising SEQ ID NO: 54;
   a heavy chain variable region CDR3 comprising SEQ ID NO: 55;
   a light chain variable region CDR1 comprising SEQ ID NO: 59;
   a light chain variable region CDR2 comprising SEQ ID NO: 60; and
   a light chain variable region CDR3 comprising SEQ ID NO: 61; or (f) a heavy chain variable region CDR1 comprising SEQ ID NO: 77;
   a heavy chain variable region CDR2 comprising SEQ ID NO: 78;
   a heavy chain variable region CDR3 comprising SEQ ID NO: 79;
   a light chain variable region CDR1 comprising SEQ ID NO: 83;
   a light chain variable region CDR2 comprising SEQ ID NO: 84; and
   a light chain variable region CDR3 comprising SEQ ID NO: 85.

2. An expression vector comprising the nucleic acid of claim 1.

3. A cell transformed with the expression vector of claim 2.

4. An isolated nucleic acid encoding antibody heavy and light chain variable regions comprising amino acid sequences as set forth in:
(a) SEQ ID NOs:28 and 34;
(b) SEQ ID NOs:4 and 10;
(c) SEQ ID NOs:16 and 22;
(d) SEQ ID NOs:40 and 46;
(e) SEQ ID NOs:52 and 58; or
(f) SEQ ID NOs:76 and 82.

5. An expression vector comprising the nucleic acid of claim 4.

6. A cell transformed with the expression vector of claim 5.

* * * * *

UNITED STATES PATENT AND TRADEMARK OFFICE
CERTIFICATE OF CORRECTION

| | | |
|---|---|---|
| PATENT NO. | : 8,586,720 B2 | Page 1 of 1 |
| APPLICATION NO. | : 13/542909 | |
| DATED | : November 19, 2013 | |
| INVENTOR(S) | : Tibor Keler et al. | |

It is certified that error appears in the above-identified patent and that said Letters Patent is hereby corrected as shown below:

On the Title Page, item (75) Inventors, correct the city of residence for inventor Laura A. Vitale from "Doyelstown, PA (US)" to --Doylestown, PA (US)--.

Signed and Sealed this

Eighteenth Day of March, 2014

Michelle K. Lee
*Deputy Director of the United States Patent and Trademark Office*

SEQUENCE LISTING

```
<160> NUMBER OF SEQ ID NOS: 106

<210> SEQ ID NO 1
<211> LENGTH: 1722
<212> TYPE: PRT
<213> ORGANISM: Homo sapiens

<400> SEQUENCE: 1

Met Arg Thr Gly Trp Ala Thr Pro Arg Arg Pro Ala Gly Leu Leu Met
1               5                   10                  15

Leu Leu Phe Trp Phe Phe Asp Leu Ala Glu Pro Ser Gly Arg Ala Ala
                20                  25                  30

Asn Asp Pro Phe Thr Ile Val His Gly Asn Thr Gly Lys Cys Ile Lys
            35                  40                  45

Pro Val Tyr Gly Trp Ile Val Ala Asp Asp Cys Asp Glu Thr Glu Asp
        50                  55                  60

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Arg Leu Ala Leu Lys Asp Gly
        115                 120                 125

His Gly Thr Ala Ile Ser Asn Ala Ser Asp Val Trp Lys Lys Gly Gly
    130                 135                 140

Ser Glu Glu Ser Leu Cys Asp Gln Pro Tyr His Glu Ile Tyr Thr Arg
145                 150                 155                 160
```

```
Asp Gly Asn Ser Tyr Gly Arg Pro Cys Glu Phe Pro Phe Leu Ile Asp
            165                 170                 175
Gly Thr Trp His His Asp Cys Ile Leu Asp Glu Asp His Ser Gly Pro
        180                 185                 190
Trp Cys Ala Thr Thr Leu Asn Tyr Glu Tyr Asp Arg Lys Trp Gly Ile
        195                 200                 205
Cys Leu Lys Pro Glu Asn Gly Cys Glu Asp Asn Trp Glu Lys Asn Glu
        210                 215                 220
Gln Phe Gly Ser Cys Tyr Gln Phe Asn Thr Gln Thr Ala Leu Ser Trp
225                 230                 235                 240
Lys Glu Ala Tyr Val Ser Cys Gln Asn Gln Gly Ala Asp Leu Leu Ser
                245                 250                 255
Ile Asn Ser Ala Ala Glu Leu Thr Tyr Leu Lys Glu Lys Glu Gly Ile
            260                 265                 270
Ala Lys Ile Phe Trp Ile Gly Leu Asn Gln Leu Tyr Ser Ala Arg Gly
        275                 280                 285
Trp Glu Trp Ser Asp His Lys Pro Leu Asn Phe Leu Asn Trp Asp Pro
        290                 295                 300
Asp Arg Pro Ser Ala Pro Thr Ile Gly Gly Ser Ser Cys Ala Arg Met
305                 310                 315                 320
Asp Ala Glu Ser Gly Leu Trp Gln Ser Phe Ser Cys Glu Ala Gln Leu
                325                 330                 335
Pro Tyr Val Cys Arg Lys Pro Leu Asn Asn Thr Val Glu Leu Thr Asp
            340                 345                 350
Val Trp Thr Tyr Ser Asp Thr Arg Cys Asp Ala Gly Trp Leu Pro Asn
        355                 360                 365
Asn Gly Phe Cys Tyr Leu Leu Val Asn Glu Ser Asn Ser Trp Asp Lys
        370                 375                 380
Ala His Ala Lys Cys Lys Ala Phe Ser Ser Asp Leu Ile Ser Ile His
385                 390                 395                 400
Ser Leu Ala Asp Val Glu Val Val Val Thr Lys Leu His Asn Glu Asp
                405                 410                 415
Ile Lys Glu Glu Val Trp Ile Gly Leu Lys Asn Ile Asn Ile Pro Thr
            420                 425                 430
Leu Phe Gln Trp Ser Asp Gly Thr Glu Val Thr Leu Thr Tyr Trp Asp
        435                 440                 445
Glu Asn Glu Pro Asn Val Pro Tyr Asn Lys Thr Pro Asn Cys Val Ser
        450                 455                 460
Tyr Leu Gly Glu Leu Gly Gln Trp Lys Val Gln Ser Cys Glu Glu Lys
465                 470                 475                 480
Leu Lys Tyr Val Cys Lys Arg Lys Gly Glu Lys Leu Asn Asp Ala Ser
                485                 490                 495
Ser Asp Lys Met Cys Pro Pro Asp Glu Gly Trp Lys Arg His Gly Glu
            500                 505                 510
Thr Cys Tyr Lys Ile Tyr Glu Asp Glu Val Pro Phe Gly Thr Asn Cys
        515                 520                 525
Asn Leu Thr Ile Thr Ser Arg Phe Glu Gln Glu Tyr Leu Asn Asp Leu
        530                 535                 540
Met Lys Lys Tyr Asp Lys Ser Leu Arg Lys Tyr Phe Trp Thr Gly Leu
545                 550                 555                 560
Arg Asp Val Asp Ser Cys Gly Glu Tyr Asn Trp Ala Thr Val Gly Gly
                565                 570                 575
Arg Arg Arg Ala Val Thr Phe Ser Asn Trp Asn Phe Leu Glu Pro Ala
            580                 585                 590
```

```
Ser Pro Gly Gly Cys Val Ala Met Ser Thr Gly Lys Ser Val Gly Lys
    595                 600                 605

Trp Glu Val Lys Asp Cys Arg Ser Phe Lys Ala Leu Ser Ile Cys Lys
    610                 615                 620

Lys Met Ser Gly Pro Leu Gly Pro Glu Ala Ser Pro Lys Pro Asp
625                 630                 635                 640

Asp Pro Cys Pro Glu Gly Trp Gln Ser Phe Pro Ala Ser Leu Ser Cys
                645                 650                 655

Tyr Lys Val Phe His Ala Glu Arg Ile Val Arg Lys Arg Asn Trp Glu
                660                 665                 670

Glu Ala Glu Arg Phe Cys Gln Ala Leu Gly Ala His Leu Ser Ser Phe
            675                 680                 685

Ser His Val Asp Glu Ile Lys Glu Phe Leu His Phe Leu Thr Asp Gln
    690                 695                 700

Phe Ser Gly Gln His Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Thr
                725                 730                 735

Ile Ile Met Pro Asn Glu Phe Gln Gln Asp Tyr Asp Ile Arg Asp Cys
                740                 745                 750

Ala Ala Val Lys Val Phe His Arg Pro Trp Arg Arg Gly Trp His Phe
            755                 760                 765

Tyr Asp Asp Arg Glu Phe Ile Tyr Leu Arg Pro Phe Ala Cys Asp Thr
    770                 775                 780

Lys Leu Glu Trp Val Cys Gln Ile Pro Lys Gly Arg Thr Pro Lys Thr
785                 790                 795                 800

Pro Asp Trp Tyr Asn Pro Asp Arg Ala Gly Ile His Gly Pro Leu
                805                 810                 815

Ile Ile Glu Gly Ser Glu Tyr Trp Phe Val Ala Asp Leu His Leu Asn
                820                 825                 830

Tyr Glu Glu Ala Val Leu Tyr Cys Ala Ser Asn His Ser Phe Leu Ala
    835                 840                 845

Thr Ile Thr Ser Phe Val Gly Leu Lys Ala Ile Lys Asn Lys Ile Ala
    850                 855                 860

Asn Ile Ser Gly Asp Gly Gln Lys Trp Trp Ile Arg Ile Ser Glu Trp
865                 870                 875                 880

Pro Ile Asp Asp His Phe Thr Tyr Ser Arg Tyr Pro Trp His Arg Phe
                885                 890                 895

Pro Val Thr Phe Gly Glu Glu Cys Leu Tyr Met Ser Ala Lys Thr Trp
                900                 905                 910

Leu Ile Asp Leu Gly Lys Pro Thr Asp Cys Ser Thr Lys Leu Pro Phe
                915                 920                 925

Ile Cys Glu Lys Tyr Asn Val Ser Ser Leu Lys Tyr Ser Pro Asp
    930                 935                 940

Ser Ala Ala Lys Val Gln Cys Ser Glu Gln Trp Ile Pro Phe Gln Asn
945                 950                 955                 960

Lys Cys Phe Leu Lys Ile Lys Pro Val Ser Leu Thr Phe Ser Gln Ala
                965                 970                 975

Ser Asp Thr Cys His Ser Tyr Gly Gly Thr Leu Pro Ser Val Leu Ser
            980                 985                 990

Gln Ile Glu Gln Asp Phe Ile Thr Ser Leu Leu Pro Asp Met Glu Ala
    995                 1000                1005

Thr Leu Trp Ile Gly Leu Arg Trp Thr Ala Tyr Glu Lys Ile Asn
    1010                1015                1020
```

-continued

```
Lys Trp Thr Asp Asn Arg Glu Leu Thr Tyr Ser Asn Phe His Pro
1025                1030                1035

Leu Leu Val Ser Gly Arg Leu Arg Ile Pro Glu Asn Phe Phe Glu
1040                1045                1050

Glu Glu Ser Arg Tyr His Cys Ala Leu Ile Leu Asn Leu Gln Lys
1055                1060                1065

Ser Pro Phe Thr Gly Thr Trp Asn Phe Thr Ser Cys Ser Glu Arg
1070                1075                1080

His Phe Val Ser Leu Cys Gln Lys Tyr Ser Glu Val Lys Ser Arg
1085                1090                1095

Gln Thr Leu Gln Asn Ala Ser Glu Thr Val Lys Tyr Leu Asn Asn
1100                1105                1110

Leu Tyr Lys Ile Ile Pro Lys Thr Leu Thr Trp His Ser Ala Lys
1115                1120                1125

Arg Glu Cys Leu Lys Ser Asn Met Gln Leu Val Ser Ile Thr Asp
1130                1135                1140

Pro Tyr Gln Gln Ala Phe Leu Ser Val Gln Ala Leu Leu His Asn
1145                1150                1155

Ser Ser Leu Trp Ile Gly Leu Phe Ser Gln Asp Asp Glu Leu Asn
1160                1165                1170

Phe Gly Trp Ser Asp Gly Lys Arg Leu His Phe Ser Arg Trp Ala
1175                1180                1185

Glu Thr Asn Gly Gln Leu Glu Asp Cys Val Val Leu Asp Thr Asp
1190                1195                1200

Gly Phe Trp Lys Thr Val Asp Cys Asn Asp Asn Gln Pro Gly Ala
1205                1210                1215

Ile Cys Tyr Tyr Ser Gly Asn Glu Thr Glu Lys Glu Val Lys Pro
1220                1225                1230

Val Asp Ser Val Lys Cys Pro Ser Pro Val Leu Asn Thr Pro Trp
1235                1240                1245

Ile Pro Phe Gln Asn Cys Cys Tyr Asn Phe Ile Ile Thr Lys Asn
1250                1255                1260

Arg His Met Ala Thr Thr Gln Asp Glu Val His Thr Lys Cys Gln
1265                1270                1275

Lys Leu Asn Pro Lys Ser His Ile Leu Ser Ile Arg Asp Glu Lys
1280                1285                1290

Glu Asn Asn Phe Val Leu Glu Gln Leu Leu Tyr Phe Asn Tyr Met
1295                1300                1305

Ala Ser Trp Val Met Leu Gly Ile Thr Tyr Arg Asn Asn Ser Leu
1310                1315                1320

Met Trp Phe Asp Lys Thr Pro Leu Ser Tyr Thr His Trp Arg Ala
1325                1330                1335

Gly Arg Pro Thr Ile Lys Asn Glu Lys Phe Leu Ala Gly Leu Ser
1340                1345                1350

Thr Asp Gly Phe Trp Asp Ile Gln Thr Phe Lys Val Ile Glu Glu
1355                1360                1365

Ala Val Tyr Phe His Gln His Ser Ile Leu Ala Cys Lys Ile Glu
1370                1375                1380

Met Val Asp Tyr Lys Glu Glu His Asn Thr Thr Leu Pro Gln Phe
1385                1390                1395

Met Pro Tyr Glu Asp Gly Ile Tyr Ser Val Ile Gln Lys Lys Val
1400                1405                1410

Thr Trp Tyr Glu Ala Leu Asn Met Cys Ser Gln Ser Gly Gly His
1415                1420                1425
```

| | | | | | | | | | |
|---|---|---|---|---|---|---|---|---|---|
| Leu | Ala | Ser | Val | His | Asn | Gln | Asn | Gly | Gln | Leu | Phe | Leu | Glu | Asp |
| | 1430 | | | | 1435 | | | | 1440 | |

| Ile | Val | Lys | Arg | Asp | Gly | Phe | Pro | Leu | Trp | Val | Gly | Leu | Ser | Ser |
| | 1445 | | | | 1450 | | | | 1455 | |

| His | Asp | Gly | Ser | Glu | Ser | Ser | Phe | Glu | Trp | Ser | Asp | Gly | Ser | Thr |
| | 1460 | | | | 1465 | | | | 1470 | |

| Phe | Asp | Tyr | Ile | Pro | Trp | Lys | Gly | Gln | Thr | Ser | Pro | Gly | Asn | Cys |
| | 1475 | | | | 1480 | | | | 1485 | |

| Val | Leu | Leu | Asp | Pro | Lys | Gly | Thr | Trp | Lys | His | Glu | Lys | Cys | Asn |
| | 1490 | | | | 1495 | | | | 1500 | |

| Ser | Val | Lys | Asp | Gly | Ala | Ile | Cys | Tyr | Lys | Pro | Thr | Lys | Ser | Lys |
| | 1505 | | | | 1510 | | | | 1515 | |

| Lys | Leu | Ser | Arg | Leu | Thr | Tyr | Ser | Ser | Arg | Cys | Pro | Ala | Ala | Lys |
| | 1520 | | | | 1525 | | | | 1530 | |

| Glu | Asn | Gly | Ser | Arg | Trp | Ile | Gln | Tyr | Lys | Gly | His | Cys | Tyr | Lys |
| | 1535 | | | | 1540 | | | | 1545 | |

| Ser | Asp | Gln | Ala | Leu | His | Ser | Phe | Ser | Glu | Ala | Lys | Lys | Leu | Cys |
| | 1550 | | | | 1555 | | | | 1560 | |

| Ser | Lys | His | Asp | His | Ser | Ala | Thr | Ile | Val | Ser | Ile | Lys | Asp | Glu |
| | 1565 | | | | 1570 | | | | 1575 | |

| Asp | Glu | Asn | Lys | Phe | Val | Ser | Arg | Leu | Met | Arg | Glu | Asn | Asn | Asn |
| | 1580 | | | | 1585 | | | | 1590 | |

| Ile | Thr | Met | Arg | Val | Trp | Leu | Gly | Leu | Ser | Gln | His | Ser | Val | Asp |
| | 1595 | | | | 1600 | | | | 1605 | |

| Gln | Ser | Trp | Ser | Trp | Leu | Asp | Gly | Ser | Glu | Val | Thr | Phe | Val | Lys |
| | 1610 | | | | 1615 | | | | 1620 | |

| Trp | Glu | Asn | Lys | Ser | Lys | Ser | Gly | Val | Gly | Arg | Cys | Ser | Met | Leu |
| | 1625 | | | | 1630 | | | | 1635 | |

| Ile | Ala | Ser | Asn | Glu | Thr | Trp | Lys | Lys | Val | Glu | Cys | Glu | His | Gly |
| | 1640 | | | | 1645 | | | | 1650 | |

| Phe | Gly | Arg | Val | Val | Cys | Lys | Val | Pro | Leu | Gly | Pro | Asp | Tyr | Thr |
| | 1655 | | | | 1660 | | | | 1665 | |

| Ala | Ile | Ala | Ile | Ile | Val | Ala | Thr | Leu | Ser | Ile | Leu | Val | Leu | Met |
| | 1670 | | | | 1675 | | | | 1680 | |

| Gly | Gly | Leu | Ile | Trp | Phe | Leu | Phe | Gln | Arg | His | Arg | Leu | His | Leu |
| | 1685 | | | | 1690 | | | | 1695 | |

| Ala | Gly | Phe | Ser | Ser | Val | Arg | Tyr | Ala | Gln | Gly | Val | Asn | Glu | Asp |
| | 1700 | | | | 1705 | | | | 1710 | |

| Glu | Ile | Met | Leu | Pro | Ser | Phe | His | Asp |
| | 1715 | | | | 1720 | |

<210> SEQ ID NO 2
<211> LENGTH: 408
<212> TYPE: DNA
<213> ORGANISM: Homo sapiens

<400> SEQUENCE: 2

```
atggagtttg ggctgagctg ggttttcctc gttgctcttt taagaggtgt ccagtgtcag    60
gtgcagctgg tggagtctgg gggaggcgtg gtccagcctg gaggtccct gagactctcc   120 tgtgcagcgt ctggattcat cttcagtatc tatggcatgc actgggtccg ccaggctcca   180
ggcaaggggc tggagtgggt ggcagttata tggtatgatg aagtaataa atactatgca   240 gactccgtga agggccgatt caccatctcc agagacaatt ccaagaacac gctgtatctg   300
```

```
caaatgaaca gcctgagagc cgaggacacg gctgtgtatt actgtgcgag agctcctcac    360
tttgactact ggggccaggg aaccctggtc accgtctcct cagctagc                 408
```

<210> SEQ ID NO 3
<211> LENGTH: 134
<212> TYPE: PRT
<213> ORGANISM: Homo sapiens

<400> SEQUENCE: 3

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ile Phe
        35                  40                  45

Ser Ile Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Pro His Phe Asp Tyr Trp Gly Gln Gly Thr
        115                 120                 125

Leu Val Thr Val Ser Ser
    130
```

<210> SEQ ID NO 4
<211> LENGTH: 115
<212> TYPE: PRT
<213> ORGANISM: Homo sapiens

<400> SEQUENCE: 4

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro His Phe Asp Tyr Trp Gly Gln Gly Thr Leu Val Thr
            100                 105                 110

Val Ser Ser
    115
```

<210> SEQ ID NO 5
<211> LENGTH: 5
<212> TYPE: PRT
<213> ORGANISM: Homo sapiens

<400> SEQUENCE: 5

Ile Tyr Gly Met His
1               5

<210> SEQ ID NO 6
<211> LENGTH: 17
<212> TYPE: PRT
<213> ORGANISM: Homo sapiens

<400> SEQUENCE: 6

Val Ile Trp Tyr Asp Gly Ser Asn Lys Tyr Tyr Ala Asp Ser Val Lys
1               5                   10                  15

Gly

<210> SEQ ID NO 7
<211> LENGTH: 6
<212> TYPE: PRT
<213> ORGANISM: Homo sapiens

<400> SEQUENCE: 7

Ala Pro His Phe Asp Tyr
1               5

<210> SEQ ID NO 8
<211> LENGTH: 384
<212> TYPE: DNA
<213> ORGANISM: Homo sapiens

<400> SEQUENCE: 8
atgggatgga gctgtatcat cctgttcctc gtggccacag caaccggtgt ccactccgac      60
atccagatga cccagtctcc atcctcactg tctgcatctg ttggagacag agtcaccatc     120
acttgtcggg cgagtcaggg tattagcagc tggttagcct ggtatcagca gaaaccagag     180
aaagccccta agtccctgat ctatgctgca tccagtttgc aaagtggggt cccatcaagg     240
ttcagcggca gtggatctgg gacagatttc actctcacca tcagcagcct gcagcctgaa     300
gattttgcaa cttattactg ccaacagtat aatagttacc cgtacacttt tggccagggg     360
accaagctgg agatcaaacg tacg                                            384

<210> SEQ ID NO 9
<211> LENGTH: 129
<212> TYPE: PRT
<213> ORGANISM: Homo sapiens

<400> SEQUENCE: 9

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Ser Ser Trp Leu Ala Trp Tyr Gln Gln Lys Pro Glu Lys
        50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

```
Ile Ser Ser Leu Gln Pro Glu Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
            115                 120                 125

Lys

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 11
<211> LENGTH: 11
<212> TYPE: PRT
<213> ORGANISM: Homo sapiens

<400> SEQUENCE: 11

Arg Ala Ser Gln Gly Ile Ser Ser Trp Leu Ala
1               5                   10

<210> SEQ ID NO 12
<211> LENGTH: 7
<212> TYPE: PRT
<213> ORGANISM: Homo sapiens

<400> SEQUENCE: 12

Ala Ala Ser Ser Leu Gln Ser
1               5

<210> SEQ ID NO 13
<211> LENGTH: 9
<212> TYPE: PRT
<213> ORGANISM: Homo sapiens

<400> SEQUENCE: 13

Gln Gln Tyr Asn Ser Tyr Pro Tyr Thr
1               5

<210> SEQ ID NO 14
<211> LENGTH: 439
<212> TYPE: DNA
<213> ORGANISM: Homo sapiens
```

-continued

<400> SEQUENCE: 14

```
atggagtttg ggctgagctg ggttttcctc gttgctcttt taagaggtgt ccagtgtcag    60
gtgcagctgg tggagtctgg gggaggcgtg gtccagcctg gaggtccct  gagactctcc   120
tgtgcagcgt ctggattcat cttcagtatc tatggcatgc actgggtccg ccaggctcca   180
ggcaaggggc tggagtgggt ggcagttata tggtatgatg gaagtaataa atactatgca   240
gactccgtga agggccgatt caccatctcc agagacaatt ccaagaacac gctgtatctg   300
caaatgaaca gcctgagagc cgaggacacg gctgtgtatt actgtgcgag agctcctcac   360
tttgactact ggggccaggg aaccctggtc accgtctcct cagcctccac caagggccca   420
tcggtcttcc ccctggcac                                                439
```

<210> SEQ ID NO 15
<211> LENGTH: 134
<212> TYPE: PRT
<213> ORGANISM: Homo sapiens

<400> SEQUENCE: 15

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ile Phe
        35                  40                  45

Ser Ile Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Pro His Phe Asp Tyr Trp Gly Gln Gly Thr
        115                 120                 125

Leu Val Thr Val Ser Ser
        130

<210> SEQ ID NO 16
<211> LENGTH: 115
<212> TYPE: PRT
<213> ORGANISM: Homo sapiens

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro His Phe Asp Tyr Trp Gly Gln Gly Thr Leu Val Thr
            100                 105                 110

Val Ser Ser
        115

<210> SEQ ID NO 17
<211> LENGTH: 5
<212> TYPE: PRT
<213> ORGANISM: Homo sapiens

<400> SEQUENCE: 17

Ile Tyr Gly Met His
1               5

<210> SEQ ID NO 18
<211> LENGTH: 17
<212> TYPE: PRT
<213> ORGANISM: Homo sapiens

<400> SEQUENCE: 18

Val Ile Trp Tyr Asp Gly Ser Asn Lys Tyr Tyr Ala Asp Ser Val Lys
1               5                   10                  15

Gly

<210> SEQ ID NO 19
<211> LENGTH: 6
<212> TYPE: PRT
<213> ORGANISM: Homo sapiens

<400> SEQUENCE: 19

Ala Pro His Phe Asp Tyr
1               5

<210> SEQ ID NO 20
<211> LENGTH: 387
<212> TYPE: DNA
<213> ORGANISM: Homo sapiens

<400> SEQUENCE: 20
atggacatga gggtccccgc tcagctcctg gggcttctgc tgctctggct cccaggtgcc      60
agatgtgcca tccagttgac ccagtctcca tcctccctgt ctgcatctgt aggagacaga    120
gtcaccatca cttgccgggc aagtcagggc attagcagtg ctttagcctg gtatcagcag    180
aaaccaggga agctcctaa gctcctgatc tatgatgcct ccagtttgga aagtggggtc     240
ccatcaaggt tcagcggcag tggatctggg acagatttca ctctcaccat cagcagcctg    300
cagcctgaag attttgcaac ttattactgt caacagttta atagttaccc tctcactttc    360
ggcggaggga ccaaggtgga gatcaaa                                         387

<210> SEQ ID NO 21
<211> LENGTH: 129
<212> TYPE: PRT
<213> ORGANISM: Homo sapiens

<400> SEQUENCE: 21

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

-continued

Leu Ser Ala Ser Val Gly Asp Arg Val Thr Ile Thr Cys Arg Ala Ser
            35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
        115                 120                 125

Lys

<210> SEQ ID NO 22
<211> LENGTH: 107
<212> TYPE: PRT
<213> ORGANISM: Homo sapiens

<400> SEQUENCE: 22

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 23
<211> LENGTH: 11
<212> TYPE: PRT
<213> ORGANISM: Homo sapiens

<400> SEQUENCE: 23

Arg Ala Ser Gln Gly Ile Ser Ser Ala Leu Ala
1               5                   10

<210> SEQ ID NO 24
<211> LENGTH: 7
<212> TYPE: PRT
<213> ORGANISM: Homo sapiens

<400> SEQUENCE: 24

Asp Ala Ser Ser Leu Glu Ser
1               5

<210> SEQ ID NO 25
<211> LENGTH: 9
<212> TYPE: PRT
<213> ORGANISM: Homo sapiens

<400> SEQUENCE: 25

Gln Gln Phe Asn Ser Tyr Pro Leu Thr
1               5

<210> SEQ ID NO 26
<211> LENGTH: 417
<212> TYPE: DNA
<213> ORGANISM: Homo sapiens

<400> SEQUENCE: 26

```
atggagtttg ggctgagctg ggttttcctc gttgctcttt taagaggtgt ccagtgtcag    60
gtgcagctgg tggagtctgg gggaggcgtg gtccagcctg ggaggtccct gagactctcc   120
tgtgcagcgt ctggattcac cttcagtaat tatggcatgt actgggtccg ccaggctcca   180
ggcaaggggc tggagtgggt ggcagttata tggtatgatg gaagtaataa atactatgca   240
gactccgtga agggccgatt caccatctcc agagacaatt ccaagaacac gctgtatctg   300
caaatgaaca gcctgagagc cgaggacacg gctgtgtatt actgtgcgag agatctctgg   360
ggatggtact ttgactattg gggccaggga accctggtca ccgtctcctc agctagc     417
```

<210> SEQ ID NO 27
<211> LENGTH: 149
<212> TYPE: PRT
<213> ORGANISM: Homo sapiens

<400> SEQUENCE: 27

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Asn Tyr Gly Met Tyr Trp Val Arg Gln Ala Pro Gly Lys Gly Leu
        50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Leu Trp Gly Trp Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala
145

<210> SEQ ID NO 28
<211> LENGTH: 130
<212> TYPE: PRT
<213> ORGANISM: Homo sapiens

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met Tyr Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Trp Gly Trp Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala
    130

<210> SEQ ID NO 29
<211> LENGTH: 5
<212> TYPE: PRT
<213> ORGANISM: Homo sapiens

<400> SEQUENCE: 29

Asn Tyr Gly Met Tyr
1               5

<210> SEQ ID NO 30
<211> LENGTH: 17
<212> TYPE: PRT
<213> ORGANISM: Homo sapiens

<400> SEQUENCE: 30

Val Ile Trp Tyr Asp Gly Ser Asn Lys Tyr Tyr Ala Asp Ser Val Lys
1               5                   10                  15

Gly

<210> SEQ ID NO 31
<211> LENGTH: 9
<212> TYPE: PRT
<213> ORGANISM: Homo sapiens

<400> SEQUENCE: 31

Asp Leu Trp Gly Trp Tyr Phe Asp Tyr
1               5

<210> SEQ ID NO 32
<211> LENGTH: 384
<212> TYPE: DNA
<213> ORGANISM: Homo sapiens

<400> SEQUENCE: 32
atgggatgga gctgtatcat cctgttcctc gtggccacag caaccggtgt ccactccgaa      60
attgtgttga cacagtctcc agccaccctg tctttgtctc caggggaaag agccaccctc     120
tcctgcaggg ccagtcagag tgttagcagc tacttagcct ggtaccaaca gaaacctggc     180
caggctccca ggctcctcat ctatgatgca tccaacaggg ccactggcat cccagccagg     240
ttcagtggca gtgggtctgg gacagacttc actctcacca tcagcagcct agagcctgaa     300
gattttgcag tttattactg tcagcagcgt cgcaactggc cgctcacttt cggcggaggg     360
accaaggtgg agatcaaacg tacg                                            384

```
<210> SEQ ID NO 33
<211> LENGTH: 127
<212> TYPE: PRT
<213> ORGANISM: Homo sapiens

<400> SEQUENCE: 33

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Arg
            100                 105                 110

Asn Trp Pro Leu Thr Phe Gly Gly Gly Thr Lys Val Glu Ile Lys
        115                 120                 125

<210> SEQ ID NO 34
<211> LENGTH: 107
<212> TYPE: PRT
<213> ORGANISM: Homo sapiens

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Pro Leu
                85                  90                  95

Thr Phe Gly Gly Gly Thr Lys Val Glu Ile Lys
            100                 105

<210> SEQ ID NO 35
<211> LENGTH: 11
<212> TYPE: PRT
<213> ORGANISM: Homo sapiens

<400> SEQUENCE: 35

Arg Ala Ser Gln Ser Val Ser Ser Tyr Leu Ala
1               5                   10

<210> SEQ ID NO 36
<211> LENGTH: 7
<212> TYPE: PRT
<213> ORGANISM: Homo sapiens
```

-continued

<400> SEQUENCE: 36

Asp Ala Ser Asn Arg Ala Thr
1               5

<210> SEQ ID NO 37
<211> LENGTH: 9
<212> TYPE: PRT
<213> ORGANISM: Homo sapiens

<400> SEQUENCE: 37

Gln Gln Arg Arg Asn Trp Pro Leu Thr
1               5

<210> SEQ ID NO 38
<211> LENGTH: 447
<212> TYPE: DNA
<213> ORGANISM: Homo sapiens

<400> SEQUENCE: 38
atggagtttg ggctgacctg ggttttcctc gttgctcttt taagaggtgt ccagtgtcag      60
gtgcagctgg tggagtctgg gggaggcgtg gtccagcctg gaggtccct gagactctcc     120 tgtgcagcgt ctggattcac cttcagtacc tatggcatgc actgggtccg ccaggctcca    180
ggcaaggggc tggagtgggt ggcaattata tggtatgatg gaagtaataa atactatgca    240
gactccgtga aggccgatt caccatctcc agagacaatt ccaagaacac gctgtatctg    300
caaatgaaca gcctgagagc cgaggacacg gctgtgtatt actgtgcgag agacttctac    360
tggtacttcg atctctgggg ccgtggcacc ctggtcactg tctcctcagc ctccaccaag    420
ggcccatcgg tcttcccccct ggcaagg                                        447

<210> SEQ ID NO 39
<211> LENGTH: 148
<212> TYPE: PRT
<213> ORGANISM: Homo sapiens

<400> SEQUENCE: 39

Met Glu Phe Gly Leu Thr Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Thr Tyr Gly Met His Trp Val Arg Gln Ala Pro Gly Lys Gly Leu
        50                  55                  60

Glu Trp Val Ala Ile Ile Trp Tyr Asp Gly Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Phe Tyr Trp Tyr Phe Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala
145

```
<210> SEQ ID NO 40
<211> LENGTH: 129
<212> TYPE: PRT
<213> ORGANISM: Homo sapiens

<400> SEQUENCE: 40

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Tyr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala

<210> SEQ ID NO 41
<211> LENGTH: 5
<212> TYPE: PRT
<213> ORGANISM: Homo sapiens

<400> SEQUENCE: 41

Thr Tyr Gly Met His
1               5

<210> SEQ ID NO 42
<211> LENGTH: 17
<212> TYPE: PRT
<213> ORGANISM: Homo sapiens

<400> SEQUENCE: 42

Ile Ile Trp Tyr Asp Gly Gly Asn Lys Tyr Tyr Ala Asp Ser Val Lys
1               5                   10                  15

Gly

<210> SEQ ID NO 43
<211> LENGTH: 8
<212> TYPE: PRT
<213> ORGANISM: Homo sapiens

<400> SEQUENCE: 43

Asp Phe Tyr Trp Tyr Phe Asp Leu
1               5

<210> SEQ ID NO 44
<211> LENGTH: 372
<212> TYPE: DNA
<213> ORGANISM: Homo sapiens

<400> SEQUENCE: 44
atggaagccc cagctcagct tctcttcctc ctgctactct ggctcccaga taccaccgga      60
gaaattgtgt tgacacagtc tccagccacc ctgtctttgt ctccagggga aagagccacc    120
```

```
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtaggacgt tcggccaagg gaccaaggtg    360
gaaatcaaac ga                                                       372
```

<210> SEQ ID NO 45
<211> LENGTH: 123
<212> TYPE: PRT
<213> ORGANISM: Homo sapiens

<400> SEQUENCE: 45

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Arg
            100                 105                 110

Thr Phe Gly Gln Gly Thr Lys Val Glu Ile Lys
        115                 120
```

<210> SEQ ID NO 46
<211> LENGTH: 103
<212> TYPE: PRT
<213> ORGANISM: Homo sapiens

<400> SEQUENCE: 46

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Thr Phe Gly Gln
                85                  90                  95

Gly Thr Lys Val Glu Ile Lys
            100
```

<210> SEQ ID NO 47
<211> LENGTH: 11
<212> TYPE: PRT
<213> ORGANISM: Homo sapiens -continued

```
<400> SEQUENCE: 47

Arg Ala Ser Gln Ser Val Ser Ser Tyr Leu Ala
1               5                   10

<210> SEQ ID NO 48
<211> LENGTH: 7
<212> TYPE: PRT
<213> ORGANISM: Homo sapiens

<400> SEQUENCE: 48

Asp Ala Ser Asn Arg Ala Thr
1               5

<210> SEQ ID NO 49
<211> LENGTH: 5
<212> TYPE: PRT
<213> ORGANISM: Homo sapiens

<400> SEQUENCE: 49

Gln Gln Arg Arg Thr
1               5

<210> SEQ ID NO 50
<211> LENGTH: 454
<212> TYPE: DNA
<213> ORGANISM: Homo sapiens

<400> SEQUENCE: 50
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtagc tataacatgc actgggtccg ccaggctcca     180
ggcaaggggc tggagtgggt ggcatttata tggtatgatg aagtaataa atactatgga      240 gactccgtga agggccgatt caccatctcc agagacaatt ccaaaaacac gctgtatctg     300
caaatgaaca gcctgagagc cgaggacacg gctgtgtatt actgtgcgag agaagagctg     360
gggatcgggg ggtacttcga tctctggggc cgtggcaccc tggtcactgt ctcctcagcc     420
tccaccaagg gcccatcggt cttccccctg gcac                                 454

<210> SEQ ID NO 51
<211> LENGTH: 151
<212> TYPE: PRT
<213> ORGANISM: Homo sapiens

<400> SEQUENCE: 51

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Asn Met His Trp Val Arg Gln Ala Pro Gly Lys Gly Leu
    50                  55                  60

Glu Trp Val Ala Phe Ile Trp Tyr Asp Gly Ser Asn Lys Tyr Tyr Gly
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

Tyr Tyr Cys Ala Arg Glu Glu Leu Gly Ile Gly Trp Tyr Phe Asp Leu
            115                 120                 125

Trp Gly Arg Gly Thr Leu Val Thr Val Ser Ser Ala Ser Thr Lys Gly
        130                 135                 140

Pro Ser Val Phe Pro Leu Ala
145                 150

<210> SEQ ID NO 52
<211> LENGTH: 132
<212> TYPE: PRT
<213> ORGANISM: Homo sapiens

<400> SEQUENCE: 52

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asn Met His Trp Val Arg Gln Ala Pro Gly Lys Gly Leu Glu Trp Val
        35                  40                  45

Ala Phe Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Leu Gly Ile Gly Trp Tyr Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala
    130

<210> SEQ ID NO 53
<211> LENGTH: 5
<212> TYPE: PRT
<213> ORGANISM: Homo sapiens

<400> SEQUENCE: 53

Ser Tyr Asn Met His
1               5

<210> SEQ ID NO 54
<211> LENGTH: 17
<212> TYPE: PRT
<213> ORGANISM: Homo sapiens

<400> SEQUENCE: 54

Phe Ile Trp Tyr Asp Gly Ser Asn Lys Tyr Tyr Gly Asp Ser Val Lys
1               5                   10                  15

Gly

<210> SEQ ID NO 55
<211> LENGTH: 11
<212> TYPE: PRT
<213> ORGANISM: Homo sapiens

<400> SEQUENCE: 55

Glu Glu Leu Gly Ile Gly Trp Tyr Phe Asp Leu
1               5                   10

<210> SEQ ID NO 56
<211> LENGTH: 454
<212> TYPE: DNA
<213> ORGANISM: Homo sapiens

<400> SEQUENCE: 56

```
atggaagccc cagctcagct tctcttcctc ctgctactct ggctcccaga taccaccgga      60
gaaattgtgt tgacacagtc tccagccacc ctgtctttgt ctccagggga agagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtaggacgt tcggccaagg gaccaaggtg     360
gaaatcaaac gaactgtggc tgcaccatct gtcttcatct tcccgccatc tgatgagcag     420
ttgaaatctg gaactgcctc tgttgtgtgc ctgc                                 454
```

<210> SEQ ID NO 57
<211> LENGTH: 123
<212> TYPE: PRT
<213> ORGANISM: Homo sapiens

<400> SEQUENCE: 57

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Arg
            100                 105                 110

Thr Phe Gly Gln Gly Thr Lys Val Glu Ile Lys
        115                 120
```

<210> SEQ ID NO 58
<211> LENGTH: 103
<212> TYPE: PRT
<213> ORGANISM: Homo sapiens

<400> SEQUENCE: 58

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Thr Phe Gly Gln
                85                  90                  95

Gly Thr Lys Val Glu Ile Lys
            100

<210> SEQ ID NO 59
<211> LENGTH: 11
<212> TYPE: PRT
<213> ORGANISM: Homo sapiens

<400> SEQUENCE: 59

Arg Ala Ser Gln Ser Val Ser Ser Tyr Leu Ala
1               5                   10

<210> SEQ ID NO 60
<211> LENGTH: 7
<212> TYPE: PRT
<213> ORGANISM: Homo sapiens

<400> SEQUENCE: 60

Asp Ala Ser Asn Arg Ala Thr
1               5

<210> SEQ ID NO 61
<211> LENGTH: 5
<212> TYPE: PRT
<213> ORGANISM: Homo sapiens

<400> SEQUENCE: 61

Gln Gln Arg Arg Thr
1               5

<210> SEQ ID NO 62
<211> LENGTH: 433
<212> TYPE: DNA
<213> ORGANISM: Homo sapiens

<400> SEQUENCE: 62
atggagtttg tgctgagctg ggttctcctt gttgctatat taaaaggtgt ccagtgtgag      60
gttcagctgg tgcagtctgg ggaggcttg gtacatcctg gggggtccct gagactctcc     120
tgtgcaggct ctggattcac cttcagtaac tatgctatgc actgggttcg ccaggctcca    180
ggaaaaggtc tggagtgggt atcaactatt ggtactggtg gtgcacacc ctatgcagac     240 tccgtgaagg gccgcttcac catctccaga gacaatgcca gaaactcctt gtatcttcaa    300
atgaacagcc tgagagccga ggacatggct gtgtattact gtgcattaag tgcttttgat    360
gtctggggcc aagggacaat ggtcaccgtc tcttcagcct ccaccaaggg cccatcggtc    420
ttccccctgg cac                                                       433

<210> SEQ ID NO 63
<211> LENGTH: 144
<212> TYPE: PRT
<213> ORGANISM: Homo sapiens

<400> SEQUENCE: 63

Met Glu Phe Val Leu Ser Trp Val Leu Leu Val Ala Ile Leu Lys Gly
1               5                   10                  15

Val Gln Cys Glu Val Gln Leu Val Gln Ser Gly Gly Gly Leu Val His
                20                  25                  30
```

```
Pro Gly Gly Ser Leu Arg Leu Ser Cys Ala Gly Ser Gly Phe Thr Phe
            35                  40                  45
Ser Asn Tyr Ala Met His Trp Val Arg Gln Ala Pro Gly Lys Gly Leu
 50                  55                  60
Glu Trp Val Ser Thr Ile Gly Thr Gly Gly Thr Pro Tyr Ala Asp
 65                  70                  75                  80
Ser Val Lys Gly Arg Phe Thr Ile Ser Arg Asp Asn Ala Lys Asn Ser
                 85                  90                  95
Leu Tyr Leu Gln Met Asn Ser Leu Arg Ala Glu Asp Met Ala Val Tyr
            100                 105                 110
Tyr Cys Ala Leu Ser Ala Phe Asp Val Trp Gly Gln Gly Thr Met Val
        115                 120                 125
Thr Val Ser Ser Ala Ser Thr Lys Gly Pro Ser Val Phe Pro Leu Ala
    130                 135                 140

<210> SEQ ID NO 64
<211> LENGTH: 125
<212> TYPE: PRT
<213> ORGANISM: Homo sapiens

<400> SEQUENCE: 64

Glu Val Gln Leu Val Gln Ser Gly Gly Gly Leu Val His Pro Gly Gly
 1               5                  10                  15
Ser Leu Arg Leu Ser Cys Ala Gly Ser Gly Phe Thr Phe Ser Asn Tyr
                20                  25                  30
Ala Met His Trp Val Arg Gln Ala Pro Gly Lys Gly Leu Glu Trp Val
            35                  40                  45
Ser Thr Ile Gly Thr Gly Gly Thr Pro Tyr Ala Asp Ser Val Lys
 50                  55                  60
Gly Arg Phe Thr Ile Ser Arg Asp Asn Ala Lys Asn Ser Leu Tyr Leu
 65                  70                  75                  80
Gln Met Asn Ser Leu Arg Ala Glu Asp Met Ala Val Tyr Tyr Cys Ala
                85                  90                  95
Leu Ser Ala Phe Asp Val Trp Gly Gln Gly Thr Met Val Thr Val Ser
            100                 105                 110
Ser Ala Ser Thr Lys Gly Pro Ser Val Phe Pro Leu Ala
        115                 120                 125

<210> SEQ ID NO 65
<211> LENGTH: 5
<212> TYPE: PRT
<213> ORGANISM: Homo sapiens

<400> SEQUENCE: 65

Asn Tyr Ala Met His
 1               5

<210> SEQ ID NO 66
<211> LENGTH: 16
<212> TYPE: PRT
<213> ORGANISM: Homo sapiens

<400> SEQUENCE: 66

Thr Ile Gly Thr Gly Gly Gly Thr Pro Tyr Ala Asp Ser Val Lys Gly
 1               5                  10                  15

<210> SEQ ID NO 67
<211> LENGTH: 5
<212> TYPE: PRT
<213> ORGANISM: Homo sapiens
```

<400> SEQUENCE: 67

Ser Ala Phe Asp Val
1               5

<210> SEQ ID NO 68
<211> LENGTH: 466
<212> TYPE: DNA
<213> ORGANISM: Homo sapiens

<400> SEQUENCE: 68

```
atggagtttg tgctgagctg ggttttcctt gttgctatat taaaaggtgt ccagtgtgag    60
gttcagctgg tgcagtctgg gggaggcttg gtacatcctg gggggtccct gagactctcc   120
tgtgcaggct ctggattcac cttcagtagc tatgctatgc actgggttcg ccaggctcca   180
ggaaaaggtc tggagtgggt atcagctatt ggtactggtg ttacacata ctatgtagac    240
tccgtgaagg gccgattcac catctccaga gacaatgcca agaagtcctt gtatcttcaa   300
atgaacagcc tgagagccga ggacatggct gtgtattact gtgcaagaga gccgttttac   360
gatattttga ctggttattc cccatacttt gactactggg gccagggaac cctggtcacc   420
gtctcctcag cctccaccaa gggcccatcg gtcttccccc tggcac                  466
```

<210> SEQ ID NO 69
<211> LENGTH: 143
<212> TYPE: PRT
<213> ORGANISM: Homo sapiens

<400> SEQUENCE: 69

Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Gly Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ser Ala Ile Gly Thr Gly Gly Tyr Thr Tyr Tyr Val Asp
65                  70                  75                  80

Ser Val Lys Gly Arg Phe Thr Ile Ser Arg Asp Asn Ala Lys Lys Ser
                85                  90                  95

Leu Tyr Leu Gln Met Asn Ser Leu Arg Ala Glu Asp Met Ala Val Tyr
            100                 105                 110

Tyr Cys Ala Arg Glu Pro Phe Tyr Asp Ile Leu Thr Gly Tyr Ser Pro
        115                 120                 125

Tyr Phe Asp Tyr Trp Gly Gln Gly Thr Leu Val Thr Val Ser Ser
    130                 135                 140

<210> SEQ ID NO 70
<211> LENGTH: 124
<212> TYPE: PRT
<213> ORGANISM: Homo sapiens

<400> SEQUENCE: 70

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

```
Ser Ala Ile Gly Thr Gly Gly Tyr Thr Tyr Tyr Val Asp Ser Val Lys
        50                  55                  60
Gly Arg Phe Thr Ile Ser Arg Asp Asn Ala Lys Lys Ser Leu Tyr Leu
 65                  70                  75                  80
Gln Met Asn Ser Leu Arg Ala Glu Asp Met Ala Val Tyr Tyr Cys Ala
                85                  90                  95
Arg Glu Pro Phe Tyr Asp Ile Leu Thr Gly Tyr Ser Pro Tyr Phe Asp
            100                 105                 110
Tyr Trp Gly Gln Gly Thr Leu Val Thr Val Ser Ser
            115                 120
```

<210> SEQ ID NO 71
<211> LENGTH: 5
<212> TYPE: PRT
<213> ORGANISM: Homo sapiens

<400> SEQUENCE: 71

```
Ser Tyr Ala Met His
 1               5
```

<210> SEQ ID NO 72
<211> LENGTH: 16
<212> TYPE: PRT
<213> ORGANISM: Homo sapiens

<400> SEQUENCE: 72

```
Ala Ile Gly Thr Gly Gly Tyr Thr Tyr Tyr Val Asp Ser Val Lys Gly
 1               5                  10                  15
```

<210> SEQ ID NO 73
<211> LENGTH: 16
<212> TYPE: PRT
<213> ORGANISM: Homo sapiens

<400> SEQUENCE: 73

```
Glu Pro Phe Tyr Asp Ile Leu Thr Gly Tyr Ser Pro Tyr Phe Asp Tyr
 1               5                  10                  15
```

<210> SEQ ID NO 74
<211> LENGTH: 454
<212> TYPE: DNA
<213> ORGANISM: Homo sapiens

<400> SEQUENCE: 74

```
atggagtttg ggctgagctg ggttttcctc gttgctcttt taagaggtgt ccagtgtcag      60
gtgcagctgg tggagtctgg gggaggcgtg gtccagcctg gaggtccct  gagactctcc     120
tgtgcagcgt ctggattcac cttcagtagc tataacatgc actgggtccg ccaggctcca    180
ggcaagggc  tggagtgggt ggcagttata tggtatgatg aagtaataa  atactatgga    240
gactccgtga agggccgatt caccatctcc agagacaatt ccaagaacac gctgtatctg    300
caaatgaaca gcctgagagc cgaggacacg gctgtgtatt actgtgcgag agaagagctg    360
gggatcgggt ggtacttcga tctctggggc cgtggcaccc tggtcactgt ctcctcagcc    420
tccaccaagg gcccatcggt cttccccctg gcac                                454
```

<210> SEQ ID NO 75
<211> LENGTH: 139
<212> TYPE: PRT
<213> ORGANISM: Homo sapiens -continued

```
<400> SEQUENCE: 75

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Asn Met His Trp Val Arg Gln Ala Pro Lys Gly Leu
    50                  55                  60

Glu Trp Val Ala Val Ile Trp Tyr Asp Gly Ser Asn Lys Tyr Tyr Gly
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Glu Leu Gly Ile Gly Trp Tyr Phe Asp Leu
        115                 120                 125

Trp Gly Arg Gly Thr Leu Val Thr Val Ser Ser
    130                 135

<210> SEQ ID NO 76
<211> LENGTH: 120
<212> TYPE: PRT
<213> ORGANISM: Homo sapiens

<400> SEQUENCE: 76

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Asn Met His Trp Val Arg Gln Ala Pro Gly Lys Gly Leu Glu Trp Val
            35                  40                  45

Ala Val Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Leu Gly Ile Gly Trp Tyr Phe Asp Leu Trp Gly Arg
            100                 105                 110

Gly Thr Leu Val Thr Val Ser Ser
        115                 120

<210> SEQ ID NO 77
<211> LENGTH: 5
<212> TYPE: PRT
<213> ORGANISM: Homo sapiens

<400> SEQUENCE: 77

Ser Tyr Asn Met His
1               5

<210> SEQ ID NO 78
<211> LENGTH: 17
<212> TYPE: PRT
<213> ORGANISM: Homo sapiens
```

-continued

<400> SEQUENCE: 78

Val Ile Trp Tyr Asp Gly Ser Asn Lys Tyr Tyr Gly Asp Ser Val Lys
1               5                   10                  15

Gly

<210> SEQ ID NO 79
<211> LENGTH: 11
<212> TYPE: PRT
<213> ORGANISM: Homo sapiens

<400> SEQUENCE: 79

Glu Glu Leu Gly Ile Gly Trp Tyr Phe Asp Leu
1               5                   10

<210> SEQ ID NO 80
<211> LENGTH: 475
<212> TYPE: DNA
<213> ORGANISM: Homo sapiens

<400> SEQUENCE: 80

```
atggacatga gggtccccgc tcagctcctg gggcttctgc tgctctggct cccaggtgcc      60
agatgtgcca tccagttgac ccagtctcca tcctccctgt ctgcatctgt aggagacaga     120
gtcaccatca cttgccgggc aagtcagggc attagcagtg ctttagcctg gtatcagcag     180
aaaccaggga aagctcctaa gctcctgatc tatgatgcct ccagtttgga aagtggggtc     240
ccatcaaggt tcagcggcag tggatctggg acagatttca ctctcaccat cagcagcctg     300
cagcctgaag attttgcaac ttattactgt caacagttta atagttaccc tcacttcggc     360
caagggacac gactggagat taaacgaact gtggctgcac catctgtctt catcttcccg     420
ccatctgatg agcagttgaa atctggaact gcctctgttg tgtgcctgca agggc          475
```

<210> SEQ ID NO 81
<211> LENGTH: 128
<212> TYPE: PRT
<213> ORGANISM: Homo sapiens

<400> SEQUENCE: 81

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Ser Ser Ala Leu Ala Trp Tyr Gln Gln Lys Pro Gly Lys
        50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro His Phe Gly Gln Gly Thr Arg Leu Glu Ile Lys
        115                 120                 125

<210> SEQ ID NO 82
<211> LENGTH: 106
<212> TYPE: PRT
<213> ORGANISM: Homo sapiens

<400> SEQUENCE: 82

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Phe Gly Gln Gly Thr Arg Leu Glu Ile Lys
            100                 105

<210> SEQ ID NO 83
<211> LENGTH: 11
<212> TYPE: PRT
<213> ORGANISM: Homo sapiens

<400> SEQUENCE: 83

Arg Ala Ser Gln Gly Ile Ser Ser Ala Leu Ala
1               5                   10

<210> SEQ ID NO 84
<211> LENGTH: 7
<212> TYPE: PRT
<213> ORGANISM: Homo sapiens

<400> SEQUENCE: 84

Asp Ala Ser Ser Leu Glu Ser
1               5

<210> SEQ ID NO 85
<211> LENGTH: 8
<212> TYPE: PRT
<213> ORGANISM: Homo sapiens

<400> SEQUENCE: 85

Gln Gln Phe Asn Ser Tyr Pro His
1               5

<210> SEQ ID NO 86
<211> LENGTH: 445
<212> TYPE: DNA
<213> ORGANISM: Homo sapiens

<400> SEQUENCE: 86
atggagtttg ggctgagctg ggttttcctc gttgctcttt taagaggtgt ccagtgtcag      60
gtgcagctgg tggagtctgg gggaggcgtg gtccagcctg gaggtccct  gagactctcc    120 tgtgcagcgt ctggattcac cttcagtagc tatggcatgc actgggtccg ccaggctcca    180
ggcaaggggc tggagtgggt ggcagttata tggtatgatg aagtaataa  atactatgca    240 gactccgtga agggccgatt caccatctcc agagacaatt ccaagaacac gctgtatctg    300
caaatgaaca gcctgagagc cgaggacacg gctgtgtatt actgtgcgag aggccccct    360 cggtacttcg atctctgggg ccgtggcacc ctggtcactg tctcctcagc ctccaccaag    420
ggcccatcgg tcttccccct ggcac                                          445

```
<210> SEQ ID NO 87
<211> LENGTH: 136
<212> TYPE: PRT
<213> ORGANISM: Homo sapiens

<400> SEQUENCE: 87

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Pro Pro Arg Tyr Phe Asp Leu Trp Gly Arg
        115                 120                 125

Gly Thr Leu Val Thr Val Ser Ser
    130                 135

<210> SEQ ID NO 88
<211> LENGTH: 117
<212> TYPE: PRT
<213> ORGANISM: Homo sapiens

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Pro Arg Tyr Phe Asp Leu Trp Gly Arg Gly Thr Leu
            100                 105                 110

Val Thr Val Ser Ser
        115

<210> SEQ ID NO 89
<211> LENGTH: 5
<212> TYPE: PRT
<213> ORGANISM: Homo sapiens

<400> SEQUENCE: 89

Ser Tyr Gly Met His
1               5
```

```
<210> SEQ ID NO 90
<211> LENGTH: 17
<212> TYPE: PRT
<213> ORGANISM: Homo sapiens

<400> SEQUENCE: 90

Val Ile Trp Tyr Asp Gly Ser Asn Lys Tyr Tyr Ala Asp Ser Val Lys
 1               5                  10                  15

Gly

<210> SEQ ID NO 91
<211> LENGTH: 8
<212> TYPE: PRT
<213> ORGANISM: Homo sapiens

<400> SEQUENCE: 91

Gly Pro Pro Arg Tyr Phe Asp Leu
 1               5

<210> SEQ ID NO 92
<211> LENGTH: 95
<212> TYPE: PRT
<213> ORGANISM: Homo sapiens

<400> SEQUENCE: 92

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                 85                  90                  95

<210> SEQ ID NO 93
<211> LENGTH: 95
<212> TYPE: PRT
<213> ORGANISM: Homo sapiens

<400> SEQUENCE: 93

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 94
<211> LENGTH: 95
<212> TYPE: PRT
<213> ORGANISM: Homo sapiens
```

-continued

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 95
<211> LENGTH: 98
<212> TYPE: PRT
<213> ORGANISM: Homo sapiens

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 96
<211> LENGTH: 97
<212> TYPE: PRT
<213> ORGANISM: Homo sapiens

<400> SEQUENCE: 96

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

```
<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ile, Asn, Thr or Ser
<220> FEATURE:
<221> NAME/KEY: MOD_RES
<222> LOCATION: (3)..(3)
<223> OTHER INFORMATION: Gly, Asn or Ala
<220> FEATURE:
<221> NAME/KEY: MOD_RES
<222> LOCATION: (5)..(5)
<223> OTHER INFORMATION: His or Tyr

<400> SEQUENCE: 97

Xaa Tyr Xaa Met Xaa
1               5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Val, Ile, Phe, Thr or Ala
<220> FEATURE:
<221> NAME/KEY: MOD_RES
<222> LOCATION: (3)..(3)
<223> OTHER INFORMATION: Trp or Gly
<220> FEATURE:
<221> NAME/KEY: MOD_RES
<222> LOCATION: (4)..(4)
<223> OTHER INFORMATION: Tyr or Thr
<220> FEATURE:
<221> NAME/KEY: MOD_RES
<222> LOCATION: (5)..(5)
<223> OTHER INFORMATION: Asp or Gly
<220> FEATURE:
<221> NAME/KEY: MOD_RES
<222> LOCATION: (7)..(7)
<223> OTHER INFORMATION: Ser, Gly or Tyr
<220> FEATURE:
<221> NAME/KEY: MOD_RES
<222> LOCATION: (8)..(8)
<223> OTHER INFORMATION: Asn or Thr
<220> FEATURE:
<221> NAME/KEY: MOD_RES
<222> LOCATION: (9)..(9)
<223> OTHER INFORMATION: Lys or Pro
<220> FEATURE:
<221> NAME/KEY: MOD_RES
<222> LOCATION: (11)..(11)
<223> OTHER INFORMATION: Tyr, Ala or Val
<220> FEATURE:
<221> NAME/KEY: MOD_RES
<222> LOCATION: (12)..(12)
<223> OTHER INFORMATION: Ala, Gly or not present

<400> SEQUENCE: 98

Xaa Ile Xaa Xaa Xaa Gly Xaa Xaa Xaa Tyr Xaa Xaa Asp Ser Val Lys
1               5                   10                  15

Gly
```

```
<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ala, Gly, Tyr, Ser, Pro or not present
<220> FEATURE:
<221> NAME/KEY: MOD_RES
<222> LOCATION: (2)..(2)
<223> OTHER INFORMATION: Pro, Trp, Ser or Arg
<220> FEATURE:
<221> NAME/KEY: MOD_RES
<222> LOCATION: (3)..(3)
<223> OTHER INFORMATION: Tyr, Ala or His
<220> FEATURE:
<221> NAME/KEY: MOD_RES
<222> LOCATION: (6)..(6)
<223> OTHER INFORMATION: Tyr, Leu or Val

<400> SEQUENCE: 99

Xaa Xaa Xaa Phe Asp Xaa
1               5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (5)..(5)
<223> OTHER INFORMATION: Ser or Gly
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (9)..(9)
<223> OTHER INFORMATION: Tyr, Trp or Ala

<400> SEQUENCE: 100

Arg Ala Ser Gln Xaa Xaa Ser Ser Xaa Leu Ala
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asp or Ala
<220> FEATURE:
<221> NAME/KEY: MOD_RES
<222> LOCATION: (4)..(4)
<223> OTHER INFORMATION: Asn or Ser
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Ala, Gln or Glu
```

```
<220> FEATURE:
<221> NAME/KEY: MOD_RES
<222> LOCATION: (7)..(7)
<223> OTHER INFORMATION: Thr or Ser

<400> SEQUENCE: 101

Xaa Ala Ser Xaa Xaa Xaa Xaa
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Arg, Tyr or Phe
<220> FEATURE:
<221> NAME/KEY: MOD_RES
<222> LOCATION: (4)..(4)
<223> OTHER INFORMATION: Arg or Asn
<220> FEATURE:
<221> NAME/KEY: MOD_RES
<222> LOCATION: (5)..(5)
<223> OTHER INFORMATION: Thr, Ser or Asn
<220> FEATURE:
<221> NAME/KEY: MOD_RES
<222> LOCATION: (6)..(6)
<223> OTHER INFORMATION: Tyr, Trp or not present
<220> FEATURE:
<221> NAME/KEY: MOD_RES
<222> LOCATION: (7)..(7)
<223> OTHER INFORMATION: Pro or not present
<220> FEATURE:
<221> NAME/KEY: MOD_RES
<222> LOCATION: (8)..(8)
<223> OTHER INFORMATION: Tyr, Leu, His or not present
<220> FEATURE:
<221> NAME/KEY: MOD_RES
<222> LOCATION: (9)..(9)
<223> OTHER INFORMATION: Thr or not present

<400> SEQUENCE: 102

Gln Gln Xaa Xaa Xaa Xaa Xaa Xaa Xaa
1               5

<210> SEQ ID NO 103
<211> LENGTH: 118
<212> TYPE: PRT
<213> ORGANISM: Homo sapiens

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Leu Trp Gly Trp Tyr Phe Asp Tyr Trp Gly Gln Gly Thr
            100                 105                 110

Leu Val Thr Val Ser Ser
        115
```

<210> SEQ ID NO 104
<211> LENGTH: 117
<212> TYPE: PRT
<213> ORGANISM: Homo sapiens

<400> SEQUENCE: 104

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Tyr Trp Tyr Phe Asp Leu Trp Gly Arg Gly Thr Leu
            100                 105                 110

Val Thr Val Ser Ser
        115
```

<210> SEQ ID NO 105
<211> LENGTH: 120
<212> TYPE: PRT
<213> ORGANISM: Homo sapiens

<400> SEQUENCE: 105

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asn Met His Trp Val Arg Gln Ala Pro Gly Lys Gly Leu Glu Trp Val
        35                  40                  45

Ala Phe Ile Trp Tyr Asp Gly Ser Asn Lys Tyr Tyr Gly Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Leu Gly Ile Gly Trp Tyr Phe Asp Leu Trp Gly Arg
            100                 105                 110

Gly Thr Leu Val Thr Val Ser Ser
        115                 120
```

<210> SEQ ID NO 106
<211> LENGTH: 113
<212> TYPE: PRT
<213> ORGANISM: Homo sapiens -continued

```
<400> SEQUENCE: 106

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ser Thr Ile Gly Thr Gly Gly Thr Pro Tyr Ala Asp Ser Val Lys
    50                  55                  60

Gly Arg Phe Thr Ile Ser Arg Asp Asn Ala Lys Asn Ser Leu Tyr Leu
65              70                  75                  80

Gln Met Asn Ser Leu Arg Ala Glu Asp Met Ala Val Tyr Tyr Cys Ala
                85                  90                  95

Leu Ser Ala Phe Asp Val Trp Gly Gln Gly Thr Met Val Thr Val Ser
            100                 105                 110

Ser
```